United States Patent [19]
Burow, Jr.

[11] Patent Number: 4,801,718
[45] Date of Patent: Jan. 31, 1989

[54] THIAIAZOLYL BENZAMIDES
[75] Inventor: Kenneth W. Burow, Jr., Indianapolis, Ind.
[73] Assignee: Eli Lilly and Company, Indianapolis, Ind.
[21] Appl. No.: 805,020
[22] Filed: Dec. 5, 1985

Related U.S. Application Data

[60] Division of Ser. No. 685,922, Dec. 24, 1984, Pat. No. 4,636,243, which is a division of Ser. No. 510,699, Jul. 5, 1983, Pat. No. 4,515,625; which is a division of Ser. No. 302,323, Sep. 14, 1981, Pat. No. 4,416,683, which is a continuation-in-part of Ser. No. 187,675, Sep. 16, 1980, abandoned.

[51] Int. Cl.$^4$ .......................................... C07D 285/12
[52] U.S. Cl. .................................... 548/139; 548/125; 548/127; 548/128; 548/131; 548/133; 548/143; 548/245; 548/261; 548/265; 548/337; 548/377; 544/224; 549/22; 549/369
[58] Field of Search ................ 548/127, 128, 139; 71/90

[56] References Cited

U.S. PATENT DOCUMENTS

| | | | |
|---|---|---|---|
| 3,277,107 | 10/1966 | Neighbors | 260/306.8 |
| 3,340,042 | 9/1967 | Schwartz et al. | 71/94 |
| 3,407,056 | 10/1968 | Schwartz | 71/118 |
| 3,541,108 | 11/1970 | Schmidt et al. | 260/306.8 |
| 3,629,275 | 12/1971 | Metzger et al. | 260/306.8 |
| 3,717,651 | 2/1973 | Pilgram et al. | 260/306.8 R |
| 3,772,316 | 11/1973 | Wakae et al. | 260/306.8 D |
| 3,776,919 | 12/1973 | Sasse et al. | 260/306.8 |
| 3,784,555 | 1/1974 | Cebalo | 260/306.8 D |
| 3,903,155 | 9/1975 | Teach | 260/553 A |
| 3,920,674 | 11/1975 | Krenzer | 260/306.8 |
| 3,959,303 | 5/1976 | Cebalo | 260/306.8 |
| 3,990,879 | 11/1976 | Soper | 71/60 |
| 4,089,962 | 5/1978 | Harrison et al. | 424/269 |
| 4,128,412 | 12/1978 | Metzger et al. | 71/90 |
| 4,141,984 | 2/1979 | Ward | 424/270 |
| 4,152,442 | 5/1979 | Ross et al. | 424/270 |
| 4,182,712 | 1/1980 | Driscoll | 548/140 |
| 4,187,098 | 2/1980 | Patel | 71/90 |
| 4,191,554 | 3/1980 | Gregory | 71/95 |
| 4,337,081 | 6/1982 | Gay | 71/90 |

FOREIGN PATENT DOCUMENTS

| | | |
|---|---|---|
| 49-8259 | 2/1974 | Japan . |
| 50-117934 | 9/1975 | Japan . |
| 51-612 | 1/1976 | Japan . |
| 1548397 | 7/1979 | United Kingdom . |

OTHER PUBLICATIONS

Sasaki, "Adamantane Derivatives", (1970), CA 74:3629a (1971).
Ried et al, "Reactions with Diazocarbonyl etc.", (1964), CA 61:3093d (1964).
Regitz et al, "Studies of Diazo Compounds, Etc." (1980), CA 92:214519z, 1980.
Boggiano et al, "Hypoglycemic Agents", 1961, CA 56:4747h, 1961.
Jensen et al, "Tuberculostatic Derivatives", (1949) CA 43:7454, 1949.
Goerdeler et al, "5-Amino-1,2,3-Thiradiazoles Etc.", (1966) CA: 38:2249e.
Baruffini et al., Farmaco, Ed. Sci. 1974, 29(4) 317–326, cf. CA:81 73303h (1974).
Boggiano, et al., J. Pharm. and Pharmacol, 13, 567–574 (1961), cf C.A. 564747h–4748g (1962).
Jensen et al., Acta Chem. Scand., 3, 13–16 (1949) cf. Chem. Abs., 7454i (1949).

Primary Examiner—Richard L. Raymond
Assistant Examiner—Patricia L. Morris
Attorney, Agent, or Firm—Donald R. Stuart; Leroy Whitaker; Charles W. Ashhbrook

[57] ABSTRACT

N-Aryl benzamides wherein the aryl group is a nitrogen containing heterocycle are useful as selective herbicidal agents. Compositions containing the novel benzamides and a herbicidal method of selective weed control are disclosed.

24 Claims, No Drawings

THIAIAZOLYL BENZAMIDES

CROSS REFERENCE TO RELATED APPLICATIONS

This application is a division of Ser. No. 685,922, filed Dec. 24, 1984, now U.S. Pat. No. 4,636,243 which is a division of Ser. No. 510,699, filed July 5, 1983, now U.S. Pat. No. 4,515,625; which is a division of Ser. No. 302,323, filed Sept. 14, 1981, now U.S. Pat. No. 4,416,683, which is a continuation-in-part of Ser. No. 187,675, filed Sept. 16, 1980, now abandoned.

BACKGROUND OF THE INVENTION

The use of herbicides to selectively control the growth of unwanted vegetation in crops grown for human and domestic animal consumption is well established. A number of problems are associated with the continued use of chemical herbicides however, including environmental pollution, crop tolerance, weed resistance, as well as economic considerations. Accordingly, the search continues for new herbicides which are economical and which are selectively toxic to unwanted vegetation.

A wide variety of benzamides are known in the art. Ward, for example, in U.S. Pat. No. 4,141,984, discloses certain thiadiazolyl benzamides which are said to possess insecticidal efficacy. Kaplan et al., in U.S. Pat. No. 4,189,495, disclose a series of 2-methoxybenzamides which allegedly possess pharmacological activity.

An object of the present invention is to provide a novel class of N-aryl benzamides which are potent herbicides. A further object is to provide compositions containing such compounds, as well as a method for their use.

SUMMARY OF THE INVENTION

The present invention relates to herbicidal benzamide derivatives, and more particularly to N-aryl benzamides of the formula

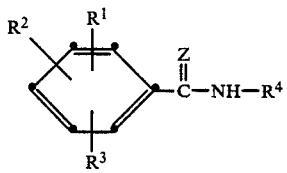

wherein:
Z is oxygen or sulfur;
$R^1$ is hydrogen, halogen, $C_1$–$C_4$ alkyl, or $C_1$–$C_4$ alkoxy;
$R^2$ is hydrogen, halogen, $C_1$–$C_4$ alkyl, $C_1$–$C_4$ alkoxy, $C_1$–$C_4$ alkylthio or trifluoromethyl;
$R^3$ is hydrogen, halogn, $C_1$–$C_4$ alkyl, $C_1$–$C_4$ alkoxy or $C_1$–$C_4$ alkylthio; provided that when one of $R^1$, $R^2$ or $R^3$ is alkyl, one or both of the other phenyl substituents is other than hydrogen; and when $R^2$ is trifluoromethyl, one or both of $R^1$ and $R^3$ is other than hydrogen;
$R^4$ is an aryl group selected from

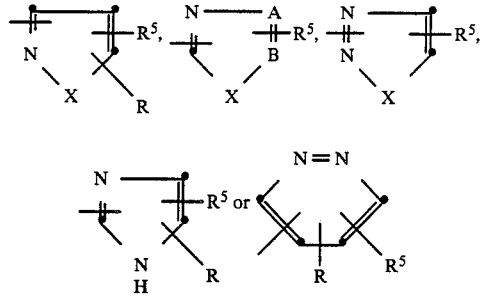

wherein:
R is hydrogen or $C_1$–$C_4$ alkyl;
A is CH or N and B is CH or N, provided that one of A and B is CH and the other is N;
X is NH, O or S;
$R^5$ is hydrogen,

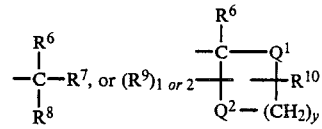

wherein:
$R^6$ is hydrogen, $C_1$–$C_4$ alkyl, $C_2$–$C_4$ alkenyl, $C_2$–$C_4$ alkynyl, $C_1$–$C_6$ alkoxy, or $C_1$–$C_6$ alkylthio;
y is an integer from 0 to 5;
$R^7$ and $R^8$ independently are hydrogen, $C_1$–$C_{13}$ alkyl, halo-$C_1$–$C_{13}$ alkyl, $C_2$–$C_{13}$ alkenyl, $C_2$–$C_{13}$ alkynyl, $C_1$–$C_6$ alkoxy, $C_1$–$C_6$-alkylthio, $C_1$–$C_4$ alkoxy-$C_1$–$C_6$ alkyl, $C_1$–$C_4$ alkylthio-$C_1$–$C_6$ alkyl, $C_2$–$C_4$ alkanoyloxy-$C_1$–$C_6$ alkyl,

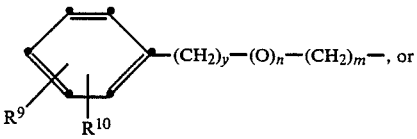

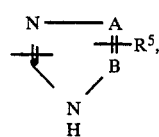

in which m is an integer from 0 to 4; n is zero or 1; $R^9$ and $R^{10}$ independently are hydrogen, halogen, $C_1$–$C_4$ alkyl or $C_2$–$C_4$ alkenyl; $Q^1$ and $Q^2$ independently are $CH_2$, $-(CH_2)_n-O-$ or $-(CH_2)_n-S-$; provided that when $Q^1$ and $Q^2$ are both other than $CH_2$, y is other than zero; and provided that $R^5$ is hydrogen only when $R^4$ is and provided that $R^2$ and $R^3$ are other than hydrogen when $R^4$ is

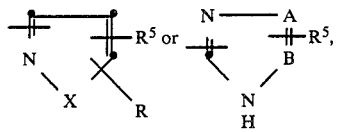

and the agronomically acceptable salts thereof.

A particularly valuable class of herbicidal benzamides provided by this invention are defined by the above formula wherein Z is oxygen, $R^4$ is

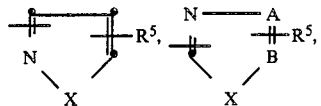

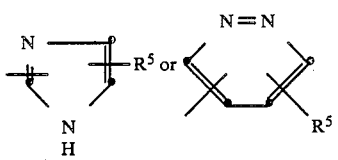

$R^5$ is hydrogen,

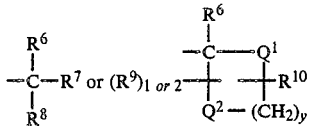

in which $R^6$ and $R^7$ independently are hydrogen, $C_1$–$C_4$ alkyl, $C_2$–$C_4$ alkenyl; or $C_2$–$C_4$ alkynyl;

y is an integer from 0 to 4;

$R^8$ is as defined other than alkoxy, alkylthio or alkanoyloxy; and $Q^1$ and $Q^2$ both are —$CH_2$—.

Preferred compounds are those defined by the above formula wherein one or more of the following characteristics apply;

(a) Z is oxygen;
(b) R is hydrogen;
(c) $R^1$ is hydrogen and $R^2$ and $R^3$ independently are $C_1$–$C_4$ alkoxy, $C_1$–$C_4$ alkyl, or $C_1$–$C_4$ alkylthio, especially when attached at the 2 and 6-positions;
(d) $R^1$ is hydrogen and $R^2$ and $R^3$ independently are $C_1$–$C_4$ alkoxy, preferably attached at the 2 and 6-positions;
(e) $R^1$ is hydrogen, $R^2$ is 2-methoxy or 2-ethoxy and $R^3$ is 6-methoxy or 6-ethoxy;
(f) $R^4$ is

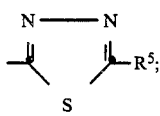

(g) $R^4$ is

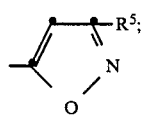

(h) $R^4$ is

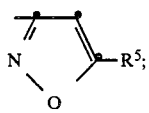

(i) $R^4$ is

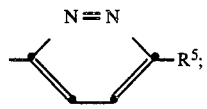

(j) $R^5$ is

wherein $R^6$ is $C_1$–$C_4$ alkyl;

(k) $R^5$ is

wherein one or both of $R^6$ and $R^7$ independently are $C_1$–$C_4$ alkyl;

(l) $R^5$ is

wherein one or both of $R^6$ and $R^7$ independently are $C_1$–$C_4$ alkyl and $R^8$ is $C_1$–$C_{13}$ alkyl or cycloalkyl of the formula

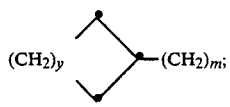

(m) $R^5$ is

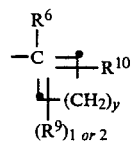

wherein $R^6$ is $C_1$–$C_4$ alkyl and $R^9$ and $R^{10}$ both are hydrogen;

(n) $R^5$ is 1-ethyl-1-methylpropyl;
(o) $R^5$ is 1,1-dimethylethyl;
(p) $R^5$ is 1-ethylcyclohexyl.

Also provided by this invention are formulations comprising a benzamide of the above general formula together with an agronomically-acceptable carrier, diluent, or adjuvant therefor. Compositions comprising a benzamide as defined above in combination with one or more other compatible herbicides are also contemplated.

Additionally provided by the invention is a method for controlling the growth of unwanted vegetation comprising applying to the locus where vegetative control is desired a herbicidally-effective amount of a benzamide defined by the above general formula. The herbicidal method is ideally carried out employing the preferred benzamides as delineated above. For example, a preferred method comprises applying to the locus where the growth of unwanted vegetation is to be eliminated or retarded a herbicidally effective amount of a benzamide of the formula

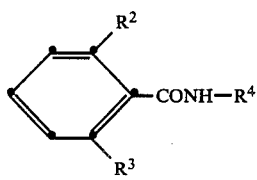

wherein $R^2$ and $R^3$ independently are $C_1$–$C_4$ alkoxy such as methoxy or ethoxy, and $R^4$ is selected from

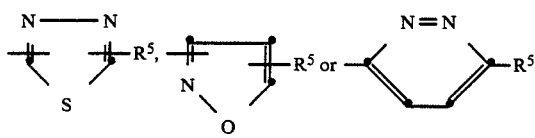

wherein $R^5$ is

and $R^6$ and $R^7$ independently are $C_1$–$C_4$ alkyl and $R^8$ is $C_1$–$C_{13}$ alkyl or cycloalkyl of the formula

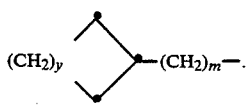

DETAILED DESCRIPTION OF THE INVENTION

The term "benzamide" when used herein shall include compounds of the above formula wherein Z is oxygen and thiobenzamide compounds of the above formula wherein Z is sulfur. Preferred compounds of the invention are benzamides of the above formula wherein Z is oxygen.

$R^1$, $R^2$ and $R^3$ are used in the above formula to define groups which incude $C_1$–$C_4$ alkyl, $C_1$–$C_4$ alkoxy, $C_1$–$C_4$ alkylthio, and halogen. The term "$C_1$–$C_4$ alkyl" refers to both straight and branched chain alkyl groups such as methyl, ethyl, isopropyl and tert.-butyl. The term "$C_1$–$C_4$ alkoxy" refers to the same $C_1$–$C_4$ alkyl groups which are linked through an oxygen atom. Such groups include methoxy, n-propoxy, n-butoxy and the like. Typical "$C_1$–$C_4$ alkylthio" groups include methylthio, ethylthio and isopropylthio. "Halogen" as used herein refers to fluoro, chloro, bromo and iodo. As noted above, preferred benzamides are those wherein $R^1$ is hydrogen and $R^2$ and $R^3$ are alkoxy, especially methoxy or ethoxy attached at the 2 and 6-positions of the benzamide phenyl ring.

$R^4$ in the above formula defines an aryl moiety such as isoxazolyl, thiadiazolyl, isothiazolyl, triazolyl, pyrazolyl, oxadiazolyl, and pyridazinyl. The $R^4$ aryl substituents defined herein are represented by the following general formulas

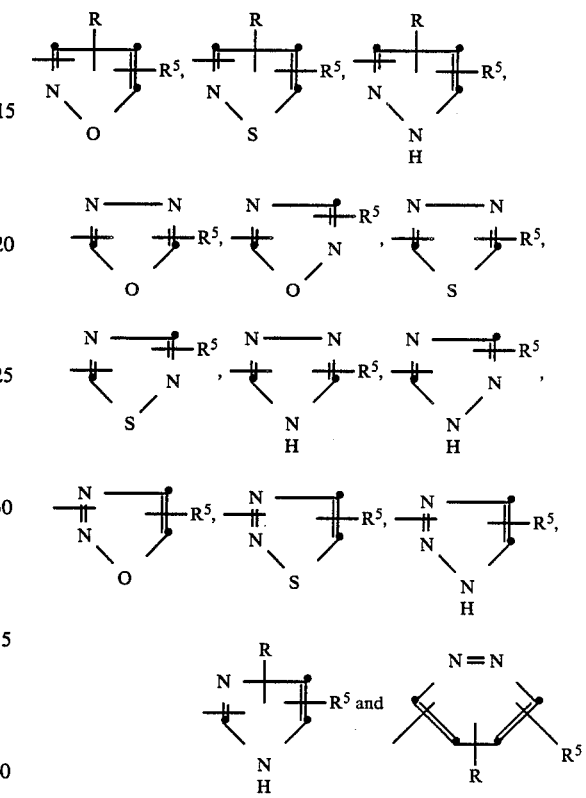

Preferred benzamides of the invention are those defined by the above formula wherein $R^4$ is 3-isoxazolyl, 5-isoxazolyl, 1,3,4-thiadiazolyl or 2-pyridazinyl.

The aryl moiety defined by $R^4$ is required to bear a substituent defined by $R^5$. It has been found that the most active, and accordingly the most preferred benzamides, are those wherein the aryl substituent defined by $R^5$ is a sterically hindered or bulky group. The concept of a sterically hindered or bulky group is known to those skilled in the art. Such terms include herein groups which are attached to the aryl ring through a secondary or tertiary carbon atom. Cyclic groups which are linked through a secondary or tertiary carbon atom also are bulky groups, as are cyclic groups attached directly to the aryl moiety.

A typical $R^5$ substituent which is preferred is a bulky alky group. For example, $R^5$ represents an alkyl substituent when it refers to a group of the formula

and $R^6$ and $R^7$ refer to hydrogen or $C_1$–$C_4$ alkyl and $R^8$ is $C_1$–$C_{13}$ alkyl. The most bulky alkyl groups clearly are those wherein one or both of $R^6$ and $R^7$ independently are $C_1-C_4$ alkyl, and benzamides bearing such substituents are preferred. Typically preferred bulky alkyl groups thus include tert.-butyl, 1,1-dimethylpropyl, 1,1-diethylpentyl, 1-ethyl-1-propylhexyl, 1-ethyl-1-methylpropyl, 1,1-diethyloctyl, 1,1-diethylpropyl, 1-methyl-1-n-propylheptyl, 1-ethyl-1-isopropyloctyl, and 1,1-di-n-propyldecyl.

Other bulky alkyl groups which can be utilized include 1,2-dimethylbutyl, 1,2-dimethylheptyl, 2,2-dimethylpentyl, 1-ethylheptyl, 2,2-diethylpropyl, 1,1-dimethyl-2,2-diethylbutyl, 1,1,2,2-tetramethylhexyl, and 1-methyl-1-n-propyl-2-ethyloctyl.

The aryl substituent defined by $R^5$ in the above formula can be any of several bulky substituents other than a straight or branched chain alkyl group, including cycloalkyl of the formula

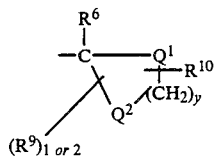

wherein $R^6$ is hydrogen, $C_1-C_4$ alkyl, $C_2-C_4$ alkenyl, $C_2-C_4$ alkynyl, $C_1-C_6$ alkoxy, or $C_1-C_6$ alkylthio; $R^9$ and $R^{10}$ independently are hydrogen, halogen, $C_1-C_4$ alkyl or $C_2-C_4$ alkenyl; $Q^1$ and $Q^2$ independently are $CH_2$, $-(CH_2)_nO-$ or $(CH_2)_nS-$, where n is zero and 1; and y is an integer from 0 to 4. Preferred such groups are those wherein $R^6$ is $C_1-C_4$ alkyl. Typical examples of such groups include 1-methylcyclobutyl, 1-ethylcyclopentyl, 1-n-propyl-2,2-dichlorocyclopropyl, 1-methylcycloheptyl, 1-ethylcycloheptyl, 1-ethyl-2,3-dimethylcyclobutyl, 1-n-propyl-2-allylcyclopentyl, 1,2,2-trimethyl-3-(2-methyl-1-propenyl)cyclopropyl, 2-methyl-1,3-dithian-2-yl, 5-ethyl-1,3-dithian-5-yl, 2-propyl-1,3-dioxan-2-yl, 5-methyl-1,3-dioxan-5-yl, 2-butyl-1,3-thioxan-2-yl, 5-ethyl-1,3-thioxan-5-yl and the like.

$R^5$ also refers to haloalkyl groups, alkenyl groups, and alkynyl groups, for instance when $R^5$ is $-CR^6R^7R^8$ wherein $R^7$ or $R^8$ is halo-$C_1-C_{13}$ alkyl, $C_2-C_{13}$ alkenyl or $C_2-C_{13}$ alkynyl respectively. Haloalkyl groups are $C_1-C_{13}$ alkyl groups bearing one or more halo substituents. Examples of such haloalkyl, alkenyl and alkynyl substituents as defined by $R^5$ include 1,1-dimethyl-3-chloropropyl, 1,2-diethyl-3-bromohexyl, 1-ethyl-1-n-propyl-8-iodononyl, 1,1-di-n-propyl-4,-4-difluorobutyl, 1-methyl-1-isopropyl-1,2-chlorododecyl, 1,1-dimethyl-3-butenyl, 2,3-diethy 4-hexenyl, 1,1-diethy-2,2-dimethyl-5-hexenyl, 1,1,2,2,3,3,-hexamethyl-9-decenyl, 1,1-dimethyl-4-hexynyl, 1,2-diethyl-3-heptynyl, 1-iso-propyl-3-butynyl, and the like.

$R^5$ in the above formula defining the benzamides of the invention additionally refers to $CR^6R^7R^8$ wherein $R^7$ or $R^8$ can be $C_1-C_4$ alkoxy-$C_1-C_6$ alkyl, $C_2-C_4$ alkanoyloxy-$C_1-C_6$ alkyl, or $C_1-C_4$ alkylthio-$C_1-C_6$ alkyl. These terms refer to straight or branched carbon chains from one to six carbon atoms in length which bear a $C_1-C_4$ straight or branched carbon chain linked through oxygen or sulfur, or a $C_2-C_4$ alkanoic acid residue such as acetoxy or butyroxy. Preferred alkoxyalkyl and alkylthioalkyl groups defined by $R^5$ are those which are sterically hindered or bulky, for example those which include a branched carbon chain attached directly to the aryl group (i.e. where one or both of $R^6$ and $R^7$ are alkyl). Such preferred groups include 1,1-dimethyl-2-methoxyethyl, 1-ethyl-3-methylthiopropyl, 1,1-diethyl-2-isopropoxyethyl, 1-n-propyl-3-tert.-butylthiopropyl and 2-ethyl-3-methyl-3-n-butoxypropyl. Other typical groups of this class include 1-methyl-1-acetoxymethyl-4-propionoxybutyl, 1-ethyl-1-(3-methylthiopropyl)-6-acetoxyhexyl, 1-n-propyl-1-(6-ethoxyhexyl)-6-isobutoxyhexyl, 1-ethyl-1-acetoxymethyl-3-ethylthiopropyl, 1-methyl-1-propionoxymethyl-4-methoxybutyl, and 1-(2-acetoxyethyl)-5-propoxypentyl.

$R^5$ also defines an alkyl group which bears a phenylalkyl or phenylalkoxy moiety, or a cycloalkyl moiety. For example, $R^5$ refers to the group $-CR^6R^7R^8$ in which $R^7$ or $R^8$ can include phenylalkyl, phenylalkoxy, cycloalkyl and cycloalkylalkyl substituents defined by the formulas

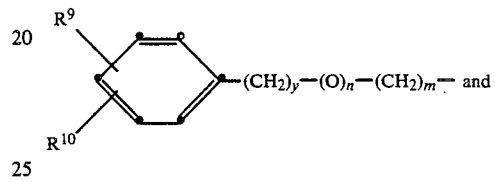

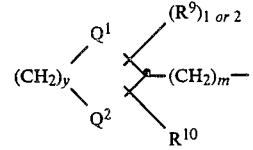

wherein y, m, n, $Q^1$, $Q^2$, $R^9$ and $R^{10}$ are defined above. Examples of benzamide aryl substituents thus defined by $R^5$ include 1,1-dimethyl-2-phenoxyethyl, 1,1-diethyl-3-benzyloxypropyl, 1,1-diethyl-2-phenylethyl, 1n-propyl-3-(2-chlorophenyl)butyl, 1,1-dimethyl-2-cyclohexylethyl, 1-ethyl-2-methyl-2-(3-allylcyclohexyl)ethyl, 1,1-diethyl-2-(3-phenylpropoxy)ethyl, 1-iso-propyl-4-(2,2-dichlorocyclopentyl)butyl, 1-ethyl-1-benzyl-4-cyclohexylbutyl, 1-methyl-1-phenoxy-3-(1,3-dioxan-2-yl)propyl, 1-n-butyl-1-cyclobutylmethyl-2-cyclohexylethyl, 1,1-dimethyl-3-(1,3-dithian-5-yl)propyl, 1-ethyl-4-(1-oxa-3-thian-2-yl)butyl and related groups.

The benzamides of this invention are prepared by processes which are presently known in the art or which are analogous to art-known synthetic methods. A preferred method for preparing the compounds is by acylation of an aryl amine of the formula $H_2NR^4$ with an appropriately substituted benzoic acid derivative according to the folowing sequence:

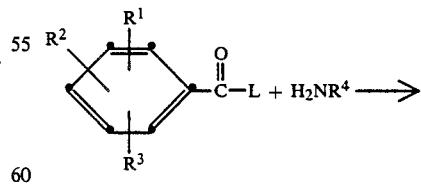

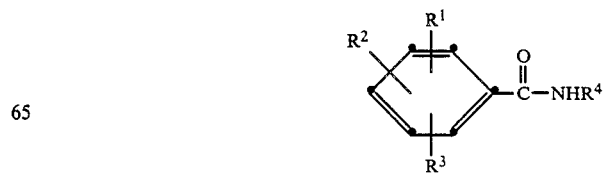

wherein $R^1$, $R^2$, $R^3$ and $R^4$ are as defined above, and L is a good leaving group, for example lower alkanoyloxy such as formyloxy or acetoxy, halide such as chloro, bromo or iodo, or an activated ester forming group such as pentachlorophenoxy or the like. A preferred good leaving group is halogen such as chloro or bromo.

The acylation reaction can be carried out by commingling the benzoic acid derivative with about an equimolar quantity of the aryl amine in a mutual solvent such as tetrahydrofuran, diethyl ether, dichloromethane, dioxane, dimethylsulfoxide, dimethylformamide, benzene, toluene, and the like. If desired, a base can be utilized in the acylation reaction to act as an acid scavenger. Commonly used bases include sodium carbonate, sodium hydride, potassium carbonate, sodium hydroxide, pyridine, triethylamine and related bases. The acylation generally is substantially complete after about two to about ninety hours when carried out at a temperature of about 20° to about 200° C., preferably from about 30° to about 120° C. The product of the reaction, an N-aryl benzamide of the invention, can be isolated by simply removing the reaction solvent, for instance by evaporation under reduced pressure. The product can be further purified if needed by any of several routine methods, including crystallization from solvents such as ethanol, ethyl acetate, diethyl ether, toluene, or the like; chromatography over solid supports such as silica or alumina, and related purification techniques.

An alternative method for preparing the N-aryl benzamides of this invention comprises the direct coupling of a substituted benzoic acid with an aryl amine. Such coupling reaction necessitates the use of a coupling reagent, for example any of the type of coupling reagents commonly employed in the synthesis of peptides. Examples of such coupling reagents include the carbodiimides such as N,N'-dicyclohexylcarbodiimide, N,N'-diisopropylcarbodiimide, or N,N'-diethylcarbodiimide; the imidazoles such as carbonylimidazole; as well as reagents such as N-ethoxycarbonyl-2-ethoxy-1,2-dihydroquinoline (EEDQ). The direct coupling of a substituted benzoic acid and an aryl amine is carried out by combining about equimolar quantities of the starting materials in the presence of an equimolar quantity or slight excess of coupling reagent. The reaction generally is carried out in an unreactive organic solvent such as dichloromethane or dimethylformamide, and usually is complete within about twenty-four hours when conducted at a temperature of about 0° to about 30° C. The benzamide product is readily isolated and purified by standard procedures.

Thiobenzamides defined by the above general formula wherein Z is sulfur form another important group of compounds that are herbicidally active and are a further embodiment of this invention. The thiobenzamides of the invention are preferably prepared by thiating the corresponding benzamides according to the following scheme:

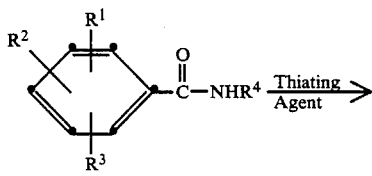

-continued

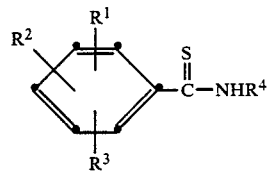

Any of several thiating agents can be employed in the thiation reaction, including phosphorus pentasulfide. An especially preferred thiating agent is Lawesson's Reagent, which is [2,4-bis(4-methoxyphenyl)-1,3-dithia-2,4-diphosphetane-2,4-disulfide. This thiating reagent and its general use are described in detail in *Tetrahedron Letters*, 22, 4061 (1980). The thiation reaction is preferably carried out by reacting approximately equimolar quantities of a benzamide and Lawesson's Reagent in a mutual organic solvent such as toluene or dioxane. The reaction generally is complete within about two to ten hours when carried out at a temperature of about 50° to about 150° C. The thiobenzamide that is formed can be isolated and purified by normal methods, including chromatography and the like.

A further embodiment of the present invention are the agronomically acceptable salts of the benzamides defined by the above general formula. Such salts may be particularly preferred when it is desired to increase the water solubility of the benzamides, since the agronomically acceptable salts are in general highly soluble in water and similar polar solvents. Typical salts provided herein are prepared by reaction of a benzamide with a strong base such as sodium hydride, lithium hydride or potassium hydride, generally in a solvent such as diethyl ether or the like. Sodium salts are preferred salt forms for the benzamides of this invention. All of the alkali metal salts are agronomically acceptable.

The preparation of the benzamides of this invention requires the use of starting materials which are either known or are readily preparable by methods familiar to those in the art. Most of the substituted benzoic acids which are required are commercially available. The reactive derivatives of such benzoic acids are prepared by routine procedures. For example, a preferred synthetic method according to this invention requires the use of substituted benzoic acid halides or mixed anhydrides. The acid halides are prepared by reaction of a benzoic acid with a halogenating agent such as oxalyl chloride, thionyl chloride, phosphorus trichloride or phosphorus tribromide.

The benzoic acid anhydrides which can be condensed with an amine to form a benzamide can be made by reacting a benzoic acid alkali metal salt, for example a sodium or potassium salt, with an acid halide such as benzoyl chloride or acetyl bromide.

Benzoic acid derivatives which are commonly employed in the synthesis of the benzamides of this invention include the following:
2,6-dimethoxybenzoyl chloride;
2,6-dimethoxybenzoyl formic anhydride;
2,6-diethoxybenzoyl bromide;
2,6-di-n-propoxybenzoyl iodide;
2,6-di-isopropoxybenzoyl bromide;
2-methoxy-6-n-propoxybenzoyl chloride;
2-methoxy-3-ethoxybenzoyl bromide;
3-ethoxy-5-n-propoxybenzoyl acetic anhydride;
2,4,6-triethylbenzoyl bromide;
3,5-di-n-butylbenzoyl chloride;

2-methoxy-6-chlorobenzoyl bromide;
2,6-di-n-propoxybenzoyl acetic anhydride;
2-methoxy-6-fluorobenzoyl bromide;
2,6-dimethoxy-4-trifluoromethylbenzoyl chloride;
2,6-diethylbenzoyl iodide;
2,4,6-trimethoxybenzoyl chloride;
2-methoxy-6-ethylthiobenzoyl bromide;
2-methoxy-6-ethyl-4-trifluoromethyl benzoyl bromide, and the like.

The aryl amines of the formula $H_2NR^4$ which are required as starting materials are either readily available commercially or are preparable by art-recognized procedures. For example, 3-substituted-5-aminoisoxazoles can be prepared by reaction of a suitable carboxylic acid ester such as $R^5COOCH_3$ with acetonitrile and a strong base such as sodium hydride, followed by reaction with hydroxylamine according to the following scheme:

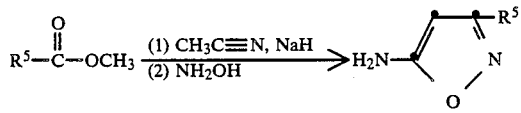

Similarly, 5-substituted-3-amino-isoxazoles can be prepared by iminoether formation with a suitably substituted β-ketonitrile followed by treatment with hydroxylamine to form an iminium salt, and finally reaction with a protonic acid according to the following general scheme:

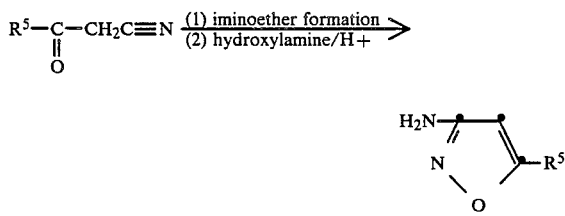

The thiadiazole amines which are required as starting materials can be prepared by reaction of a carboxylic acid halide with thiosemicarbazide as follows:

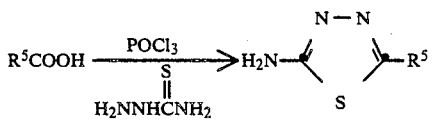

Similarly, pyrazole amines can be synthesized by reacting hydrazine with a suitably substituted β-keto nitrile according to the following scheme:

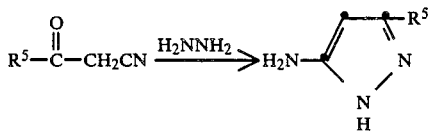

Hydrazine is also utilized in the synthesis of triazole derivatives according to the following path:

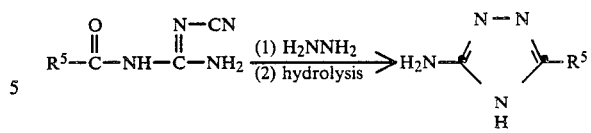

Imidazolyl amines can be prepared by reacting cyanamide with an aminomethyl ketone according to the following scheme:

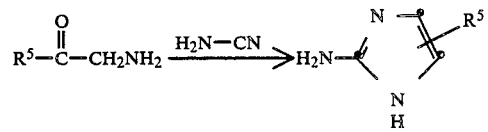

Aminomethyl ketones also are reacted with ammonia, hydrogen sulfide and hydrogen peroxide to give amino isothiazoles:

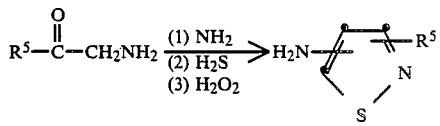

Amino oxadiazoles are readily prepared by reaction of an amide oxime with trichloroacetic anhydride fokllowed by treatment with ammonia:

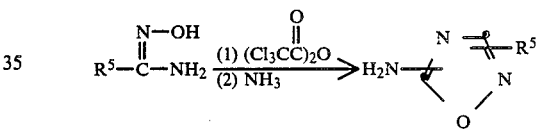

Amino pyridazines are prepared by reaction of ammonia with a suitably substituted halopyridazine according to the following scheme:

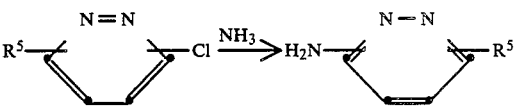

These and other synthetic paths leading to aryl amines of the formula $H_2NR^4$ are well known to those skilled in the art of organic chemistry.

As already pointed out, preferred aryl substituents defined in the above general formula by $R^4$ include 3-isoxazolyl, 5-isoxazolyl and 1,3,4-thiadiazol-2-yl. Typical examples of isoxazolyl amines and thiadiazolyl amines which are employed as starting materials to be acylated with a benzoic acid derivative include the following:
3-tert.-butyl-5-aminoisoxazole;
3-(1,1-dimethylpentyl)-5-aminoisoxazole;
3-(1,1-diethyl-4-ethoxybutyl)-5-aminoisoxazole;
3-(1-ethylcyclohexyl)-5-aminoisoxazole;
3-(1,2-diethyl-5-hexenyl)-5-aminoisoxazole;
3-(2,2-di-n-propyl-4-cycloheptylbutyl)-5-aminoisoxazole;
3-[1,1-dimethyl-3-(4-phenylbutoxy)propyl]-5-aminoisoxazole;
3-(1,1-diethyl-5-cyclohexylpentyl)-5-aminoisoxazole;

3-(1-n-butyl-2,3-dichlorocyclopropyl)-5-aminoisoxazole;
3-amino-5-(1,1-diethylheptyl)isoxazole;
3-amino-5-(1-isopropyl-3-cyclohexylpropyl)isoxazole;
3-amino-5-(1,1-dimethyl-6-heptenyl)isoxazole;
3-amino-5-[1,1-diethyl-3-(2,6-dibromophenyl)propyl]isoxazole;
3-amino-5-(1,1-di-n-propyl-6-iodohexyl)isoxazole;
3-amino-5-(1,2-dimethyl-3-ethylthiopropyl)isoxazole;
3-amino-5-(2,3-dimethyl-5-isobutoxypentyl)isoxazole;
3-amino-5-(1,4-dimethyl-2,2,3-triethyl-5-bromopentyl)isoxazole;
2-amino-5-tert.-butyl-1,3,4-thiadiazole;
2-amino-5-(1-ethyl-1-methylpropyl)-1,3,4-thiadiazole;
3-amino-4-methyl-5-(1,1-dimethylpropyl)isoxazole;
3-(methyl-1-methylthiomethyl-3-methoxypropyl)-4-n-butyl-5-aminoisoxazole;
3-amino-4-isobutyl-5-(2-ethyl-1,3-dioxan-2-yl)isoxazole;
2-amino-5-(1-methyl-1-methylthiomethyl-3-ethoxypropyl)-1,3,4-thiadiazole;
2-amino-5-(2-ethyl-1,3-dioxan-2-yl)-1,3,4-thiadiazole;
2-amino-5-(1,1-dimethyl-3-phenoxypropyl)-1,3,4-thiadiazole;
2-amino-5-(1,1-diethyl-5-ethylthiopentyl)-1,3,4-thiadiazole;
2-amino-5-[2,2-di-n-propyl-4-(2-methylphenoxy)butyl]-1,3,4-thiadiazole;
2-amino-5-(1-ethyl-3-isopropyl-4-chlorocyclopentyl)-1,3,4-thiadiazole;
2-amino-5-(2-n-propyl-3-methyl-5-tert.-butylthiopentyl)-1,3,4-thiadiazole;
2-amino-5-(1,1-dimethyl-3-iodopropyl)-1,3,4-thiadiazole;
2-amino-5-(1,1-di-n-propyldecyl)-1,3,4-thiadiazole;
2-amino-5-(1,1-diethyl-6-heptynyl)-1,3,4-thiadiazole;

Additional aryl amines which can be employed in the synthesis of the benzamide herbicides of this invention include oxadiazoles, triazoles, isothiazoles, imidazoles, pyrazoles, and pyridazines. Illustrative of the such commonly used aryl amines are:
2-amino-5-(1-ethyl-1-methylpropyl)-1,3,4-oxadiazole;
2-amino-5-tert.-butyl-1,3,4-oxadiazole;
2-amino-5-(1,1-dimethyl-6-isopropoxyhexyl)-1,3,4-oxadiazole;
5-amino-3-(1-n-propylcycloheptyl)-1,2,4-oxadiazole;
3-amino-5-(1,1-dimethyl-3-ethyl-4-methylthiobutyl)-1,2,4-oxadiazole;
2-amino-5-[1,1-di-n-propyl-3-(4-bromophenyl)propyl]-1,3,4-oxadiazole;
2-amino-1,3,4-triazole;
5-amino-4-(1-ethyl-1-methylpropyl)-1,2,3-oxadiazole;
4-amino-5-(1-ethyl-1-cyclopropylmethyl-2-phenyl)-1,2,3-thiadiazole;
5-amine-4-(1-methyl-1-methoxymethyl-2-methylthioethyl)-1,2,3-triazole;
3-amino-5-tert.-butyl-1,2,4-triazole;
2-amino-5-(1,1-diethylhexyl)-1,3,4-triazole;
2-amino-5-(1-n-propyl-2,2-dibromocyclopropyl)-1,3,4-triazole;
3-amino-5-(1,1-diethyl-4-fluorobutyl)-1,2,4-triazole;
2-amino-5-(1,1-dimethyl-2,2-diethyl-3-n-propyl-4-pentenyl)-1,3,4-triazole;
3-amino-5-(1,1-diethylpropyl)-1,2,4-thiadiazole;
5-amino-3-[1-(2-butynyl)cyclohexyl]-1,2,4-oxadiazole;
5-amine-2-(1,1-dimethyl-3-chloropropyl)-1,3,4-oxadiazole;
3-amine-5-(1,1-diethylheptyl)-1,2,4-oxadiazole;

2-amino-5-(1-ethyl-1-methyl-6-n-butylthiohexyl)-1,3,4-triazole;
5-amino-3-(1,1-diethyl-2-methylhexyl)isothiazole;
5-amino-3-tert.-butylisothiazole;
5-amino-3-(1-n-propylcycloheptyl)isothiazole;
5-amino-3-[1,1-diethyl-4-(3-methylcyclopentyl)butyl]isothiazole;
3-amino-5-(1,1-diethylhexyl)isothiazole;
3-amino-5-[1-ethyl-2-methyl-4-(3-phenoxypropyl)octyl]isothiazole;
3-amino-5-(1,2,3-trimethyl-5-chloroheptyl)isothiazole;
3-amino-5-(1,1-diethyl-5-n-butylthiopentyl)isothiazole;
5-amino-3-(1,1-di-n-propylhexyl)pyrazole;
5-amino-3-tert.-butylpyrazole;
5- amino-3-(1-ethyl-1-methylpropyl)pyrazole;
5-amino-3-(1,1-diethyl-4-pentenyl)pyrazole;
5-amino-3-[1,1-dimethyl-4-(3-phenylpropoxy)butyl]pyrazole;
5-amino-3-(2,2-diethyldecyl)pyrazole;
3-amino-5-(1-ethyl-4,4-dimethyl-5-chloropentyl)pyrazole;
3-amino-5-(1-ethyl-1-methylpropyl)pyrazole;
3-amino-5-(1,1-dimethyl-6-n-butoxyphenyl)pyrazole;
2-amino-5-(1-ethyl-1-methylpropyl)-imidazole;
2-amino-5-[1-(2-propenyl)-1-(2-propynyl)-4-hexenyl]imidazole;
2-amino-5-[1-ethyl-4-phenylbutyl)imidazole;
3-amino-5-(1,1-dibutylhexyl)pyrazole;
3-amino-5-(1,1-diethyl-4-cyclohexylbutyl)pyrazole;
3-amino-6-(1-ethyl-1-methylpropyl)pyridazine; and
3-amino-6-(1-ethylcyclohexyl)pyridazine.

A particularly preferred class of benzamides provided by this invention is represented by the formula

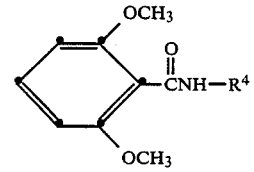

in which $R^4$ is

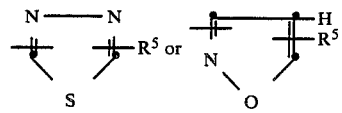

and wherein $R^5$ is

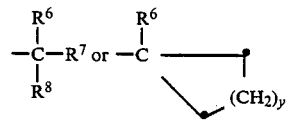

in which $R^6$ is $C_1$–$C_4$ alkyl, $R^7$ is hydrogen or $C_1$–$C_4$ alkyl, $R^8$ is $C_1$–$C_{13}$ alkyl and y is an integer from zero to four.

Among the most preferred compounds falling within this preferred class are:
N-[3-(1-ethyl-1-methylpropyl)-5-isoxazolyl]-2,6-dimethoxybenzamide;
N-[3-(tert.-butyl)-5-isoxazolyl]-2,6-dimethoxybenzamide;

N-[5-(1-ethyl-1-methylpropyl)-1,2,4-thiadiazol-2-yl]-2,6-dimethoxybenzamide;
N-[5-(1,1-diethylpropyl)-1,3,4-thiadiazol-2-yl]-2,6-dimethoxybenzamide;
N-[3-(1,1-dimethylpropyl)-5-isoxazolyl]-2,6-dimethoxybenzamide;
N-[3-(1,1-diethylhexyl)-5-isoxazolyl]-2,6-dimethoxybenzamide;
N-[5-(1-ethylheptyl)-1,3,4-thiadiazol-2-yl]-2,6-dimethoxybenzamide;
N-[3-(1,1-diethylheptyl)-5-isoxazolyl]-2,6-dimethoxybenzamide;
N-[3-(1-ethyl-1-methylbutyl)-5-isoxazolyl]-2,6-dimethoxybenzamide;
N-[3-(1,1-diethylbutyl)-5-isoxazolyl]-2,6-dimethoxybenzamide;
N-[5-(1-methylbutyl)-1,3,4-thiadiazol-2-yl]-2,6-dimethoxybenzamide;
N-[5-(1-ethyl-1-methylhexyl)-1,3,4-thiadiazol-2-yl]-2,6-dimethoxybenzamide;
N-[3-(1,1-dimethyltetradecyl)-5-isoxazolyl]-2,6-dimethoxybenzamide;
N-[5-(1,2-dimethylbutyl)-1,3,4-thiadiazol-2-yl]-2,6-dimethoxybenzamide;
N-[5-(1,1-diethylhexyl)-3-isoxazolyl]-2,6-dimethoxybenzamide;
N-[5-(1,1,2-trimethylbutyl)-1,3,4-thiadiazol-2-yl]-2,6-dimethoxybenzamide;
N-[3-(1,1,2,2-tetramethylbutyl)-5-isoxazolyl]-2,6-dimethoxybenzamide;
N-[3-(1-ethylhexyl)-5-isoxazolyl]-2,6-dimethoxybenzamide;
N-[5-(1-ethyl-1-methylpentyl)-3-isoxazolyl]-2,6-dimethoxybenzamide;
N-[5-(1,1-diethyldecyl)-1,3,4-thiadiazol-2-yl]-2,6-dimethoxybenzamide;
N-5-(1-isopropylcyclohexyl)-3-isoxazolyl]-2,6-dimethoxybenzamide;
N-[5-(1-methylcyclopropyl)-1,3,4-thiadiazol-2-yl]-2,6-dimethoxybenzamide;
N-[5-(1-ethylcycloheptyl)-1,3,4-thiadiazol-2-yl]-2,6-dimethoxybenzamide;
N-[3-(1-isopropylcyclopentyl)-5-isoxazolyl]-2,6-dimethoxybenzamide;

Another especially preferred class of benzamides provided by this invention are those of the formula

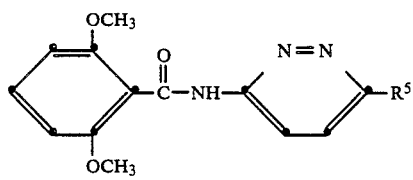

wherein $R^5$ is

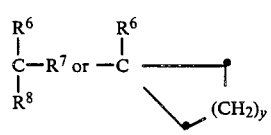

in which $R^6$ is $C_1$–$C_4$ alkyl, $R^7$ is hydrogen or $C_1$–$C_4$ alkyl, $R^8$ is $C_1$–$C_{13}$ alkyl, and y is an integer from zero to four.

Among the most preferred compounds falling within this preferred class are:
N-[6-(1-ethyl-1-methylpropyl)-pyridazin-3-yl]-2,6-dimethoxybenzamide;
N-[6-(1,1-dimethylethyl)-pyridazin-3-yl]-2,6-dimethoxybenzamide;
N-[6-(1-ethyl-1-methyldecyl)-pyridazin-3-yl]-2,6-dimethoxybenzamide;
N-[6-(1-n-butyloctyl)-pyridazin-3-yl]-2,6-dimethoxybenzamide;
N-[6-(1-methylethyl)-pyridazin-3-yl]-2,6-dimethoxybenzamide;
N-[6-(1-ethylcyclohexyl)-pyridazin-3-yl]-2,6-dimethoxybenzamide;
N-[6-(1-methylcyclobutyl)-pyradazin-3-yl]-2,6-dimethoxybenzamide;

Other specific compounds embraced by this invention include:
N-[5-(1,1-diethyl-2-methylthioethyl)-1,3,4-thiadiazol-2-yl]-2,6-diethoxybenzamide;
N-[5-(1-ethyl-1-methylpropyl)-1,2,3-thiadiazol-4-yl]-2,6-dimethoxybenzamide;
N-[5-(1-ethylcyclohexyl)-1,2,3-thiadiazol-4-yl]-2,6-dimethoxybenzamide;
N-[5-(2,2-diethylbutyl)-1,3,4-thiadiazol-2-yl]-2,6-diethoxybenzamide;
N-[5-(1,2-diethyl-3-isopropoxypropyl)-1,3,4-thiadiazol-2-yl]-2,6-dimethoxybenzamide;
N-[3-(1,1-dimethyl-2-cycloheptylethyl)-5-isoxazolyl]-2,6-di-n-propoxybenzamide;
N-[3-(2,2-diethylhexyl)-5-isoxazolyl[-2,6-dimethoxybenzamide;
N-[5-(1,1-diethyl-2-phenylethyl)-1,3,4-thiadiazol-2-yl]-2,6-dimethoxybenzamide;
N-[3-(1,1-diethylhexyl)-5-isoxazolyl]-2,6-diethoxybenzamide;
N-[5-(1,1-diethyl-5-fluoropentyl)-1,3,4-thiadiazol-2-yl]-2,6-di-n-propoxybenzamide;
N-[3-(1,1-diethyl-2-methoxyethyl)-5-isoxazolyl]-2,6-dimethoxybenzamide;
N-[5-(1,1-diethylpentyl)-4H-1,2,4-triazol-3-yl)-2,6-methoxybenzamide;
N-[5-(1-ethyl-1-methylbutyl)-1,3,4-thiadiazol-2-yl]-2,6-diethylbenzamide;
N-[3-(1-ethyl-1-phenylethyl)-5-isoxazolyl]-2,6-diethoxybenzamide;
N-[5-(1-ethyl-1-methyl-3-chloropropyl)-1,3,4-thiadiazol-2-yl]-4-methoxybenzamide;
N-[5-(1-ethyl-1-methyl-3-methoxypropyl)-1,3,4-thiadiazol-2-yl]-2,4,6-triethoxybenzamide;
N-[3-(1-methyl-1-benzyloxyethyl)-5-isoxazolyl]-2,6-dimethoxybenzamide;
N-[3-(1,1-di-n-propyl-5-phenylpentyl)-5-isoxazolyl]-2,6-diethoxybenzamide;
N-[4-(1,1-diethylpentyl)-1,2,3-oxadiazol-5-yl]-2,6-dimethoxybenzamide;
N-[5-(1-ethyl-1-acetoxymethyl-3-methoxypropyl)-1,2,3-oxadiazol-4-yl]-2,6-dimethoxybenzamide;
N-[5-(1-ethyl-1-butylhexyl)-1,2,3-triazol-4-yl]-2,6-dimethoxybenzamide;
N-[4-(1-ethyl-2-phenoxyethyl)-1,2,3-triazol-5-yl]-2,6-dimethoxybenzamide;
N-[5-(1-ethylcyclobutyl)-1,3,4-thiadiazol-2-yl]-2,6-diethoxybenzamide;
N-[3-(1,1-diethyl-3-butenyl)-5-isoxazolyl]-2,6-diethoxybenzamide;
N-[5-(1-methylcyclopropyl)-1,3,4-thiadiazol-2-yl]-2,6-diethoxybenzamide;

N-[5-(1-ethylcycloheptyl)-1,3,4-thiadiazol-2-yl]-2,6-di-n-propoxybenzamide;
N-[3-(1,1-diethyl-5-chloropentyl)-5-isoxazolyl]-2,6-dimethoxybenzamide;
N-[3-(1-n-propylcyclobutyl)-5-isoxazolyl]-2,6-diethoxybenzamide;
N-[3-(1-isopropylcyclopentyl)-5-isoxazolyl]-2-ethylthio-6-methoxybenzamide;
N-[3-(2-methyl-3-(2-methyl-1-propenyl)cyclobutyl)-5-isoxazolyl]-2,6-diethoxybenzamide;
N-[5-(1,1-dimethyl-3-pentenyl)-1,3,4-thiadiazol-2-yl]-2-methoxy-6-n-propoxybenzamide;
N-[3-(1,1-dimethylpropyl)-1H-pyrazol-5-yl]-2,6-diethoxybenzamide;
N-[3-(1-ethyl-1-methylpropyl)-5-isoxazolyl]-2-fluoro-6-ethoxybenzamide;
N-[3-(1,1-di-n-propylpentyl)-1H-pyrazol-5-yl-2-methoxy-6-ethoxybenzamide;
N-[5-(1,1-dimethylpropyl)-1,3,4-thiadiazol-2-yl]benzamide;
N-[5-(1-ethylcyclopentyl)-1,3,4-thiadiazol-2-yl]-2,6-diethoxybenzamide;
N-[5-(1-methyl-1-n-propylpentyl)-1,3,4-thiadiazol-2-yl]-2-methyl-6-methylthiobenzamide;
N-[5-(1-ethylcycloheptyl)-4-ethyl-3-isoxazolyl]-2,6-dimethoxybenzamide;
N-[3-(1,1-dimethylheptyl)-4-methyl-5-isoxazolyl]-2,6-diethoxybenzamide;
N-[3-(1-ethyl-1-methylbutyl)-5-isoxazolyl]-2-bromo-6-methoxybenzamide;
N-[5-(1-ethyl-1-methyldecyl)-1,2,4-thiadiazol-2-yl]-2,6-dimethoxy-4-trifluoromethylbenzamide;
N-[3-(tert.-butyl)-5-isothiazolyl]-2,6-diethoxybenzamide;
N-[3-(1,1-diethylpentyl)-5-isoxazolyl]-2,4,6-trimethylbenzamide;
N-[3-(1,1-diethylhexyl)-5-isoxazolyl]-4-iodobenzamide;
N-[3-(1,2,2-trimethyl-1-ethylpropyl)-1,2,4-thiadiazol-5-yl]-3-ethylthio-6-methoxybenzamide;
N-[3-(1-ethyl-1-methylpropyl)-1,2,4-thiadiazol-5-yl]-2,6-di-n-propoxybenzamide;
N-[3-(1-ethyl-1-n-propylhexyl)-1,2,4-oxadiazol-5-yl]-2,6-diethoxybenzamide;
N-[3-(1-ethylcycloheptyl)-1,2,4-oxadiazol-5-yl]-2,4,5-trimethoxybenzamide;
N-[3-(1-ethyl-3-phenylpropyl)-1,2,4-oxadiazol-5-yl]-2,6-di(methylthio)benzamide;
N-[3-(1-methyl-1-ethyl-3-hexynyl)-1,2,4-oxadiazol-5-yl]-2,6-dimethoxybenzamide;
N-[5(4)-(1-ethyl-1-methylpropyl)-2-imidazolyl]-2,6-dimethoxybenzamide;
N-[5(4)-(1,1-dimethyl-5-phenylpentyl)-2-imidazolyl]-2,6-di(ethylthio)benzamide;
N-[5(4)-(2,2-diethyl-2-cyclobutylethyl)2-imidazolyl]-2,6-dimethoxy-4-(trifluoromethyl)benzamide;
N-[5(4)-(1-(3-butenyl)cyclohexyl)-2-imidazolyl]-2-chloro-4-methoxy-6-ethoxybenzamide;
N-[5-(1,1-dimethylpentyl)-4-ethyl-2-imidazolyl]-2,6-diethoxybenzamide;
N-[6-(1-methyl-1-acetoxymethyl-3-phenoxypropyl)-4-methyl-pyridazin-3-yl]-2,6-dimethoxybenzamide;
N-[6-(1-ethyl-1,3-dithian-2-yl)-5-isopropylpyridazin-3-yl]-2,6-dimethoxybenzamide;
N-[6-(1-methylcyclooctyl)pyridazin-3-yl]-2,6-dimethoxybenzamide;
N-[6-(5-ethyl-1,3-dioxan-5-yl)pyridazin-3-yl]-2,6-diethoxybenzamide;
N-[6-(1-ethyl-1-methylpropyl)pyridazin-3-yl]-2,6di-n-propoxybenzamide;
N-[6-(1-ethyl-3-cycloheptylpropyl)pyridazin-3-yl]-2,6-di-n-butoxybenzamide; and the like.

Thiobenzamides defined by the above general formula wherein Z is sulfur also form an important class of compounds provided by this invention and are exemplified by the following:
N-[3-(1-ethyl-1-methylpropyl)-5-isoxazolyl]-2,6-dimethoxythiobenzamide;
N-[3-(tert.-butyl)-5-isoxazolyl]-2,6-dimethoxythiobenzamide;
N-[5-(1-ethyl-1-methylpropyl)-1,3,4-thiadiazol-2-yl]-2,6-dimethoxythiobenzamide;
N-[5-(1,1-diethylpropyl)-1,3,4-thiadiazol-2-yl]-2,6-dimethoxythiobenzamide;
N-[3-(1,1-dimethylpropyl)-5-isoxazolyl]-2,6-dimethoxythiobenzamide;
N-[3-(1,1-diethylhexyl)-5-isoxazolyl]-2,6-dimethoxythiobenzamide;
N-[5-(1-ethylheptyl)-1,3,4-thiadiazol-2-yl]-2,6-dimethoxythiobenzamide;
N-[3-(1,1-diethylheptyl)-5-isoxazolyl]-2,6-dimethoxythiobenzamide;
N-[3-(1-ethyl-1-methylbutyl)-5-isoxazolyl]-2,6-dimethoxythiobenzamide;
N-[3-(1,1-diethylbutyl)-5-isoxazolyl]-2,6-dimethoxythiobenzamide;
N-[5-(1-methylbutyl)-1,3,4-thiadiazol-2-yl]-2,6-dimethoxythiobenzamide;
N-[5-(1-ethyl-1-methylhexyl)-1,3,4-thiadiazol-2-yl]-2,6-dimethoxythiobenzamide;
N-[3-(1,1-dimethyltetradecyl)-5-isoxazolyl]-2,6-dimethoxythiobenzamide;
N-[5-(1,2-dimethylbutyl)-1,3,4-thiadiazol-2-yl]-2,6-dimethoxythiobenzamide;
N-[5-(1,1-diethylhexyl)-3-isoxazolyl]-2,6-dimethoxythiobenzamide;
N-[5-(1,1,2-trimethylbutyl)-1,3,4-thiadiazol-2-yl]-2,6-dimethoxythiobenzamide;
N-[3-(1,1,2,2-tetramethylbutyl)-5-isoxazolyl]-2,6-dimethoxythiobenzamide;
N-[3-(1-ethylhexyl)-5-isoxazolyl]-2,6-dimethoxythiobenzamide;
N-[5-(1-ethyl-1-methylpentyl)-3-isoxazolyl]-2,6-dimethoxythiobenzamide;
N-[5-(1,1-diethyldecyl)-1,3,4-thiadiazol-2-yl]-2,6-dimethoxythiobenzamide;
N-5-(1-isopropylcyclohexyl)-3-isoxazolyl]-2,6-dimethoxythiobenzamide;
N-[5-(1-methylcyclopropyl)-1,3,4-thiadiazol-2-yl]-2,6-dimethoxythiobenzamide;
N-[5-(1-ethylcycloheptyl)-1,3,4-thiadiazol-2-yl]-2,6-dimethoxythiobenzamide;
N-[3-(1-isopropylcyclopentyl)-5-isoxazolyl]-2,6-dimethoxythiobenzamide;
N-[5-(1,1-diethyl-2-methylthioethyl)-1,3,4-thiadiazol-2-yl]-2,6-diethoxythiobenzamide;
N-[6-(1-ethyl-1-methylpropyl)-pyridazin-3-yl]-2,6-dimethoxythiobenzamide;
N-[6-(1,1-dimethylethyl)-pyridazin-3-yl]-2,6-dimethoxythiobenzamide;
N-[6-(1-n-butyloctyl)-pyridazin-3-yl]-2,6-dimethoxythiobenzamide;
N-[6-(1-methylethyl)-pyridazin-3-yl]-2,6-dimethoxythiobenzamide;
N-[6-(1-ethylcyclobenzyl)-pyridazin-3-yl]-2,6-dimethoxythiobenzamide;

N-[6-(1-methylcyclobutyl)-pyradazin-3-yl]-2,6-dimethoxythiobenzamide;
N-[5-(2,2-diethylbutyl)-1,3,4-thiadiazol-2-yl]-2,6-diethoxythiobenzamide;
N-[5-(1,2-diethyl-3-isopropoxypropyl]-1,3,4-thiadiazol-2-yl]-2,6-dimethoxythiobenzamide;
N-[3-(1,1-dimethyl-2-cycloheptylethyl)-5-isoxazolyl]-2,6-di-n-propoxythiobenzamide;
N-[3-(2,2-diethylhexyl)-5-isoxazolyl]-2,6-dimethoxythiobenzamide;
N-[5-(1,1-diethyl-2-phenylethyl)-1,3,4-thiadiazol-2-yl]-2,6-dimethoxythiobenzamide;
N-[3-(1,1-diethylhexyl)-5-isoxazolyl]-2,6-diethoxythiobenzamide;
N-[5-(1,1-diethyl-5-fluoropentyl]-1,3,4-thiadiazol-2-yl]-2,6-di-n-propoxythiobenzamide;
N-[3-(1,1-diethyl-2-methoxyethyl)-5-isoxazolyl]-2,6-dimethoxythiobenzamide;
N-[5-(1,1-diethylpentyl)-4H-1,2,4-triazol-3-yl)-2,6-dimethoxythiobenzamide;
N-[5-(1-ethyl-1-methylbutyl)-1,3,4-thiadiazol-2-yl]-2,6-diethylthiobenzamide;
N-[3-(1-ethyl-1-phenylethyl)-5-isoxazolyl]-2,6-diethoxythiobenzamide;
N-[5-(1-ethyl-1-methyl-3-chloropropyl)-1,3,4-thiadiazol-2-yl]-4-methoxythiobenzamide;
N-[5-(1-ethyl-1-methyl-3-methoxypropyl)-1,3,4-thiadiazol-2-yl]-2,4,6-triethoxythiobenzamide;
N-[3-(1-methyl-1-benzyloxyethyl)-5-isoxazolyl]-2,6-dimethoxythiobenzamide;
N-[3-(1,1-di-n-propyl-5-phenylpentyl)-5-isoxazolyl]-2,6-diethoxythiobenzamide;
N-[5-(1-ethylcyclobutyl)-1,3,4-thiadiazol-2-yl]-2,6-diethoxythiobenzamide;
N-[3-(1,1-diethyl-3-butenyl)-5-isoxazolyl]-2,6-diethoxythiobenzamide;
N-[5-(1-methylcyclopropyl)-1,3,4-thiadiazol-2-yl]-2,6-diethoxythiobenzamide;
N-[5-(1-ethylcycloheptyl)-1,3,4-thiadiazol-2-yl]-2,6-di-n-propoxythiobenzamide;
N-[3-(1,1-diethyl-5-chloropentyl)-5-isoxazolyl]-2,6-dimethoxythiobenzamide;
N-[3-(1-n-propylcyclobutyl)-5-isoxazolyl]-2,6-diethoxythiobenzamide;
N-[3-(1-isopropylcyclopentyl)-5-isoxazolyl]-2-ethylthio-6-methoxythiobenzamide;
N-[3-(2-methyl-3-(2-methyl-1-propenyl)cyclobutyl)-5-isoxazolyl]-2,6-diethoxythiobenzamide;
N-[5-(1,1-dimethyl-3-pentenyl)-1,3,4-thiadiazol-2-yl]-2-methoxy-6-n-propoxythiobenzamide;
N-[3-(1,1-dimethylpropyl)-1H-pyrazol-5-yl]-2,6-diethoxythiobenzamide;
N-[3-(1-ethyl-1-methylpropyl)-5-isoxazolyl]-2fluoro-6-ethoxythiobenzamide;
N-[3-(1,1-di-n-propylpentyl)-1H-pyrazol-5-yl-2-methoxy-6-ethoxythiobenzamide;
N-[5-(1,1-dimethylpropyl)-1,3,4-thiadiazol-2-yl]thiobenzamide;
N-[5-(1-ethylcyclopentyl)-1,3,4-thiadiazol-2-yl]-2,6-diethoxythiobenzamide;
N-[5-(1-methyl-1-n-propylpentyl)-1,3,4-thiadiazol-2-yl]-2-methyl-6-(methylthio)thiobenzamide;
N-[3-(1-ethyl-1-methylbutyl)-5-isoxazolyl]-2bromo-6-methoxythiobenzamide;
N-[5-(1-ethyl-1-methyldecyl)-1,2,4-thiadiazol-2-yl]-2,6-dimethoxy-4-trifluoromethylthiobenzamide;
N-[3-(tert.-butyl)-5-isothiazolyl]-2,6-diethoxybenzamide;
N-[3-(1,1-diethylpentyl)-5-isoxazolyl]-2,4,6-trimethylthiobenzamide;
N-[3-(1,1-diethylhexyl)-5-isoxazolyl]-4-iodothiobenzamide;
N-[3-(1,2,2-trimethyl-1-ethylpropyl)-1,2,4-thiadiazol-5-yl]-3-ethylthio-6-methoxythiobenzamide;
N-[3-(1-ethyl-1-methylpropyl)-1,2,4-thiadiazol-5-yl]-2,6-di-n-propoxythiobenzamide;
N-[3-(1-ethyl-1-n-propylhexyl)-1,2,4-oxadiazol-5-yl]-2,6-diethoxythiobenzamide;
N-[3-(1-ethylcycloheptyl)-1,2,4-oxadiazol-5-yl]-2,4,5-trimethoxythiobenzamide;
N-[3-(1-ethyl-3-phenylpropyl)-1,2,4-oxadiazol-5-yl]-2,6-di(methylthio)thiobenzamide;
N-[3-(1-methyl-1-ethyl-3-hexynyl)-1,2,4-oxadiazol-5-yl]-2,6-dimethoxythiobenzamide;
N-[5(4)-(1-ethyl-1-methylpropyl)-2-imidazolyl]-2,6-dimethoxythiobenzamide;
N-[5(4)-(1,1-dimethyl-5-phenylpentyl)-2-imidazolyl]-2,6-di(ethylthio)thiobenzamide;
N-[5(4)-(2,2-diethyl-2-cyclobutylethyl)2-imidazolyl]-2,6-dimethoxy-4-(trifluoromethyl)thiobenzamide;
N-[5-(4)-(1-(3-butenyl)cyclohexyl)-2-imidazolyl]-2-chloro-4-methoxy-6-ethoxythiobenzamide;
N-[6-(1-ethyl-1-methylpropyl)pyridazin-3-yl]-2,6-di-n-propoxythiobenzamide;
N-[6-(1-ethyl-3-cycloheptylpropyl)pyridazin-3-yl]-2,6-di-n-butoxythiobenzamide; and the like.

The preparation of various benzamides provided by the invention is illustrated by the following detailed examples. The exemplification is not exhaustive of the compounds embraced by the invention nor of the possible synthetic routes, and should not be so construed.

EXAMPLE 1

N-[3-(1-Ethyl-1-methylpropyl)-5-isoxazolyl]-2,6-dimethoxybenzamide (A)

Preparation of 5-amino-3-(1-ethyl-1-methylpropyl)isoxazole

A 16.5 Kg portion of methyl 2-ethylbutyrate was reacted with 60 Kg of n-butyl lithium, diisopropylamine, and 19.1 Kg of methyl iodide to provide 17.4 Kg of methyl 2-ethyl-2-methylbutyrate. A 7.5 Kg portion of the ester thus formed was reacted with 3.25 Kg of acetonitrile and 5.03 g of sodium hydride in 33 liters of tetrahydrofuran to provide 1-ethyl-1-methylpropyl cyanomethyl ketone. The ketone thus formed was reacted with 4.35 Kg of hydroxylamine hydrochloride and 2.54 Kg of sodium hydroxide in 44 liters of water to provide 5.65 Kg of 5-amino-3-(1-ethyl-1-methylpropyl)isoxazole.

(B)

Preparation of 2,6-dimethoxybenzoyl chloride

A 8.5 Kg portion of 2,6-dimethoxybenzoic acid was dissolved in 60 liters of toluene and the solution was stirred at ambient temperature while 6.8 liters of thionyl chloride was added dropwise over forty-five minutes. Following the addition, the reaction mixture next was cooled to room temperature and the solvent was removed by evaporation under reduced pressure, washed with 25 liters of Pet. ether cooled and filtered to provide a crude solid product. The product was stirred for one hour with 25 liters of fresh Pet. ether, and then cooled to 10° C. and filtered to provide 8.94 Kg of 2,6-dimethoxybenzoyl chloride.

(C)

Synthesis of N-[3-(1-ethyl-1-methylpropyl)-5-isoxazolyl]-2,6-dimethoxybenzamide

To a stirred solution of 3.36 Kg of 5-amino-3-(1-ethyl-1-methylpropyl)isoxazole in 65 liters of toluene was added portion-wise over thirty minutes 4.015 Kg of 2,6-dimethoxybenzoyl chloride. The reaction mixture was heated to reflux and stirred for forty-eight hours. It was then cooled to room temperature and concentrated to a volume of about 25 liters by evaporation of the solvent under reduced pressure. The product precipitated and was collected by filtration, washed with fresh toluene, and air dried to provide 6.084 Kg of N-[3-(1-ethyl-1-methylpropyl]-5-isoxazolyl]-2,6-dimethoxybenzamide. M.P. 172°–174° C. Yield 91%.

Analysis calculated for $C_{18}H_{24}N_2O_4$: Theory: C, 65.04; H, 7.28; N, 8.43. Found: C, 64.79; H, 7.02; N, 8.28.

EXAMPLE 2

N-[3-(1,1-dimethylethyl)-5-isoxazolyl]-2,6-di-n-propoxybenzamide (A)

Preparation of 2,6-di-n-propoxybenzoyl chloride

Methyl 2,6-dihydroxybenzoate was reacted with n-propyl iodide in the presence of sodium hydride to provide methyl 2,6-di-n-propoxybenzoate. The ester thus formed was saponified by reaction with 40% aqueous potassium hydroxide in ethanol to afford 2,6-di-n-propoxybenzoic acid. A 20 g portion of the acid was then reacted with 30 g of thionyl chloride in 100 ml of benzene at reflux for five hours. Removal of the solvent by evaportion under reduced pressure and purification of the product by distillation provided 4.88 g of 2,6-di-n-propoxybenzoyl chloride. B.P. 135°–140° C. at 0.2 torr.

(B)

To a stirred solution of 2.8 g of 5-amino-3-(1,1-dimethylethyl)isoxazole in 40 ml of tetrahydrofuran containing 4.5 ml of triethylamine was added dropwise over ten minutes a solution of 4.88 g of 2,6-di-n-propoxybenzoyl chloride in 10 ml of tetrahydrofuran. Following the addition, the reaction mixture was heated at reflux for seventy-two hours. The reaction mixture was then cooled to room temperature and the solvent was removed by evaporation under reduced pressure. The residue was dissolved in a mixture of dichloromethane and water, and the organic layer was separated, washed with fresh water, dried, and the solvent was removed by evaporation to provide an oil. The oil was crystallized from Skelly B and diethyl ether to provide 750 mg of N-[3-(1,1-dimethylethyl)-5-isoxazolyl]-2,6-di-n-propoxybenzamide. M.P. 85°–87° C. Yield 10%.

Analysis calculated for $C_{20}H_{28}N_2O_4$: Theory: C, 66.64; H, 7.83; N, 7.77. Found: C, 67.65; H, 7.78; N, 7.32.

EXAMPLE 3

N-[5-(1-ethylcyclohexyl)-3-isoxazolyl]-2,6-dimethoxybenzamide (A)

Preparation of 3-amino-5-(1-ethylcyclohexyl)isoxazole

Acetonitrile was reacted with 1-ethyl-1-methyoxycarbonylcyclohexane in the presence of sodium hydride to provide 1-ethyl-1-(2-cyanoacetyl)cyclohexane. A 55 g portion of the latter compound was dissolved in 200 ml of diethyl ether containing 20.5 g of absolute methanol, and the solution was stirred and cooled to about 5° C. Hydrogen chloride gas was next bubbled through the reaction mixture for forty-five minutes, after which time the reaction mixture was stored at 0° C. for twelve hours. Removal of the reaction solvent by evaporation under reduced pressure provided a yellow solid, which was dissolved in 300 ml of fresh absolute methanol and treated with 97 g of triethylamine and 22 g of hydroxylamine hydrochloride. The reaction mixture was heated at 50° C. for three hours, and then cooled to room temperature and diluted with 25 ml of concentrated hydrochloric acid. The acidic reaction mixture was heated at 50° C. for twelve hours, and then cooled to room temperature and concentrated to dryness by evaporation of the solvent under reduced pressure. The residue thus obtained was dissolved in water, and the aqueous mixture was made alkaline by the addition of 20% sodium hydroxide. The product was extracted into diethyl ether, which was then washed with water, dried, and the solvent was removed by evaporation. Distillation of the product afforded 14 g of 3-amino-5-(1-ethylcyclohexyl)isoxazole. B.P. 135°–140° C. at 0.1–0.05 torr.

(B)

A solution of 14 g of 3-amino-5-(1-ethylcyclohexyl)isoxazole and 14.4 g of 2,6-dimethoxybenzoyl chloride in 100 ml of toluene was heated to reflux and stirred for eighteen hours. The reaction mixture then was cooled to room temperature and the solvent was removed by evaporation under reduced pressure to provide a solid. The solid was dissolved in 200 ml of dichloromethane, washed with dilute sodium hydroxide and with brine, dried, and the solvent was removed by evaporation. The product was crystallized from dichloromethane and diethyl ether to provide 15.5 g of N-[5-(1-ethylcyclohexyl)-3-isoxazolyl]-2,6-dimethoxybenzamide. M.P. 179°–181° C. Yield 60%.

Analysis calculated for $C_{20}H_{26}N_2O_4$: Theory: C, 67.02; H, 7.31; N, 7.82. Found: C, 66.81; H, 7.02; N, 7.54.

The following exemplary compounds were prepared by reacting an amino-isoxazole with a 2,6-dialkoxy benzoyl halide derivative according to the general methods of Examples 1–3 to provide the corresponding N-isoxazolyl-2,6-dialkoxybenzamide.

EXAMPLE 4

N-[3-(1,1-dimethyl-2-chloroethyl)-5-isoxazolyl]-2,6-dimethoxybenzamide

M.P. 172°–173° C. Yield 33%.

Analysis calculated for $C_{16}H_{19}ClN_2O_4$: Theory: C, 56.72; H, 5.65; N, 8.27; Cl, 10.46. Found: C, 56.49; H, 5.66; N, 8.08; Cl, 10.52.

EXAMPLE 5

N-[3-(2,2-dimethylpropyl)-5-isoxazolyl]-2,6-dimethoxybenzamide

M.P. 152°–154° C. Yield 24%.
Analysis calculated for $C_{17}H_{22}N_2O_4$: Theory: C, 64.13; H, 6.97; N, 8.80. Found: C, 64.07; H, 6.76; N, 8.62.

EXAMPLE 6

N-[3-(1,1-dimethylethyl)-5-isoxazolyl]-2,6-dimethoxybenzamide

M.P. 172°–173° C. Yield 66%.
Analysis calculated for $C_{16}H_{20}N_2O_4$: Theory: C, 63.14; H, 6.62; N, 9.20. Found: C, 62.90; H, 6.52; N, 8.94.

EXAMPLE 7

N-[5-(1,1-dimethylethyl)-3-isoxazolyl]-2,6-dimethoxybenzamide

M.P. 182°–183° C. Yield 27%.
Analysis calculated for $C_{16}H_{20}N_2O_4$: Theory: C, 63.14; H, 6.62; N, 9.20. Found: C, 63.14; H, 6.64; N, 9.07.

EXAMPLE 8

N-[3-(1,1-dimethylethyl)-5-isoxazolyl]-2-methoxy-6-isopropoxybenzamide

M.P. 126°–128° C. Yield 3.5%.
Analysis calculated for $C_{18}H_{24}N_2O_4$: Theory: C, 65.24; H, 7.00; N, 8.45. Found: C, 65.00; H, 6.80; N, 8.39.

EXAMPLE 9

N-[3-(1,1-dimethylpropyl)-5-isoxazolyl]-2,6-dimethoxybenzamide

M.P. 140°–142° C. Yield 50%.
Analyis calculated for $C_{17}H_{22}N_2O_4$: Theory: C, 64.13; H, 6.97; N, 8.80. Found: C, 63.86; H, 6.71; N, 9.05.

EXAMPLE 10

N-[3-(1,1-dimethylpentyl)-5-isoxazolyl]-2,6-dimethoxybenzamide

M.P. 132°–133° C. Yield 31%.
Analysis calculated for $C_{19}H_{26}N_2O_4$: Theory: C, 65.88; H, 7.57; N, 8.09. Found: C, 65.88; H, 7.42; N, 7.86.

EXAMPLE 11

N-[3-(2-cyclohexyl-1,1-dimethylethyl)-5-isoxazolyl]-2,6-dimethoxybenzamide

M.P. 146°–148° C. Yield 21%.
Analysis calculated for $C_{22}H_{30}N_2O_4$: Theory: C, 68.37; H, 7.82; N, 7.25. Found: C, 68.12; H, 7.57; N, 6.99.

EXAMPLE 12

N-[3-(1-cyclohexyl-1-methylethyl)-5-isoxazolyl]-2,6-dimethoxybenzamide

M.P. 158°–160° C. Yield 91%.
Analysis calculated for $C_{21}H_{28}N_2O_4$: Theory: C, 67.72; H, 7.58; N, 7.52. Found: C, 67.56; H, 7.37; N, 7.56.

EXAMPLE 13

N-[3-(1,1-dimethyl-2-phenylethyl)-5-isoxazolyl]-2,6-dimethoxybenzamide

M.P. 108°–110° C. Yield 9%.
Analysis calculated for $C_{22}H_{25}N_2O_4$: Theory: C, 69.46; H, 6.36; N, 7.36. Found: C, 69.28; H, 6.53; N, 7.12.

EXAMPLE 14

N-[3-(1ethyl-1-methylbutyl)-5-isoxazolyl]-2,6-dimethoxybenzamide

M.P. 149°–151° C. Yield 41%.
Analysis calculated for $C_{19}H_{26}N_2O_4$: Theory: C, 65.88; H, 7.57; N, 8.09. Found: C, 65.59; H, 7.35; N, 7.87.

EXAMPLE 15

N-[3-(1,1-diethylpropyl)-5-isoxazolyl]-2,6-dimethoxybenzamide

M.P. 163°–165° C. Yield 13%.

EXAMPLE 16

N-[3-(1,1-dimethyl-3-butenyl)-5-isoxazolyl]-2,6-dimethoxybenzamide

M.P. 160°–162° C. Yield 22%.
Analysis calculated for $C_{18}H_{22}N_2O_4$; Theory: C, 65.44; H, 6.71; N, 8.48. Found: C, 65.23; H, 6.50; N, 8.39.

EXAMPLE 17

N-[3-(1-methylcyclohexyl)-5-isoxazolyl]-2,6-dimethoxybenzamide

M.P. 161°–163° C. Yield 54%.
Analysis calculated for $C_{19}H_{24}N_2O_4$; Theory: C, 66.26; H, 7.02; N, 8.13. Found: C, 66.06; H, 6.80; N, 8.28.

EXAMPLE 18

N-[3-(1,1-dimethyltetradecyl)-5-isoxazolyl]-2,6-dimethoxybenzamide

M.P. 57°–59° C. Yield 9%.
Analysis calculated for $C_{28}H_{44}N_2O_4$; Theory: C, 71.15; H, 9.38; N, 5.93. Found: C, 71.34; H, 9.15; N, 5.81.

EXAMPLE 19

N-[3-(1-ethylcyclohexyl)-5-isoxazolyl]-2,6-dimethoxybenzamide

M.P. 177°–179° C. Yield 34%.
Analysis calculated for $C_{20}H_{26}N_2O_4$; Theory: C, 67.02; H, 7.31, N, 7.82. Found: C, 66.74; H, 7.07; N, 7.90.

EXAMPLE 20

N-[3-(1,1,3-trimethylbutyl)-5-isoxazolyl]-2,6-dimethoxybenzamide

M.P. 146°–148° C. Yield 12%.
Analysis calculated for $C_{19}H_{26}N_2O_4$; Theory: C, 65.88; H, 7.57; N, 8.09. Found: C, 65.70; H, 7.50; N, 7.87.

EXAMPLE 21

N-[3-(1-methylcyclopentyl)-5-isoxazolyl]-2,6-dimethoxybenzamide

M.P. 128°–130° C. Yield 10%.
Analysis calculated for $C_{18}H_{22}N_2O_4$; Theory: C, 65.44; H, 6.71; N, 8.48. Found: C, 65.24; H, 6.59; N, 8.22.

EXAMPLE 22

N-[5-(1,1-dimethylbutyl)-3-isoxazolyl]-2,6-dimethoxybenzamide

M.P. 133°–135° C. Yield 48%.
Analysis calculated for $C_{18}H_{24}N_2O_4$; Theory: C, 65.04; H, 7.28; N, 8.43. Found: C, 65.25; H, 7.01; N, 8.19.

EXAMPLE 23

N-[3-(1,1,2,2-tetramethylpropyl)-5-isoxazolyl]-2,6-dimethoxybenzamide

M.P. 174°–175° C.

Analysis calculated for $C_{19}H_{26}N_2O_4$; Theory: C, 65.88; H, 7.57; N, 8.09. Found: C, 65.97; H, 7.32; N, 8.33.

EXAMPLE 24

N-[3-(1-ethylpropyl)-5-isoxazolyl]-2,6-dimethoxybenzamide

M.P. 157°–159° C. Yield 53%.

Analysis calculated for $C_{17}H_{22}N_2O_4$; Theory: C, 64.13; H, 6.97; N, 8.80. Found: C, 63.87; H, 6.77; N, 8.56.

EXAMPLE 25

N-[5-(1-ethyl-1-methylpropyl)-3-isoxazolyl]-2,6-dimethoxybenzamide

M.P. 165°–166° C. Yield 49%.

Analysis calculated for $C_{18}H_{24}N_2O_4$; Theory: C, 65.04; H, 7.28; N, 8.43. Found: C, 64.94; H, 7.01; N, 8.21.

EXAMPLE 26

N-[3-(1,1-dimethylethyl)-5-isoxazolyl]-2,6-dimethoxybenzamide

M.P. 123°–125° C. Yield 11%.

Analysis calculated for $C_{18}H_{24}N_2O_4$; Theory: C, 65.04; H, 7.28; N, 8.43. Found: C, 64.50; H, 7.04; N, 7.89.

EXAMPLE 27

N-[3-(2-methoxy-1,1-dimethylethyl)-5-isoxazolyl]-2,6-dimethoxybenzamide

M.P. 201°–203° C. Yield 19%.

Analysis calculated for $C_{17}H_{22}N_2O_5$; Theory: C, 61.06; H, 6.63; N, 8.38. Found: C, 61.50; H, 6.36, N, 8.51.

EXAMPLE 28

N-[3-(1,1-dimethylbutyl)-5-isoxazolyl]-2,6-dimethoxybenzamide

M.P. 141°–143° C. Yield 9%.

Analysis calculated for $C_{18}H_{24}N_2O_4$; Theory: C, 65.04; H, 7.28; N, 8.43. Found: C, 64.79; H, 7.04; N, 8.26.

EXAMPLE 29

N-[3-(1-propylcyclohexyl)-5-isoxazolyl]-2,6-dimethoxybenzamide

M.P. 202°–204° C. Yield 38%.

Analysis calculated for $C_{21}H_{28}N_2O_4$; Theory: C, 67.72; H, 7.58; N, 7.52. Found: C, 67.48; H, 7.58; N, 7.56.

EXAMPLE 30

N-[3-(1-methyl-1-(2,4-dichlorophenoxy)ethyl)-5-isoxazolyl]-2,6-dimethoxybenzamide M.P. 154°–156° C. Yield 25%.

Analysis calculated for $C_{21}H_{20}Cl_2N_2O_5$; Theory: C, 55.89; H, 4.47; N, 6.21; Cl, 15.71. Found: C, 56.09; H, 4.46; N, 6.01; Cl, 15.45.

EXAMPLE 31

N-[3-(1-methyl-1-phenylethyl)-5-isoxazolyl]-2,6-dimethoxybenzamide

M.P. 185°–187° C. Yield 30%.

Analysis calculated for $C_{21}H_{22}N_2O_4$; Theory: C, 68.84; H, 6.05; N, 7.65. Found: C, 69.04; H, 5.93; N, 7.44.

EXAMPLE 32

N-[3-(1-methyl-1-phenylpropyl)-5-isoxazolyl]-2,6-dimethoxybenzamide

M.P. 183°–185° C. Yield 29%.

Analysis calculated for $C_{22}H_{24}N_2O_4$; Theory: C, 69.46; H, 6.36; N, 7.36. Found: C, 69.26; H, 6.13; N, 7.54.

EXAMPLE 33

N-[3-(1-methyl-1-(phenylmethoxy)ethyl)-5-isoxazolyl-2,6-dimethoxybenzamide

M.P. 123°–125° C. Yield 13%.

Analysis calculated for $C_{22}H_{24}N_2O_5$; Theory: C, 66.65; H, 6.10; N, 7.07. Found: C, 66.84; H, 5.88; N, 6.86.

EXAMPLE 34

N-[3-(1-ethylcycloheptyl)-5-isoxazolyl]-2,6-dimethoxybenzamide

M.P. 163°–165° C. Yield 32%.

Analysis calculated for $C_{21}H_{28}N_2O_4$; Theory: C, 67.72; H, 7.58; N, 7.52. Found: C, 67.64; H, 7.78; N, 7.25.

EXAMPLE 35

N-[3-(1-cyclohexyl-1-methylpropyl)-5-isoxazolyl]-2,6-dimethoxybenzamide

M.P. 173°–175° C. Yield 22%.

Analysis calculated for $C_{22}H_{30}N_2N_4$; Theory: C, 68.37; H, 7.82; N, 7.25. Found: C, 68.29; H, 7.53; N, 7.27.

EXAMPLE 36

N-[3-(1-methoxy-1-methylethyl)-5-isoxazolyl]-2,6-dimethoxybenzamide

M.P. 232°–234° C. Yield 37%.

Analysis calculated for $C_{16}H_{20}N_2O_5$; Theory: C, 59.99; H, 6.29; N, 8.74. Found: C, 59.87; H, 6.07; N, 8.73.

By the following the general procedures of Examples 1–3, an amino-isoxazole was reacted with a suitably substituted benzoyl halide to give the following N-isoxazolyl benzamides.

EXAMPLE 37

N-[3-(1-ethyl-1-methylpropyl)-5-isoxazolyl]2fluoro-6-methoxybenzamide

M.P. 133°–135° C. Yield 26%.

Analysis calculated for $C_{17}H_{21}N_2O_3F$; Theory: C, 63.74; H, 6.61; N, 8.74. Found: C, 63.97; H, 6.48; N, 8.70.

EXAMPLE 38

N-[5-(1,1-dimethylethyl)-3-isoxazolyl]-2,6-dichlorobenzamide

M.P. 249°–250° C.

Analysis calculated for $C_{14}H_{14}Cl_2N_2O_2$; Theory: C, 53.69; H, 4.51; N, 8.94. Found: C, 53.89; H, 4.54; N, 8.77.

EXAMPLE 39

N-[3-(1,1-dimethylethyl)-5-isoxazolyl]-2,6-dichlorobenzamide

M.P. 235°–237° C. Yield 22%.

Analysis calculated for $C_{14}H_{14}Cl_2N_2O_2$; Theory: C, 53.69; H, 4.51; N, 8.94; Cl, 22.64. Found: C, 53.74; H, 4.56; N, 8.96; Cl, 22.83.

EXAMPLE 40

N-[3-(1,1-dimethylethyl)-5-isoxazolyl]-2,6-difluorobenzamide

M.P. 153°-154° C.

Analysis calculated for $C_{14}H_{14}F_2N_2O_2$; Theory: C, 60.00; H, 5.04; N, 10.00. Found: C, 59.91; H, 4.83; N, 10.16.

EXAMPLE 41

N-[3-(1-ethyl-1-methylpropyl)-5-isoxazolyl]-2-chloro-6-methoxybenzamide

M.P. 173°-174° C. Yield 42%.

Analysis calculated for $C_{17}H_{21}ClN_2O_3$; Theory: C, 60.62; H, 6.28; N, 8.32. Found: C, 6.74; H, 6.02; N, 8.54.

EXAMPLE 42

N-[3-(1-ethyl-1-methylpropyl)-5-isoxazolyl]-2,4,6-trimethoxybenzamide

M.P. 150°-152° C. Yield 40%.

Analysis calculated for $C_{19}H_{26}N_2O_5$; Theory: C, 62.97; H, 7.23; N, 7.73. Found: C, 63.01; H, 7.05; N, 7.72.

EXAMPLE 43

N-[5-(1-ethyl-1-methylpropyl)-3-isoxazolyl]-2,4,6-trimethoxybenzamide

M.P. 165°-170° C. Yield 41%.

Analysis calculated for $C_{19}H_{26}N_2O_5$; Theory: C, 62.97; H, 7.23; N, 7.73. Found: C, 62.94; H, 6.99; N, 7.94.

EXAMPLE 44

N-[3-(1-ethyl-1-methoxymethylpropyl)-5-isoxazolyl]-2,6-dimethoxybenzamide

EXAMPLE 45

N-[3-(1,1-diethyl-2-propenyl)-5-isoxazolyl]-2,6-dimethoxybenzamide

EXAMPLE 46

N-[3-(1,1-dimethylethyl)-5-isoxazolyl]-2,4-dimethoxybenzamide

M.P. 166°-168° C. Yield 53%.

Analysis calculated for $C_{16}H_{20}N_2O_4$; Theory: C, 63.14; H, 6.62; N, 9.20. Found: C, 63.38; H, 6.71; N, 9.01.

EXAMPLE 47

N-[3-(1,1-dimethylethyl)-5-isoxazolyl]-3,5-dimethylbenzamide

M.P. 121°-123° C. Yield 45%.

Analysis calculated for $C_{16}H_{20}N_2O_2$; Theory: C, 70.56; H, 7.40; N, 10.29. Found: C, 70.82; H, 7.25; N, 10.21.

EXAMPLE 48

N-[3-propyl-5-isoxazolyl]-2,6-dimethoxybenzamide

M.P. 124°-126° C. Yield 29%.

Analysis calculated for $C_{15}H_{18}N_2O_4$; Theory: C, 62.06; H, 6.25; N, 9.65. Found: C, 62.34; H, 6.46; N, 9.55.

EXAMPLE 49

N-(3-propyl-5-isoxazolyl)-2,6-dimethylbenzamide

M.P. 120°-122° C.

Analysis calculated for $C_{15}H_{18}N_2O_2$; Theory: C, 69.74; H, 7.02; N, 10.84. Found: C, 69.98; H, 6.82; N, 10.58.

EXAMPLE 50

N-[3-(1,1-dimethylethyl)-5-isoxazolyl]-3,4-dimethoxybenzamide

M.P. 164°-166° C. Yield 37%.

Analysis calculated for $C_{16}H_{20}N_2O_4$; Theory: C, 63.14; H, 6.62; N, 9.20. Found: C, 63.27; H, 6.41; N, 9.12.

EXAMPLE 51

N-[3-(1,1-dimethylethyl)-5-isoxazolyl]-3,5-dimethoxybenzamide

M.P. 115°-117° C. Yield 49%.

Analysis calculated for $C_{16}H_{20}N_2O_4$; Theory: C, 63.14; H, 6.62; N, 9.20. Found: C, 63.40; H, 6.37; N, 9.30.

EXAMPLE 52

N-[3-(1-methylethyl)-5-isoxazolyl]-2,6-dimethoxybenzamide

M.P. 143°-144° C. Yield 52%.

Analysis calculated for $C_{15}H_{18}N_2O_4$; Theory: C, 62.49; H, 5.59; N, 9.72. Found: C, 62.20; H, 5.46; N, 9.51.

EXAMPLE 53

N-[3-(1,1-dimethylethyl)-5-isoxazolyl]-2,4,6-trimethylbenzamide

M.P. 177°-179° C. Yield 22%.

Analysis calculated for $C_{17}H_{22}N_2O_2$; Theory: C, 71.30; H, 7.74; N, 9.78. Found: C, 71.34; H, 7.45; N, 9.78.

EXAMPLE 54

N-[3-(1-ethyl-1-(methoxymethyl)propyl)-5-isoxazolyl]-2,6-dimethoxybenzamide

M.P. 167°-168° C. Yield 26%.

Analysis calculated for $C_{19}H_{26}N_2O_5$; Theory: C, 62.97; H, 7.23; N, 7.73. Found: C, 63.23; H, 7.00; N, 7.76.

EXAMPLE 55

N-[3-(1-ethyl-1-methylpentyl)-5-isoxazolyl]-2,6-dimethoxybenzamide

M.P. 150°-152° C. Yield 34%.

Analysis calculated for $C_{21}H_{30}N_2O_4$; Theory: C, 66.54; H, 7.83; N, 7.77. Found: C, 66.76; H, 7.67; N, 7.53.

EXAMPLE 56

N-[3-(1,1-dimethylethyl)-5-isoxazolyl]-2,6-dimethylbenzamide

M.P. 179°-181° C. Yield 32%.

Analysis calculated for $C_{16}H_{20}N_2O_2$; Theory: C, 70.56; H, 7.40; N, 10.29. Found: C, 70.35; H, 7.19; N, 10.02.

EXAMPLE 57

N-[3-(2,2-dimethyl-3-[2-methyl-1-propenyl]cyclopropyl)-5-isoxazolyl]-2,6-dimethoxybenzamide M.P. 92°-94° C. Yield 8%.

Analysis calculated for $C_{21}H_{24}N_2O_4$; Theory: C, 68.09; H, 7.07; N, 7.56. Found: C, 68.16; H, 6.83; N, 7.42.

EXAMPLE 58

N-[3-(1-ethyl-1-methoxypropyl)-5-isoxazolyl]2,6-dimethoxybenzamide

M.P. 174°-176° C. Yield 7%.

Analysis calculated for $C_{18}H_{24}N_2O_5$; Theory: C, 62.05; H, 6.44; N, 8.04. Found: C, 61.83; H, 6.87; N, 7.82.

EXAMPLE 59

N-[3-(1,1-dimethylethyl)-5-isoxazolyl]-2,6-diethylbenzamide

M.P. 173°–175° C. Yield 7%.

Analysis calculated for $C_{18}H_{24}N_2O_2$; Theory: C, 71.97; H, 8.05; N, 9.33. Found: C, 72.20; H, 8.24; N, 9.21.

EXAMPLE 60

N-[3-(1,1-dimethylethyl)-5-isoxazolyl]-2,4,6-trimethoxybenzamide

M.P. 115°–118° C. Yield 26%.

Analysis calculated for $C_{17}H_{22}N_2O_5$; Theory: C, 61.07; H, 6.63; N, 8.38; Found: C, 60.88; H, 6.76; N, 8.12.

EXAMPLE 61

N-[5-(1-ethyl-1-methylpropyl)-1,3,4-thiadiazol-2-yl]-2,6-dimethoxybenzamide (A)

Preparation of 2-amino-5-(1-ethyl-1-methylpropyl)-1,3,4-thiadiazole

A solution containing 13.0 g of 2-ethyl-2-methylbutyric acid and 9.1 g of thiosemicarbazide in 125 ml of dioxane was stirred and heated to 90° C. To the stirred reaction mixture was added dropwise over thirty minutes 15.3 g of phosphorous oxychloride. Following complete addition, the reaction mixture was heated at 90° C. for six hours. The mixture was then cooled to about 30° C. and added to 100 g of ice. The aqueous mixture was made alkaline by the addition of ammonium hydroxide, and the alkaline solution was extracted several times with ethyl acetate. The extracts were combined, washed with water, dried, and the solvent was removed by evaporation under reduced pressure to afford 17.0 g of 2-amino-5-(1-ethyl-1-methylpropyl)-1,3,4-thiadiazole.

M.P. 138°–140° C.

(B)

To a stirred solution of 9.2 g of the thiadiazole from above in 100 ml of tetrahydrofuran containing 4.0 g of pyridine were added in one portion 11.0 g of 2,6-dimethoxybenzoyl chloride. The reaction mixture was heated at reflux for three hours, and then cooled to about 30° C. and filtered. The solvent was removed from the filtrate by evaporation under reduced pressure to provide a solid which, when crystallized from 2B ethanol afforded 6.3 g of N-[5-(1-ethyl-1-methylpropyl)-1,3,4-thiadiazol-2-yl]-2,6-dimethoxybenzamide.

M.P. 208°–210° C. Yield 36%.

Analysis calculated for $C_{17}H_{23}N_3O_3S$: Theory: C, 58.43; H, 6.63; N, 12.02. Found: C, 58.34; H, 6.58; N, 11.79.

EXAMPLE 62

N-[5-(1-ethyl-1-methylpropyl)-1,3,4-thiadiazol-2-yl]-benzamide

To a stirred suspension of 3.3 g of 2-amino-5-(1-ethyl-1-methylpropyl)-1,3,4-thiadiazole in 30 ml of tetrahydrofuran were added in one portion 2.8 g of benzoyl chloride. The reaction mixture was stirred at room temperature while a solution of 1.6 g of pyridine in 20 ml of tetrahydrofuran was added dropwise over thirty minutes. Following complete addition, the reaction mixture was heated at reflux for three hours. The mixture was then filtered to remove the pyridine hydrochloride, and the filtrate was washed several times with 1N hydrochloric acid solution. The organic layer was separated and the solvent was removed by evaporation under reduced pressure to provide a yellow gum. The gum was crystallized from the ethanol and water to afford 1.85 g of N-[5-(1-ethyl-1-methylpropyl)-1,3,4-thiadiazol-2-yl]benzamide.

M.P. 98°–100° C. Yield 35%.

Analysis calculated for $C_{15}H_{19}N_3OS$; Theory: C, 62.25; H, 6.62; N, 14.52; S, 11.08. Found: C, 62.01; H, 6.39; N, 14.27; S, 11.22.

EXAMPLE 63

N-[5-(1-ethyl-1-methylpropyl)-1,3,4-thiadiazol-2-yl]-2,6-diethylbenzamide (A)

Preparation of 2,6-diethylbenzoyl chloride 2,6-Diethylcyanobenzene was prepared by converting 2,6-diethylaniline to a diazonium salt and then reacting the diazonium salt with copper cyanide. Hydrolysis of 2,6-diethylcyanobenzene was effected by reaction with sodium hydroxide in ethylene glycol to provide 2,6-diethylaminocarbonyl benzene. The latter compound was reacted with phosphoric acid to provide 2,6-diethylbenzoic acid. Reaction of the benzoic acid with thionyl chloride afforded 2,6-diethylbenzoylchloride as an oil.

(B)

A solution of 1.85 g of 2-amino-5-(1-ethyl-1-methylpropyl)-1,3,4-thiadiazole and 2.21 g of 2,6-diethylbenzoyl chloride in 50 ml of toluene was heated at reflux for sixteen hours and then cooled and the solvent was removed by evaporation under reduced pressure to provide a solid residue. The solid was crystallized from 2B ethanol to give 1.25 g of N-[5-(1-ethyl-1-methylpropyl)-1,3,4-thiadiazol-2-yl]-2,6-diethylbenzamide.

M.P. 186°–188° C. Yield 36%.

Analysis calculated for $C_{19}H_{27}N_3OS$: Theory: C, 66.05; H, 7.88; N, 12.16; S, 9.28. Found: C, 66.18; H, 7.82; N, 11.87; S, 9.16.

EXAMPLE 64

N-[5-(1,1-dimethyl-2-(methylthio)ethyl)-1,3,4-thiadiazol-2-yl]-2,6-dimethoxybenzamide (A)

Preparation of 2-amino-5-[1,1-dimethyl-2-(methylthio)ethyl]-1,3,4-thiadiazole

Lithium diisopropylamide was prepared by reacting 51.0 g of diisopropylamine with 227 ml of n-butyl lithium in 350 ml of tetrahydrofuran at −5° C. To the stirred reaction mixture were added dropwise over thirty minutes 22.0 g of isobutyric acid. Following the addition, the reaction mixture was warmed to 25° C. and stirred for one hour. The mixture was then again cooled to −5° C., and 24.1 g of chloromethyl methylsulfide were added dropwise. The reaction mixture was allowed to warm to 25° C. and was stirred at that temperature for twelve hours. The excess solvent was next removed by evaporation under reduced pressure, and the residue was added to 50 g of ice containing 50 ml of 1N hydrochloric acid solution. The aqueous acid mixture was extracted several times with diethyl ether, and the extracts were combined, washed with water, dried, and the solvent was removed by evaporation to give 22.0 g of 2,2-dimethyl-methylthiopropionic acid as an oil.

A 9.0 g portion of the acid thus formed was dissolved in 120 ml of dioxane containing 5.5 g of thiosemicarbazide, and the reaction mixture was heated at 90° C. for thirty minutes, and then a 10.1 g portion of phosphorus oxychloride was added dropwise over ten minutes to the reaction mixture. Following complete addition, the mixture was heated at 90° C. for twelve hours. After cooling the reaction mixture to room temperature, the solvent was decanted and the solid precipitate was dissolved in warm water. The aqueous mixture was made alkaline to pH 8 by the addition of ammonium hydroxide, and then the alkaline solution was extracted with ethyl acetate. The extracts were combined, washed with water, dried, and the solvent was removed by evaporation under reduced pressure to provide 4.2 g of 2-amino-5-[1,1-dimethyl-2-(methylthio)ethyl]-1,3,4-thiadiazole.

M.P. 117°–120° C.

(B)

A 3.0 g portion of the thiadiazole thus prepared was reacted with 3.4 g of 2,6-dimethoxybenzoyl chloride in 30 ml of tetrahydrofuran containing 1.3 g of pyridine.

The reaction was carried out at 106° C. for sixteen hours. After cooling the reaction mixture to room temperature, the solvent was removed by evaporation under reduced pressure to leave the product as an oil. The oil was purified first by chromatography over silica gel using diethyl ether as an eluant, and then by crystallization from ethyl acetate to provide 1.94 g of N-[5-(1,1-dimethyl-2-(methylthio)ethyl]-1,3,4-thiadiazol-2-yl]-2,6-dimethoxybenzamide.

M.P. 165°–167° C. Yield 35%.

Analysis calculated for $C_{16}H_{21}N_3O_3S_2$: Theory: C, 52.29; H, 5.76; N, 11.43; S, 17.45. Found: C, 52.38; H, 5.47; N, 11.20; S, 17.40.

By following the general procedures of Examples 61–64, an appropriately substituted 2-amino-1,3,4-thiadiazole was reacted with a benzoyl halide derivative to provide the following exemplary N-(1,3,4-thiadiazol-2-yl)benzamides.

EXAMPLE 65

N-[5-(1-cyclohexyl-1-methylethyl)-1,3,4-thiadiazol-2-yl]-2,6-dimethoxybenzamide.

M.P. 241°–243° C. Yield 38%.

Analysis calculated for $C_{20}H_{27}N_3O_3S$: Theory: C, 61.67; H, 6.99; N, 10.79. Found: C, 61.68; H, 6.76; N, 10.77.

EXAMPLE 66

N-[5-(1,1-diethylpropyl)-1,3,4-thiadiazol-2-yl]-2,6-dimethoxybenzamide.

M.P. 216°–218° C. Yield 31%.

Analysis calculated for $C_{18}H_{25}N_3O_3S$: Theory: C, 59.48; H, 6.93; N, 11.56. Found: C, 59.65; H, 6.73; N, 11.37.

EXAMPLE 67

N-[5-(2,2-dimethylpropyl)-1,3,4-thiadiazol-2-yl]-2,6-dimethoxybenzamide

M.P. 188°–190° C. Yield 43%.

Analysis calculated for $C_{16}H_{21}N_3O_3S$: Theory: C, 57.29; H, 6.31; N, 12.53. Found: C, 57.27; H, 6.10; N, 12.31.

EXAMPLE 68

N-[5-(2-methoxy-1,1-dimethylethyl)-1,3,4-thiadiazol-2-yl]-2,6-dimethoxybenzamide M.P. 172°–174° C. Yield 56%.

Analysis calculated for $C_{16}H_{21}N_3O_4S$: Theory: C, 54.68; H, 6.02; N, 11.96. Found: C, 54.56; H, 5.95; N, 11.72.

EXAMPLE 69

N-[5-(1,1-dimethyl-2-phenylethyl)-1,3,4-thiadiazol-2-yl]-2,6-dimethoxybenzamide

M.P. 167°–169° C. Yield 29%.

Analysis calculated for $C_{21}H_{23}N_3O_3S$: Theory: C, 63.45; H, 5.83; N, 10.57; S, 8.07. Found: C, 63.71; H, 5.82; N, 10.71; S, 8.05.

EXAMPLE 70

N-[5-(2-cyclohexyl-1,1-dimethylethyl)-1,3,4-thiadiazol-2-yl]-2,6-dimethoxybenzamide M.P. 191°–193° C. Yield 77%.

Analysis calculated for $C_{21}H_{29}N_3O_3S$: Theory: C, 62.50; H, 7.24; N, 10.41; S, 7.95. Found: C, 62.63; H, 7.22; N, 10.43; S, 7.99.

EXAMPLE 71

N-[5-(1,1-dimethylhexyl)-1,3,4-thiadiazol-2-yl]-2,6-dimethoxybenzamide

M.P. 120°–122° C. Yield 66%.

Analysis calculated for $C_{19}H_{27}N_3O_3S$: Theory: C, 60.45; H, 7.21; N, 11.13; S, 8.49. Found: C, 60.64; H, 7.00; N, 11.27; S, 8.75.

EXAMPLE 72

N-[5-(1-ethyl-1-methylpropyl)-1,3,4-thiadiazol-2-yl]-2-methoxy-3,6-dichlorobenzamide M.P. 194°–196° C. Yield 6%.

Analysis calculated for $C_{16}H_{19}Cl_2N_3O_2S$: Theory: C, 49.49; H, 4.93; N, 10.82. Found: C, 49.69; H, 5.10; N, 11.04.

EXAMPLE 73

N-[5-(1-ethylpentyl)-1,3,4-thiadiazol-2-yl]-2,6-dimethoxybenzamide

M.P. 120°–122° C. Yield 69%.

Analysis calculated for $C_{18}H_{25}N_3O_3S$: Theory: C, 59.48; H, 6.93; N, 11.56. Found: C, 59.74; H, 6.90; N, 11.45.

EXAMPLE 74

N-[5-(1-methylcyclohexyl)-1,3,4-thiadiazol-2-yl]-2,6-dimethoxybenzamide

M.P. 211°–213° C. Yield 47%.

Analysis calculated for $C_{11}H_{23}N_3O_3S$: Theory: C, 59.81; H, 6.41; N, 11.63. Found: C, 60.03; H, 6.13; N, 11.83.

EXAMPLE 75

N-[5-(1-methylpropyl)-1,3,4-thiadiazol-2-yl]-2,6-dimethoxybenzamide

M.P. 137°–140° C. Yield 27%.

Analysis calculated for $C_{15}H_{19}N_3O_3S$: Theory: C, 56.06; H, 5.96; N, 13.07. Found: C, 56.27; H, 6.03; N, 12.85.

EXAMPLE 76

N-[5-(1-ethyl-1-methylbutyl)-1,3,4-thiadiazol-2-yl]-2,6-dimethoxybenzamide

M.P. 145°–146° C. Yield 15%.

Analysis calculated for $C_{18}H_{25}N_3O_3S$: Theory: C, 59.48; H, 6.93; N, 11.56. Found: C, 59.33; H, 7.03; N, 11.49.

EXAMPLE 77

N-[5-(cyclohexylmethyl)-1,3,4-thiadiazol-2-yl]-2,6-dimethoxybenzamide

M.P. 152°–154° C. Yield 54%.

Analysis calculated for $C_{18}H_{23}N_3O_3S$: Theory: C, 59.81; H, 6.41; N, 11.63, S, 8.87. Found: C, 59.87; H, 6.40; N, 11.34; S, 8.62.

EXAMPLE 78

N-[5-(2,2-dimethylbutyl)-1,3,4-thiadiazol-2-yl]-2,6-dimethoxybenzamide

M.P. 168°–169° C. Yield 42%.

Analysis calculated for $C_{17}H_{23}N_3O_3S$: Theory: C, 58.43; H, 6.63; N, 12.02. Found: C, 58.70; H, 6.79; N, 11.77.

EXAMPLE 79

N-[5-(1-methylcyclopropyl)-1,3,4-thiadiazol-2-yl]-2,6-dimethoxybenzamide

M.P. 197°–198° C. Yield 41%.

Analysis calculated for $C_{15}H_{17}N_3O_3S$: Theory: C, 56.41; H, 5.37; N, 13.16. Found: C, 56.19; H, 5.25; N, 12.99.

EXAMPLE 80

N-[5-(1-methylcyclopentyl)-1,3,4-thiadiazol-2-yl]-2,6-dimethoxybenzamide

M.P. 218°–220° C. Yield 22%.

Analysis calculated for $C_{17}H_{21}N_3O_3S$: Theory: C, 58.77; H, 6.09; N, 12.09. Found: C, 58.98; H, 6.34; N, 12.09.

EXAMPLE 81

N-[5-(2,2-dichloro-1-methylcyclopropyl)-1,3,4-thiadiazol-2-yl]-2,6-dimethoxybenzamide M.P. 235°–236° C. Yield 63%.

Analysis calculated for $C_{15}H_{15}Cl_2N_3O_3S$: Theory: C, 46.40; H, 3.89; N, 10.82. Found: C, 46.66; H, 3.64; N, 10.60.

EXAMPLE 82

N-[5-(1,2-dimethylpropyl)-1,3,4-thiadiazol-2-yl]-2,6-dimethoxybenzamide

M.P. 169°–171° C. Yield 50%.

Analysis calculated for $C_{16}H_{21}N_3O_3S$: Theory: C, 57.29; H, 6.31; N, 12.53. Found: C, 57.29; H, 6.02; N, 12.37.

EXAMPLE 83

N-[5-(1,1-dimethyl-3-butenyl)-1,3,4-thiadiazol-2-yl]-2,6-dimethoxybenzamide

M.P. 170°–172° C. Yield 38%.

Analysis calculated for $C_{17}H_{21}N_3O_3S$: Theory: C, 58.77; H, 6.09; N, 12.09, S, 9.23. Found: C, 58.75; H, 5.89; N, 11.91; S, 8.98.

EXAMPLE 84

N-[5-(1-ethyl-1-methylpropyl)-1,3,4-thiadiazol-2-yl]-2-chlorobenzamide

M.P. 233°–234° C. Yield 49%.

Analysis calculated for $C_{15}H_{18}ClN_3OS$: Theory: C, 55.63; H, 5.60; N, 12.98. Found: C, 55.40; H, 5.36; N, 12.81.

EXAMPLE 85

N-[5-(1-ethyl-1-methylpropyl)-1,3,4-thiadiazol-2-yl]-2-methoxybenzamide

M.P. 114°–115° C. Yield 25%.

Analysis calculated for $C_{16}H_{21}N_3O_2S$: Theory: C, 60.16; H, 6.63; N, 13.16. Found: C, 59.96; H, 6.42; N, 13.05.

EXAMPLE 86

N-[5-(1-ethyl-1-methylpropyl)-1,3,4-thiadiazol-2-yl]-2,6-dimethylbenzamide

M.P. 191°–192° C. Yield 32%.

Analysis calculated for $C_{17}H_{23}N_3OS$: Theory: C, 64.32; H, 7.30; N, 13.24. Found: C, 64.47; H, 7.41; N, 13.46.

EXAMPLE 87

N-[5-(1-ethyl-1-methylpropyl)-1,3,4-thiadiazol-2-yl]-2-(methylthio)benzamide

M.P. 145°–147° C. Yield 62.1%.

Analysis calculated for $C_{16}H_{21}N_3OS_2$: Theory: C, 57.28; H, 6.31; N, 12.53; S, 19.11. Found: C, 56.99; H, 6.06; N, 12.50; S, 19.35.

EXAMPLE 88

N-[5-(1-ethylcyclohexyl)-1,3,4-thiadiazol-2-yl]-2,6-dimethoxybenzamide

M.P. 222°–224° C. Yield 25%.

Analysis calculated for $C_{19}H_{25}N_3O_3S$: Theory: C, 60.78; H, 6.71; N, 11.19. Found: C, 60.63; H, 6.85; N, 10.92.

EXAMPLE 89

N-[5-(1,1-diethylbutyl)-1,3,4-thiadiazol-2-yl]-2,6-dimethoxybenzamide

M.P. 210°–212° C. Yield 61%.

Analysis calculated for $C_{19}H_{27}N_3O_3S$: Theory: C, 60.45; H, 7.21; N, 11.13. Found: C, 60.47; H, 6.94; N, 10.97.

EXAMPLE 90

N-[5-(1,1,2-trimethylpropyl)-1,3,4-thiadiazol-2-yl]-2,6-dimethoxybenzamide

M.P. 197°–199° C. Yield 22%.

Analysis calculated for $C_{17}H_{23}N_3O_3S$: Theory: C, 58.43; H, 6.63; N, 12.02; S, 9.18. Found: C, 58.66; H, 6.43; N, 12.02; S, 9.03.

EXAMPLE 91

N-[5-(1-ethylcyclopentyl)-1,3,4-thiadiazol-2-yl]-2,6-dimethoxybenzamide

M.P. 226°–228° C. Yield 62%.

Analysis calculated for $C_{18}H_{23}N_3O_3S$: Theory: C, 59.81; H, 6.41; N, 11.63; S, 8.87. Found: C, 59.91; H, 6.16; N, 11.71; S, 9.08.

EXAMPLE 92

N-[5-(1-ethyl-1-methylpropyl)-1,3,4-thiadiazol-2-yl]-2,6-dichlorobenzamide

M.P. 276°–277° C. Yield 39%.

Analysis calculated for $C_{15}H_{17}Cl_2N_3OS$: Theory: C, 50.28; H, 4.78; N, 11.73; S, 8.95; Cl, 19.79. Found: C, 50.52; H, 4.54; N, 11.56; S, 8.69; Cl, 20.03.

EXAMPLE 93

N-(5-methyl-1,3,4-thiadiazol-2-yl)-2,6-dimethoxybenzamide

M.P. 187°–188° C. Yield 85%.

Analysis calculated for $C_{12}H_{13}N_3O_3S$: Theory: C, 51.60; H, 4.69; N, 15.04. Found: C, 51.72; H, 4.50; N, 15.05.

EXAMPLE 94

N-[5-(methoxymethyl)-1,3,4-thiadiazol-2-yl]-2,6-dimethoxybenzamide

M.P. 164°–166° C. Yield 51%.

Analysis calculated for $C_{13}H_{15}N_3O_4S$: Theory: C, 50.48; H, 4.89; N, 13.58; S, 10.37. Found: C, 50.63; H, 4.74; N, 13.37; S, 10.39.

EXAMPLE 95

N-[5-(1-methyl-1-propylbutyl)-1,3,4-thiadiazol-2-yl]-2,6-dimethoxybenzamide

M.P. 161°–163° C. Yield 40%.

Analysis calculated for $C_{19}H_{27}N_3O_3S$: Theory: C, 60.45; H, 7.21; N, 11.13; S, 8.49. Found: C, 60.66; H, 7.03; N, 10.85; S, 8.27.

EXAMPLE 96

N-[5-(1,1,2,2-tetramethylpropyl)-1,3,4-thiadiazol-2-yl]-2,6-dimethoxybenzamide

M.P. 245°–247° C. Yield 51%.

Analysis calculated for $C_{18}H_{25}N_3O_3S$: Theory: C, 59.48; H, 6.93; N, 11.56; S, 8.82. Found: C, 59.58; H, 6.70; N, 11.44; S, 8.93.

EXAMPLE 97

N-[5-(1-ethyl-1-methylpropyl)-1,3,4-thiadiazol-2-yl]-2,6-dimethoxy-4-(trifluoromethyl)benzamide M.P. 252°–254° C. Yield 20%.

Analysis calculated for $C_{18}H_{22}F_3N_3O_3S$: Theory: C, 51.79; H, 5.31; N, 10.07; S, 7.68; F, 13.65. Found: C, 51.52; H, 5.07; N, 9.97; S, 7.84; F, 13.70.

EXAMPLE 98

N-[5-(2-chloro-1,1-dimethylethyl)-1,3,4-thiadiazol-2-yl]-2,6-dimethoxybenzamide

M.P. 202°–204° C. Yield 69%.

Analysis calculated for $C_{15}H_{18}ClN_3O_3S$: Theory: C, 50.63; H, 5.06; N, 11.81; S, 9.00. Found: C, 50.86; H, 5.14; N, 11.90; S, 8.59.

EXAMPLE 99

N-[5-(1,1-dimethylpentyl)-1,3,4-thiadiazol-2-yl]-2,6-dimethoxybenzamide

M.P. 160°–162° C. Yield 30%.

Analysis calculated for $C_{18}H_{25}N_3O_3S$: Theory: C, 59.48; H, 6.93; N, 11.56; S, 8.82. Found: C, 59.69; H, 6.77; N, 11.34; S, 8.81.

EXAMPLE 100

N-(5-cyclohexyl-1,3,4-thiadiazol-2-yl)-2,6-dimethoxybenzamide

M.P. 206°–208° C. Yield 55%.

Analysis calculated for $C_{17}H_{21}N_3O_3S$: Theory: C, 58.77; H, 6.09; N, 12.09; S, 9.23. Found: C, 58.48; H, 6.30; N, 11.85; S, 9.42.

EXAMPLE 101

N-[5-(1,1-dimethylbutyl)-1,3,4-thiadiazol-2-yl]-2,6-dimethoxybenzamide

M.P. 167°–169° C. Yield 45%.

Analysis calculated for $C_{17}H_{23}N_3O_3S$: Theory: C, 58.43; H, 6.63; N, 12.02; S, 9.18. Found: C, 58.65; H, 6.79; N, 12.25; S, 8.87.

EXAMPLE 102

N-(5-cyclobutyl-1,3,4-thiadiazol-2-yl)-2,6-dimethoxybenzamide

M.P. 195°–197° C. Yield 65%.

Analysis calculated for $C_{15}H_{17}N_3O_3S$: Theory: C, 56.41; H, 5.37; N, 13.16; S, 10.04. Found: C, 56.13; H, 5.18; N, 12.89; S, 9.96.

EXAMPLE 103

N-[5-(1-ethyl-1-methylpropyl)-1,3,4-thiadiazol-2-yl]-4-methoxybenzamide

M.P. 138°–140° C. Yield 63%.

Analysis calculated for $C_{16}H_{21}N_3O_2S$: Theory: C, 60.16; H, 6.63; N, 13.16; S, 10.04. Found: C, 59.90; H, 6.47; N, 13.10; S, 9.82.

EXAMPLE 104

N-[5-(1-ethyl-1-methylpropyl)-1,3,4-thiadiazol-2-yl]-2,4,6-trimethyoxybenzamide

M.P. 183.5° C. Yield 65%.

Analysis calculated for $C_{18}H_{25}N_3O_4S$: Theory: C, 56.97; H, 6.64; N, 11.07; S, 8.45. Found: C, 57.15; H, 6.63; N, 10.86; S, 8.38.

EXAMPLE 105

N-[5-(1-propylcyclohexyl)-1,3,4-thiadiazol-2-yl]-2,6-dimethoxybenzamide

M.P. 190°–192° C. Yield 56%.

Analysis calculated for $C_{20}H_{27}N_3O_3S$: Theory: C, 61.67; H, 6.99; N, 10.79; S, 8.23; Found: C, 61.46; H, 6.76; N, 10.53; S, 8.44.

EXAMPLE 106

N-[5-(1,1,2-trimethyl-2-butenyl)-1,3,4-thiadiazol-2-yl]-2,6-dimethoxybenzamide

M.P. 215°–218° C. Yield 60%.

Analysis calculated for $C_{18}H_{23}N_3O_3S$: Theory: C, 59.81; L H, 6.41; N, 11.63; S, 8.87; Found: C, 59.54; H, 6.14; N, 11.55; S, 8.80.

EXAMPLE 107

N-[5-(1,1,2-trimethylbutyl)-1,3,4-thiadiazol-2-yl]-2,6-dimethoxybenzamide

M.P. 181°–183° C. Yield 69%.

Analysis calculated for $C_{18}H_{25}N_3O_3S$: Theory: C, 59.48; H, 6.93; N, 11.56; S, 8.82; Found: C, 59.46; H, 6.61; N, 11.36; S, 8.32.

EXAMPLE 108

N-[5-(1,1,3-trimethylbutyl)-1,3,4-thiadiazol-2-yl]-2,6-dimethoxybenzamide

M.P. 195°-197° C. Yield 66%.

Analysis calculated for $C_{18}H_{25}N_3O_3S$: Theory: C, 59.48; H, 6.93; N, 11.56; Found: C, 59.40; H, 6.77; N, 11.58.

EXAMPLE 109

N-[5-(1,1-dimethylpropyl)-1,3,4-thiadiazol-2-yl]-2,6-dimethoxybenzamide

M.P. 227°-229° C. Yield 67%.

Analysis calculated for $C_{16}H_{21}N_3O_3S$: Theory: C, 57.29; H, 6.31; N, 12.53; S, 9.56; Found: C, 57.09; H, 6.03; N, 12.27; S, 9.76.

EXAMPLE 110

N-[5-phenylmethyl-1,3,4-thiadiazol-2-yl]-2,6-dimethoxybenzamide

M.P. 190°-192° C. Yield 80%.

Analysis calculated for $C_{18}H_{17}N_3O_3S$: Theory: C, 60.83; H, 4.82; N, 11.82; S, 9.02; Found: C, 60.78; H, 4.86; N, 12.05; S, 8.88.

EXAMPLE 111

N-[5-(1,1-dimethylethyl)-1,3,4-thiadiazol-2-yl]-2,6-dimethoxybenzamide

M.P. 230°-232° C. Yield 77%.

Analysis calculated for $C_{15}H_{19}N_3O_3S$: Theory: C, 56.05; H, 5.96; N, 12.07; Found: C, 55.81; H, 5.98; N, 12.10.

EXAMPLE 112

N-[5-(1-ethyl-1,2,2-trimethylpropyl)-1,3,4-thiadiazol-2-yl]-2,6-dimethoxybenzamide M.P. 254°-256° C. Yield 56%.

Analysis calculated for $C_{19}H_{27}N_3O_3S$: Theory: C, 60.45; H, 7.21; N, 11.13; S, 8.49; Found: C, 60.33; H, 7.02; N, 10.95; S, 8.80.

EXAMPLE 113

N-(5-cyclopentyl-1,3,4-thiadiazol-2-yl)-2,6-dimethoxybenzamide

M.P. 180°-181° C. Yield 72%.

Analysis calculated for $C_{16}H_{19}N_3O_3S$: Theory: C, 57.64; H, 5.74; N, 12.60; Found: C, 57.70; H, 5.87; N, 12.37.

EXAMPLE 114

N-[3-(1,1-dimethylethyl)-1H-pyrazol-5-yl]-2,6-dimethoxybenzamide (A)

Preparation of 3-(1,1-dimethylethyl)-5-amino-1H-pyrazole

A suspension of 9.6 g of sodium hydride in 300 ml of tetrahydrofuran was stirred at 60° C. while a mixture of 23.2 g of methyl trimethylacetate and 8.2 g of acetonitrile was added in one portion. The reaction mixture was heated at reflux for five hours, and then cooled to room temperature and concentrated by evaporation of the solvent under reduced pressure. The product thus formed was dissolved in water and washed with dichloromethane. The aqueous layer was made acidic with 1N hydrochloric acid, and the acidic solution was extracted with fresh dichloromethane. The organic extracts were combined, washed with water, dried, and the solvent was removed by evaporation to give 14.0 g of cyanomethyl tert.-butyl ketone.

The ketone thus formed was dissolved in 150 ml of ethanol containing 32 g of hydrazine. The reaction mixture was heated at reflux for twelve hours, and then cooled to room temperature. Removal of the solvent by evaporation under reduced pressure provided a solid residue, which when triturated with 250 ml of petroleum ether, filtered and air dried, was identified as 12.5 g of 3-tert.-butyl-5-amino-1H-pyrazole.

M.P. 72°-74° C.

(B)

Acylation of the amino pyrazole with 2,6-dimethoxybenzoyl chloride.

To a stirred solution of 1.39 g of 3-tert.-butyl-5-amino-1H-pyrazole in 50 ml of benzene were added in one portion 2.01 g of 2,6-dimethoxybenzoyl chloride. The reaction mixture was heated at reflux for sixteen hours. The reaction mixture was then cooled, filtered, and the solvent was removed from the filtrate by evaporation. The residue was crystallized from ethyl acetate to provide 550 mg of N-[3-(1,1-dimethylethyl)-1H-pyrazol-5-yl]-2,6-dimethoxybenzamide.

M.P. 176°-178° C. Yield 18%.

Mass Spec. M+ Theory, 303; Found 304.

NMR (DMSOd$_6$): δ 1.35 (s, 9H, t-Bu); δ 3.76 (s, 6H, CH$_3$O—) δ 5.7-7.4 (m, 5H, aromatic); δ 10.9 (s, 1H, amide NH).

Analysis calculated for $C_{16}H_{21}N_3O_4$: Theory: C, 63.35; H, 6.98; N, 13.85; Found: C, 57.39; H, 6.34; N, 14.41.

The following N-pyrazolyl benzamides were prepared by the general procedure of Example 114.

EXAMPLE 115

N-[3-(1-ethyl-1-methylpropyl)-1H-pyrazol-5-yl]-2,6-dimethoxybenzamide

M.P. 222°-223° C. Yield 38%.

Analysis calculated for $C_{18}H_{25}N_3O_3$ Theory: C, 65.23; H, 7.60; N, 12.68; Found: C, 65.08; H, 7.61; N, 12.50.

EXAMPLE 116

N-[3-(1,1-dimethylbutyl)-1H-pyrazol-5-yl]-2,6-dimethoxybenzamide

M.P. 211°-213° C. Yield 27%.

Mass Spec. M+ Theory, 330; Found, 331.

NMR (CDCl$_3$): δ 0.7-1.6 (m, 13H, 1,1-dimethylbutyl); δ 3.81 (s, 6H, CH$_3$O); δ 6.51-6.77 (m, 3H, benzoyl aromatic); δ 7.2-7.5 (m, 2H, pyrazole aromatic); δ 7.8-8.1 (broad s, 1H, amide NH).

Analysis calculated for $C_{18}H_{24}N_3O_3$: Theory: C, 65.23; H, 7.60; N, 12.68; Found: C, 65.34; H, 6.79; N, 8.44.

EXAMPLE 117

N-[3-(1,1-dimethylpropyl)-1H-pyrazol-5-yl]-2,6-dimethoxybenzamide

M.P. 235°-237° C. Yield 37%.

Analysis calculated for $C_{17}H_{22}N_3O_3$: Theory: C, 64.33; H, 7.30; N, 13.24; Found: C, 64.20; H, 7.03; N, 12.99.

EXAMPLE 118

N-[5-(1-ethyl-1-methylpropyl)-4H-1,2,4-triazol-3-yl]-2,6-dimethoxybenzamide (A) Preparation of 5-(1-ethyl-1-methylpropyl)-3-amino-4H-1,2,4-triazole To a stirred solution of 13.1 g of potassium hydroxide in 40 ml of water were added dropwise a solution of 8.4 g of dicyandiamide in 50 ml of acetone. The reaction mixture was next cooled to 5° C., and then 14.0 g of 2-ethyl-2-methyl butyryl chloride were added dropwise over ten minutes. Following the addition, the reaction mixture was stirred at about 5° C. for fifteen minutes, and then diluted to 600 ml by the addition of water. The aqueous mixture was made acidic to pH 5.5 with glacial acetic acid, whereupon a white precipitate formed. The precipitate was collected by filtration, washed with water and air dried to give 5.45 g of N-(2-ethyl-2-methylbutyryl)dicyandiamide.

The product thus formed was suspended in 35 ml of water and stirred while a solution of 1.1 g of hydrazine in 25 ml of 2-ethoxyethanol was added in one portion. The reaction mixture was boiled for forty-five minutes, and then was cooled to room temperature and stirred for twelve hours. The precipitate which had formed was collected by filtration and was dried at 90° C. for two hours to provide 2.65 g of 1-[5-(1-ethyl-1-methylpropyl)-4H-1,2,4-triazol-3-yl]urea.

The pyrazolyl urea thus formed was added to 30 ml of water containing 3.0 g of sodium hydroxide. The reaction mixture was heated at reflux for twelve hours, and then made strongly acidic (pH 2.0) with nitric acid. The precipitate which formed was collected by filtration while the mixture was hot. After air drying the precipitate, it was identified as 2.65 g of 5-(1-ethyl-1-methylpropyl)-3-amino-4H-1,2,4-triazole, as the nitric acid salt.

M.P. 131° C.

The salt thus formed was dissolved in water and diluted with ammonia to pH 8. The solvent was then removed by evaporation and the residue was triturated with 25 ml of acetonitrile to give 1.1 g of 5-(1-ethyl-1-methylpropyl-3-amino-4H-1,2,4-triazole.

(B)

A solution of 1.1 g of the triazole and 1.43 g of 2,6-dimethoxybenzoyl chloride in 75 ml of toluene was heated at reflux for sixteen hours. The reaction mixture was cooled to room temperature and the solvent was removed by evaporation under reduced pressure to give a gum. The gum was chromatographed over a silica gel column, eluting with 50% ethyl acetate in hexane. The fractions shown by thin layer chromatographic analysis to contain the product were combined and the solvent was evaporated to provide 175 mg of N-[5-(1-ethyl-1-methylpropyl)-4H-1,2,4-triazol-3-yl]-2,6-dimethoxybenzamide.

M.P. 279°-280° C. Yield 8%.

Analysis calculated for $C_{17}H_{24}N_4O_3$: Theory: C, 61.45; H, 7.23; N, 16.87; Found: C, 60.94; H, 7.14; N, 15.99.

Mass Spec: M+ Theory, 332, Found, 333.

EXAMPLE 119

2,6-Dimethoxybenzoyl chloride was reacted with 3-amino-1H-1,2,4-triazole according to the procedure of Example 118 to provide N-(1H-1,2,4-triazol-3-yl)-2,6-dimethoxybenzamide.

M.P. 191°-193° C.

EXAMPLE 120

N-[3-(1,1-dimethylethyl)-5-isothiazolyl]-2,6-dimethoxybenzamide (A)

Preparation of 3-(1,1-dimethylethyl)-5-aminoisothiazole

A mixture of 50.0 g of cyanomethyl tert.-butyl ketone in 250 ml of ethanol containing 200 ml of ammonia was heated at 150° C. for sixteen hours. The reaction mixture was cooled to room temperature and the solvent was removed by evaporation under reduced pressure. The residue was dissolved in 330 ml of dichloromethane and diluted with 0.7 g of potassium hydroxide and 52 ml of hydrogen sulfide. The reaction mixture was heated at 80° C. for twenty-four hours, and then cooled and concentrated to dryness by evaporation of the solvent. The product was identified as 71 g of 2,2-dimethyl-3-amino-3-butenyl thiocarboxamide.

An 800 mg portion of the product thus obtained was dissolved in 25 ml of ethanol containing 5 ml of 30% hydrogen peroxide. The reaction mixture was stirred for twenty minutes, and then concentrated to dryness by evaporation to provide (3-(1,1-dimethyl-ethyl)-5-aminoisothiazole.

(B)

A solution of the 5-amino-isothiazole and 1.1 g of 2,6-dimethoxybenzoyl chloride in 50 ml of toluene was heated at reflux for two hours, during which time a precipitate formed. The precipitate was collected by filtration and dried to give 340 mg of N-[3-(1,1-dimethylethyl)-5-isothiazolyl]-2,6-dimethoxybenzamide.

M.P. 266°-267° C. Yield 30%.

Analysis claculated for $C_{16}H_{20}N_2O_3S$: Theory: C, 59.98; H, 6.29; N, 8.74; Found: C, 59.71; H, 6.15; N, 8.74.

EXAMPLE 121

N-[3-(1-ethyl-1-methylpropyl)-5-isothiazolyl]-2,6-dimethoxybenzamide was prepared according to Example 120.

M.P. 243°-244° C. Yield 70%.

Analysis calculated for $C_{18}H_{24}N_2O_3S$: Theory: C, 62.04; H, 6.94; N, 8.04; Found: C, 62.21; H, 6.73; N, 8.24.

EXAMPLE 122

N-[6-(1,1-dimethylethyl)pyridazin-3-yl]-2,6-dimethoxybenzamide (A)

Preparation of 3-amino-6-(1,1-dimethylethyl)pyridazine

A mixture of 5.8 of 3-chloro-6-(1,1-dimethylethyl)-pyridazine in 100 ml. of liquid ammonia was heated in a bomb at 200° C. for twenty-four hours. The reaction mixture was cooled to room temperature and filtered, and the solvent was removed from the filtrate by evaporation under reduced pressure to provide a black oil. The oil was chromatographed over silica gel, eluting with ethyl acetate and benzene. The appropriate fractions were combined and the solvent was removed therefrom by evaporation to give 2.08 g. of 3-amino-6-(1,1-dimethylethyl)pyridazine. M.P. 125°–132° C.

Analysis calculated for $C_8H_{13}N_3$: Theory: C, 63.54; H, 8.67; N, 27.79; Found: C, 63.74; H, 8.49; N, 27.53.

(B)

A solution of 600 mg. of 2,6-dimethoxybenzoyl chloride in 100 ml. of toluene containing 500 mg. of 3-amino-6-(1,1-dimethylethyl)pyridazine was heated at reflux under a nitrogen atmosphere for twenty-one hours. The reaction mixture was cooled to room temperature and the precipitate which formed was collected by filtration. The solid product was chromatographed over silica gel, eluting with ethyl acetate. Thin layer chromatographic analysis of the major product suggested that a minor amount of bis acylated product had been formed. The mixture was dissolved in 10 ml. of ethanol and 10 ml. of 2N sodium hydroxide, and the alkaline solution was heated at reflux for two hours. The reaction mixture was cooled and acidified by the addition of 1N hydrochloric acid.

The precipitate which formed was collected by filtration and recrystallized from hexane to provide 49 mg. of N-[6-(1,1-dimethylethyl)pyridazin-3-yl]-2,6-dimethoxybenzamide.

M.P. 163°–165° C. Yield 5%.

Analysis calculated for $C_{17}H_{21}N_3O_3$: Theory: C, 64.74; H, 6.71; N, 13.32; Found: C, 64.95; H, 6.41; N, 13.28.

Mass Spec. M+ Theory 315; Found 315.

Several additional compounds embraced by this invention have been prepared by reaction of an appropriately substituted benzoyl halide with a aryl amine. Typical examples follow.

EXAMPLE 123

N-[5-(1-ethyl-1-methylpropyl)-1,3,4-thiadiazol-2-yl]-2,6-di(methylthio)benzamide M.P. 194°–195° C. Yield 42%.

Analysis calculated for $C_{17}H_{23}N_3OS_3$: Theory: C, 53.51; H, 6.08; N, 11.01; S, 25.21; Found: C, 53.65; H, 6.12; N, 10.80; S, 25.40.

EXAMPLE 124

N-[5-(1-ethyl-1-methylpropyl)-1,3,4-thiadiazol-2-yl]-2-methoxy-6-methylthiobenzamide M.P. 184°–185° C. Yield 44.7%.

Analysis calculated for $C_{17}H_{23}N_3O_2S_2$: Theory: C, 55.86; H, 6.34; N, 11.50; S, 17.54; Found: C, 55.93; H, 6.17; N, 11.23; S, 17.37.

EXAMPLE 125

N-[5-(1-n-propylcyclopentyl)-1,3,4-thiadiazol-2-yl]-2,6-dimethoxybenzamide

M.P. 181°–183° C. Yield 56.5%.

Analysis calculated for $C_{19}H_{25}N_3O_3S$: Theory: C, 60.78; H, 6.71; N, 11.09; S, 8.54; Found: C, 61.08; H, 6.76; N, 11.40; S, 8.29.

EXAMPLE 126

N-[5-(1-(1-methylethenyl)cyclohexyl)-1,3,4-thiadiazol-2-yl]-2,6-dimethoxybenzamide M.P. 226°–228° C. Yield 53%.

Analysis calculated for $C_{20}H_{25}N_3O_3S$: Theory: C, 61.99; H, 6.50; N, 10.84; S, 8.27; Found: C, 62.20; H, 6.52; N, 10.55; S, 8.04.

EXAMPLE 127

N-[5-(1-isopropylcyclohexyl)-1,3,4-thiadiazol-2-yl]-2,6-dimethoxybenzamide

M.P. 224°–226° C. Yield 53.6%.

Analysis calculated for $C_{20}H_{27}N_3O_3S$: Theory: C, 61.67; H, 6.99; N, 10.79; S, 8.23; Found: C, 61.47; H, 6.75; N, 10.53; S, 8.21.

EXAMPLE 128

N-[5-(1-ethyl-1,2-dimethyl-2-propenyl)-1,3,4-thiadiazol-2-yl]-2,6-dimethoxybenzamide M.P. 207°–209° C. Yield 10%.

Analysis calculated for $C_{18}H_{23}N_3O_3S$: Theory: C, 59.81; H, 6.41; N, 11.63; S, 8.87; Found: C, 59.65; H, 6.40; N, 11.56; S, 9.02.

EXAMPLE 129

N-[5-(1-ethyl-1-methylpropyl)-1,3,4-thiadiazol-2-yl]-2-methoxy-4-trifluoromethyl-6-methylthiobenzamide M.P. 224°–225° C. Yield 26.2%.

Analysis calculated for $C_{18}H_{22}F_3N_3O_2S_2$: Theory: C, 49.87; H, 5.12; N, 9.69; F, 13.15; S, 14.79; Found: C, 49.65; H, 4.92; N, 9.90; F, 13.40; S, 14.81.

EXAMPLE 130

N-[5-(1-methylethyl)-1,3,4-thiadiazol-2-yl]-2,6-dimethoxybenzamide.

M.P. 164°–166° C. Yield 29%.

Analysis calculated for $C_{14}H_{17}N_3O_3S$: Theory: C, 54.72; H, 5.54; N, 13.68; S, 10.42; Found: C, 54.65; H, 5.52; N, 13.62; S, 10.90.

EXAMPLE 131

N-(5-Cyclopropyl-1,3,4-thiadiazol-2-yl)-2,6-dimethoxybenzamide

M.P. 194°–196° C. Yield 52%.

Analysis calculated for $C_{14}H_{15}N_3O_3S$: Theory: C, 55.07; H, 4.95; N, 13.76; S, 10.50; Found: C, 55.37; H, 5.18; N, 13.66; S, 10.29.

EXAMPLE 132

N-(3-ethyl-5-isoxazolyl)-4-2,6-dimethoxybenzamide

M.P. 132°–134° C. Yield 56.6%.

Analysis calculated for $C_{14}H_{16}N_2O_4$: Theory: C, 60.86;1 H, 5.84; N, 10.14; Found: C, 60.77; H, 5.81; N, 10.03.

EXAMPLE 133

N-(3-methyl-5-isoxazolyl)-2,6-dimethoxybenzamide

M.P. 155°–158° C. Yield 70%.

Analysis calculated for $C_{13}H_{14}N_2O_4$: Theory: C, 59.54; H, 5.38; N, 10.68; O, 24.40. Found: C, 59.85; H, 5.67; N, 10.40; O, 24.63.

EXAMPLE 134

N-(3-n-hexyl-5-isoxazolyl)-2,6-dimethoxybenzamide

M.P. 119°–121° C.

Analysis calculated for $C_{18}H_{22}N_2O_4$: Theory: C, 65.04; H, 7.28; N, 8.43; Found: C, 64.92; H, 7.43; N, 8.16.

EXAMPLE 135

N-(3-ethyl-5-isoxazolyl)-2,6-dimethoxybenzamide

M.P. 132°–134° C. Yield 56.6%.

Analysis calculated for $C_{14}H_{16}N_2O_4$: Theory: C, 60.86; H, 5.84; N, 10.14; Found: C, 60.77; H, 5.81; N, 10.03.

EXAMPLE 136

N-[5-(1-ethyl-1-methylpropyl)-1,3,4-oxadiazol-2-yl]-2,6-dimethoxybenzamide

M.P. 190°–192° C. Yield 16%

Analysis calculated for $C_{17}H_{23}N_3O_3$: Theory: C, 61.36; H, 6.91; N, 12.61; Found: C, 61.99; H, 6.84; N, 13.29.

EXAMPLE 137

N-[3-(1,1-dimethylethyl)-1,2,4-thiadiazol-5-yl]-2,6-dimethoxybenzamide

M.P. 180°–182° C. Yield 65.7%.

Analysis calculated for $C_{15}H_{19}N_3O_3S$: Theory: C, 56.06; H, 5.96; N, 13.07; S, 9.98. Found: C, 56.07; H, 5.72; N, 12.89; S, 10.25.

EXAMPLE 138

N-[3-(1,1-dimethylethyl-1,2,4-oxadiazol-5-yl]-2,6-dimethoxybenzamide

M.P. 207°–209° C.

Analysis calculated for $C_{15}H_{19}N_3O_4$: Theory: C, 59.01; H, 6.27; N, 13.76; Found: C, 59.18; H, 6.49; N, 13.85.

EXAMPLE 139

N-[3-(1-ethyl-1-methylpropyl)-5-isoxazolyl]-2,3,5-triiodobenzamide

M.P. 167°–168° C.

Analysis calculated for $C_{16}H_{17}I_3N_2O_2$; Theory: C, 29.56; H, 2.64; N, 4.31. Found: C, 29.80; H, 2.79; N, 4.29.

EXAMPLE 140

N-[3-(1-ethyl-1-methylpropyl)-5-isoxazolyl]-2,6-di(methylthio)benzamide

M.P. 114°–116° C. Yield 21%.

Analysis calculated for $C_{18}H_{24}N_2O_2S_2$; Theory: C, 59.31; H, 6.64; N, 7.68; S, 17.59. Found: C, 59.20; H, 6.80; N, 7.50; S, 17.51.

EXAMPLE 141

N-[3-(1-methoxymethyl)-1-methylpropyl)-5-isoxazolyl]-2,6-dimethoxybenzamide

M.P. 164°–166° C. Yield 34%.

Analysis calculated for $C_{18}H_{24}N_2O_5$; Theory: C, 62.05; H, 6.94; N, 8.04. Found: C, 62.34; H, 6.76; N, 8.06.

EXAMPLE 142

N-[3-(1-ethyl-1-methylpropyl)-4-methyl-5-isoxazolyl]-2,6-dimethoxybenzamide

M.P. 179°–180° C. Yield 37%.

Analysis calculated for $C_{19}H_{26}N_2O_4$; Theory: C, 65.88; H, 7.57; N, 8.09. Found: C, 65.62; H, 7.36; N, 7.86.

EXAMPLE 143

N-[5-(1-ethyl-1-methylpropyl)-1,3,4-oxadiazol-2-yl]-2,6-dimethoxybenzamide

M.P. 190°–192° C. Yield 30%.

Analysis calculated for $C_{17}H_{23}N_3O_4$; Theory: C, 61.26; H, 6.91; N, 12.61. Found: C, 61.99; H, 6.84; N, 13.29.

EXAMPLE 144

N-[5-(1-methylcyclobutyl)-1,3,4-thiadiazol-2-yl]-2,6-dimethoxybenzamide

M.P. 218°–220° C. Yield 50.7%.

Analysis calculated for $C_{16}H_{19}N_3O_3S$; Theory: C, 57.64; H, 5.74; N, 12.60; S, 9.62. Found: C, 57.87; H, 5.87; N, 12.84; S, 9.42.

EXAMPLE 145

N-[5-(1,1,2-trimethyl-2-propenyl)-1,3,4-thiadiazol-2-yl]-2,6-dimethoxybenzamide

M.P. 236°–238° C. Yield 46%.

Analysis calculated for $C_{17}H_{21}N_3O_3S$; Theory: C, 58.77; H, 6.09; N, 12.09; S, 9.23. Found: C, 58.54; H, 6.24; N, 12.19; S, 9.10.

EXAMPLE 146

N-[5(1-ethyl-1-methylpropyl)-1,3,4-thiadiazol-2-yl]-2,6-dimethoxy-3-bromobenzamide M.P. 163°–165° C. Yield 35%.

Analysis calculated for $C_{17}H_{22}BrN_3O_3S$; Theory: C, 47.67; H, 5.18; N, 9.81; S, 7.49; Br, 18.65. Found: C, 47.87; H, 5.31; N, 10.02; S, 7.69; Br, 18.77.

EXAMPLE 147

N-[5-(1,1-dimethyl-2-propenyl)-1,3,4-thiadiazol-2-yl]-2,6-dimethoxybenzamide

M.P. 225°–228° C. Yield 52%.

Analysis calculated for $C_{19}H_{19}N_3O_3S$; Theory: C, 57.64; H, 5.74; N, 12.60; S, 9.62. Found: C, 57.83; H, 5.91; N, 12.87; S, 9.58.

EXAMPLE 148

N-(5-cycloheptyl-1,3,4-thiadiazol-2-yl)-2,6-dimethoxybenzamide

M.P. 213°–215° C. Yield 80.5%.

Analysis calculated for $C_{18}H_{23}N_3O_3S$; Theory: C, 59.81; H, 6.41; N, 11.63; S, 8.87. Found: C, 59.91; H, 6.22; N, 11.71; S, 8.67.

EXAMPLE 149

N-[5-(1-ethyl-1-methylpentyl)-1,3,4-thiadiazol-2-yl]-2,6-dimethoxybenzamide

M.P. 141°–143° C. Yield 48.8%.

Analysis calculated for $C_{19}H_{27}N_3O_3S$; Theory: C, 60.45; H, 7.21; N, 11.13; S, 8.49. Found: C, 60.49; H, 7.08; N, 11.12; S, 8.29.

EXAMPLE 150

N-[5-(1-ethyl-1-propylbutyl)-1,3,4-thiadiazol-2-yl]-2,6-dimethoxybenzamide

M.P. 216°–218° C. Yield 47.9%.

Analysis calculated for $C_{20}H_{29}N_3O_3S$; Theory: C, 61.35; H, 7.47; N, 10.73; S, 8.19. Found: C, 61.65; H, 7.54; N, 10.46; S, 8.31.

EXAMPLE 151

N-[5-(1-ethyl-1,3-dimethylbutyl)-1,3,4-thiadiazol-2-yl]-2,6-dimethoxybenzamide

M.P. 166°–168° C. Yield 17.6%.

Analysis calculated for $C_{19}H_{27}N_3O_3S$; Theory: C, 60.45; H, 7.21; N, 11.13; S, 8.49. Found: C, 60.54; H, 7.21; N, 11.07; S, 8.68.

EXAMPLE 152

N-[5-(1-ethyl-1-methylhexyl)-1,3,4-thiadiazol-2-yl]-2,6-dimethoxybenzamide

M.P. 107°–109° C. Yield 36.9%.

Analysis calculated for $C_{20}H_{29}N_3O_3S$; Theory: C, 61.35; H, 7.47; N, 10.73; S, 8.19. Found: C, 61.53; H, 7.23; N, 10.97; S, 8.38.

EXAMPLE 153

N-[5-(1-ethyl-1,2-dimethylpropyl)-1,3,4-thiadiazol-2-yl]-2,6-dimethoxybenzamide

M.P. 205°–207° C. Yield 48.8%.

Analysis calculated for $C_{18}H_{25}N_3O_3S_1$; Theory: C, 59.48; H, 6.93; N, 11.56; S, 8.82. Found: C, 59.68; H, 7.00; N, 11.64; S, 9.04.

EXAMPLE 154

N-[5-(2-methoxy-1,1-dimethylpropyl)-1,3,4-thiadiazol-2-yl]-2,6-dimethoxybenzamide M.P. 202°–203° C. Yield 25%.

Analysis calculated for $C_{17}H_{23}N_3O_4S$; Theory: C, 55.87; H, 6.34; N, 11.50; S, 8.77. Found: C, 55.87; H, 6.24; N, 11.31; S, 9.02.

EXAMPLE 155

N-[5-(1-methyl-1-(methylthio)propyl)-1,3,4-thiadiazol-2-yl]-2,6-dimethoxybenzamide M.P. 223°–224° C. Yield 52.4%.

Analysis calculated for $C_{16}H_{21}N_3O_3S_2$; Theory: C, 52.29; H, 5.76; N, 11.43; S, 17.45. Found: C, 52.57; H, 5.87; N, 11.65; S, 17.62.

EXAMPLE 156

N-[5-(1-ethyl-1,2-dimethylbutyl)-1,3,4-thiadiazol-2-yl]-2,6-dimethoxybenzamide

M.P. 197°–199° C. Yield 14.9%.

Analysis calculated for $C_{19}H_{27}N_3O_3S$; Theory: C, 60.45; H, 7.21; N, 11.33; S, 8.49. Found: C, 60.28; H, 6.94; N, 10.93; S, 8.74.

EXAMPLE 157

N-[6-(1-ethyl-1-methylpropyl)-pyridazin-3-yl]-2,6-dimethoxybenzamide

M.P. 145°–147° C. Yield 68%.

Analysis calculated for $C_{19}H_{25}N_3O_3$; Theory: C, 66.45; H, 7.34; N, 12.24. Found: C, 66.71; H, 7.55; N, 12.08.

EXAMPLE 158

N-[6-(1-ethylcyclohexyl)-pyridazin-3-yl]-2,6-dimethoxybenzamide

M.P. 103°–112° C.

EXAMPLE 159

N-[5-(1,1-dimethyl-2-butenyl)-1,3,4-thiadiazol-2-yl]-2,6-dimethoxybenzamide

M.P. 204°–207° C. Yield 67%.

Analysis calculated for $C_{17}H_{21}N_3O_3S$; Theory: C, 58.77; H, 6.09; N, 12.09; S, 9.23. Found: C, 58.90; H, 6.11; N, 12.00; S, 8.97.

EXAMPLE 160

N-[5-(1-ethyl-1-methylpropyl)-1,3,4-thiadiazol-2-yl]-2,3,6-trichlorobenzamide

M.P. 220°–222° C. Yield 20%.

Analysis calculated for $C_{15}H_{16}Cl_3N_3OS$; Theory: C, 45.87; H, 4.11; N, 10.70; S, 8.16; Cl, 27.08. Found: C, 45.72; H, 4.36; N, 10.60; S, 8.36; Cl, 27.39.

EXAMPLE 161

N-[5-(2,2-dichloro-1,1-dimethylethyl)-1,3,4-thiadiazol-2-yl]-2,6-dimethoxybenzamide M.P. 211°–213° C. Yield 32.7%.

Analysis calculated for $C_{15}H_{17}Cl_2N_3O_3S$; Theory: C, 46.16; H, 4.39; N, 10.77; S, 8.22; Cl, 18.17. Found: C, 46.29; H, 4.47; N, 10.63; S, 8.42; Cl, 18.25.

EXAMPLE 162

N-[3-(1,1-dimethylethyl)-1,2,4-oxadiazol-5-yl]-2,6-dimethoxybenzamide

M.P. 207°–209° C.

Analysis calculated for $C_{15}H_{19}N_3O_4$; Theory: C, 59.01; H, 6.27; N, 13.76. Found: C, 59.18; H, 6.49; N, 13.85.

EXAMPLE 163

N-[3-(1-ethyl-1-methylpropyl)-5-isoxazolyl]-4-chlorobenzamide

M.P. 162°–164° C. Yield 10%.

Analysis calculated for $C_{16}H_{19}ClN_2O_2$; Theory: C, 62.64; H, 6.24; N, 9.13. Found: C, 62.68; H, 6.42; N, 9.24.

EXAMPLE 164

N-[3-(1-ethyl-1-(methoxymethyl)propyl)-5-isoxazolyl]-2,6-dimethoxybenzamide

M.P. 167°–168° C. Yield 26%.

Analysis calculated for $C_{19}H_{26}N_2O_5$; Theory: C, 62.97; H, 7.23; N, 7.73. Found: C, 63.23; H, 7.00; N, 7.76.

EXAMPLE 165

N-[5-(2-chloro(1-chloromethyl)-1-methylethyl)-1,3,4-thiadiazole-2-yl]-2,6-dimethoxybenzamide M.P. 228°–230° C. Yield 49.3%.

Analysis calculated for $C_{15}H_{17}Cl_2N_3O_3S$; Theory: C, 46.16; H, 4.39; N, 10.77; S, 8.22; Cl, 18.17. Found: C, 46.36; H, 4.23; N, 10.79; S, 8.36; Cl, 18.37.

EXAMPLE 166

N-[5-(1-ethyl-1-(methylthio)propyl)-1,3,4-thiadiazol-2-yl]-2,6-dimethoxybenzamide M.P. 216°–218° C. Yield 65.5%.

Analysis calculated for $C_{17}H_{23}N_3O_3S_2$; Theory: C, 53.52; H, 6.08; N, 11.01; S, 16.81. Found: C, 53.75; H, 5.90; N, 10.97; S, 17.05.

EXAMPLE 167

N-[5-(1-ethyl-1-[(methylthio)methyl]propyl)-1,3,4-thiadiazol-2-yl]-2,6-dimethoxybenzamide M.P. 209°–211° C. Yield 30.7%.

Analysis calculated for $C_{18}H_{25}N_3O_3S_2$; Theory: C, 54.66; H, 6.37; N, 10.62; S, 16.21. Found: C, 54.87; H, 6.53; N, 10.49; S, 16.47.

EXAMPLE 168

N-[5-(1-methyl-1-[(methylthio)methyl]propyl)-1,3,4-thiadiazol-2-yl]-2,6-dimethoxybenzamide M.P. 181°–183° C. Yield 60.7%.

Analysis calculated for $C_{17}H_{23}N_3O_3S_2$; Theory: C, 53.52; H, 6.08; N, 11.01; S, 16.81. Found: C, 53.56; H, 6.33; N, 10.80; S, 16.61.

EXAMPLE 169

N-[5(4)-(1,1-dimethylethyl)-2-imidazolyl]-2,6-dimethoxybenzamide (A)

Preparation of 2-amino-5-(1,1-dimethylethyl)imidazole

To a stirred solution of 6.8 g of aminomethyl-(1,1-dimethylethyl)ketone, as the hydrochloride salt, in 30 ml of water were added portionwise 5.0 g of cynamide. The pH of the reaction mixture was adjusted to 6.0 with 1N sodium hydroxide, and then the mixture was heated to 90° C. and stirred for fifty-five minutes. The reaction mixture was next cooled to room temperature, diluted with 100 ml. of water, and extracted several times with diethyl ether. The aqueous layer was made alkaline with ammonium hydroxide, and again extracted several times with diethylether. The extracts from the alkaline mixture were combined and concentrated to dryness to provide a solid residue. The residue thus obtained was dissolved in 20 ml of 6N hydrochloric acid and heated at reflux for sixteen hours. The reaction mixture was cooled, concentrated to an oil by evaporation of the solvent, and the oil was dissolved in water and made alkaline to pH 8.5. The alkaline mixture was extracted several times with diethyl ether. The etheral extracts were combined, washed with water, dried, and the solvent was removed by evaporation under reduced pressure to provide 0.5 g of 5-(1,1-dimethylethyl)-2-aminoimidazole.

NMR (DMSOd$_6$): $\delta$1.17 (s, 9H, t-butyl); $\delta$5.47 (NH$_2$, NH), $\delta$6.1 (s, 1H, aromatic).

(B)

A mixture of 0.5 g of the 2-aminoimidazole thus prepared and 0.72 g of 2,6-dimethoxybenzoyl chloride in 50 ml of benzene was heated at reflux for sixteen hours. The reaction mixture was then cooled and the solvent was removed by evaporation under reduced pressure. The product was dissolved in 25 ml of ethanol, and again the solvent was removed by evaporation under reduced pressure to provide an oil. The oil was purified by preparative thin layer chromatography to afford 25 mg of
N-[5-(4)-(1,1-dimethylethyl)-2-imidazolyl]-2,6-dimethoxybenzamide.

M.P. 170°–173° C.

NMR (DMSOd$_6$) $\delta$1.2 (s, 9H, t-butyl); $\delta$3.74 (s, 6H, methoxy); $\delta$6.38–7.41 (m, 5H, aromatic).

EXAMPLE 170

N-[5-(1-ethyl-1-methylpropyl)-1,3,4-thiadiazol-2-yl]-2,6-dimethoxythiobenzamide

Example 61 describes the synthesis of N-[5-(1-ethyl-1-methylpropyl)-1,3,4-thiadiazol-2-yl]-2,6-dimethoxybenzamide. Five grams of this benzamide were dissolved in 75 ml of dioxane and stirred while 4.7 g of phosphorus pentachloride were added to the reaction mixture. The solution was heated at reflux under a nitrogen atmosphere for three hours. The reaction mixture next was cooled and filtered, and the filtrate was added to 200 ml of water. The aqueous mixture was stirred for about one hour at room temperature. The precipitated solid that had formed was collected by filtration and air dried to give a yellow solid. The product was identified as a mixture of starting material and desired product. The mixture was separated by high pressure liquid chromatography, using fifty percent ethyl acetate/hexane, v/v, as the solvent. The faster moving material was collected and identified as N-[5-(1-ethyl-1-methylpropyl)-1,3,4-thiadiazol-2-yl]-2,6-dimethoxythiobenzamide.

M.P. 202°–204° C. Yield 17.6%.

Analysis calculated for $C_{17}H_{23}N_3O_2S_2$; Theory: C, 55.86; H, 6.34; N, 11.50; S, 17.51. Found: C, 55.71; H, 6.51; N, 11.32; S, 17.72.

EXAMPLE 171

N-[3-(1-ethyl-1-methylpropyl)-5-isoxazolyl]-2,6-dimethoxythiobenzamide

A suspension of 6.0 g of N-[3-(1-ethyl-1-methylpropyl)-5-isoxazolyl]-2,6-dimethoxybenzamide (prepared as described in Example 1) and 7.28 g of [2,4-bis(4-methoxyphenyl)-1,3-dithia-2,4-diphosphetane-2,4-disulfide (Lawesson's Reagent) in 150 ml of toluene was heated at reflux until it turned orange color. The reaction mixture was then cooled to room temperature and the solvent was removed by evaporation under reduced pressure to provide a solid. The solid was suspended in dichloromethane and filtered. The solvent was removed from the filtrate by evaporation under reduced pressure to afford a reddish orange viscous oil. The oil was purified by chromatography over a column of dry-packed silica gel (500 g), and the column was eluted with dichloromethane. Fractions containing the major component were combined and the solvent was removed by evaporation under reduced pressure to provide 4.1 g of a yellow solid identified as N-[3-(1-ethyl-1-methylpropyl)-5-isoxazolyl]-2,6-dimethoxythiobenzamide.

M.P. 110°–112° C.

Analysis calculated for $C_{18}H_{24}N_2O_3S$; Theory: C, 62.04; H, 6.94; N, 8.04; S, 9.20. Found: C, 62.00; H, 7.09; N, 7.96; S, 8.91.

EXAMPLE 172

N-[3-((2-methoxy-1-methoxymethyl)-1-methylethyl)-5-isoxazolyl]-2,6-dimethoxybenzamide A suspension of 9.5 g of thionyl chloride in 300 ml of benzene contained 7.27 g of 2,6-dimethoxybenzoic acid was heated at 65° C. for eighteen hours to provide a clear yellow solution. The solvent was removed by evaporation under reduced pressure, and 100 ml of fresh benzene were added, followed by the addition to the mixture of 8.6 g of 3-[(2-methoxy-1-methoxymethyl)-1-methylethyl]-5-aminoisoxazole. The reaction mixture was heated to reflux for eighteen hours, and then cooled. The solvent was removed by evaporation to provide a solid that was then dissolved in dichloromethane. The organic layer was extracted with 200 ml of 1N sodium hydroxide, and the aqueous alkaline extract was cooled in an ice bath and acidified with 2N hydrochloric acid to provide a solid precipitate. The aqueous mixture was extracted with dichloromethane, and the organic extract was washed with brine and dried. Evaporation of the solvent provided a white solid. The solid was crystallized from dichloromethane and diethyl ether to give 8.42 g (77% yield) of N-[3-((2-methoxy-1-methoxymethyl)-1-methylethyl)-5-isoxazolyl]-2,6-dimethoxybenzamide.

M.P. 164°–166° C.

Analysis calculated for $C_{18}H_{24}N_2O_6$; Theory: C, 59.33; H, 6.64; N, 7.69. Found: C, 59.50; H, 6.46; N, 7.63.

EXAMPLE 173

N-[5-((2-acetoxy-1-acetoxymethyl)-1-methylethyl)-1,3,4-thiadiazol-2-yl]-2,6-dimethoxybenzamide A solution of 300 mg of 2,6-dimethoxybenzoyl chloride in 20 ml of toluene containing 300 mg of 2-amino-5-[(2-acetoxy-1-acetoxymethyl)-1-methylethyl]-1,3,4-thiadiazole was heated at reflux for eighteen hours. The reaction mixture was cooled to room temperature and diluted with pentane. A solid precipitate which formed was collected by filtration and air dried to give N-[5-((2-acetoxy-1-acetoxymethyl)-1-methylethyl)-1,3,4-thiadiazol-2-yl]-2,6-dimethoxybenzamide in 3% yield.

M.P. 115°–125° C. (dec.).

EXAMPLE 174

N-[3-((2-methoxy-1-methoxymethyl)-1-methylethyl)-5-isoxazolyl]-2,6-dimethoxybenzamide, sodium salt To a stirred solution of 3.64 g of N-[3-((2-methoxy-1-methoxymethyl)-1-methylethyl)-5-isoxazolyl]-2,6-dimethoxybenzamide (from Example 172) in 75 ml of tetrahydrofuran was added portion-wise over five minutes 432 mg of sodium hydride. Following complete addition, the reaction mixture became slightly yellow clear solution, and then a precipitate started to form. The mixture was cooled to 15° C., and then filtered. The precipitate was washed with fresh tetrahydrofuran, and then dried at 100° C. to provide 2.25 g of hygroscopic solid identified as N-[3-((2-methoxy-1-methoxymethyl)-1-methylethyl)-5-isoxazolyl]-2,6-dimethoxybenzamide, sodium salt.

M.P. 82°–84° C.

Analysis calculated for $C_{18}H_{23}N_2O_6Na$; Theory: C, 54.68; H, 5.86; N, 7.09. Found: C, 54.93; H, 6.25; N, 6.80.

EXAMPLE 175

N-[3-(1-ethyl-1-methylpropyl)-5-isoxazolyl]-2,6-dimethoxybenzamide, sodium salt

A solution of 3.32 g of the benzamide of Example 1 in 20 ml of dichloromethane and 20 ml of diethyl ether was stirred at room temperature under a nitrogen atmosphere while 432 mg of sodium hydride were added portion-wise over about two minutes. A white precipitate formed as the solution was stirred. The precipitate was collected by filtration, washed with diethyl ether and dried in a vacuum at 60° C. to provide 2.94 g of N-[3-(1-ethyl-1-methylpropyl)-5-isoxazolyl]-2,6-dimethoxybenzamide sodium salt.

M.P. 218°–220° C. 83% Yield.

EXAMPLE 176

N-[5-(2-methyl-1,3-dithian-2-yl)-1,3,4-thiadiazol-2-yl]-2,6-dimethoxybenzamide

A solution of 1.0 g of 2,6-dimethoxybenzoyl chloride in 50 ml of toluene containing 1.0 g of 2-amino-5-(2-methyl-1,3-dithian-2-yl)-1,3,4-thiadiazole was heated at reflux for fifteen hours. The reaction mixture was then cooled to room temperature and diluted with pentane, whereupon a white precipitate formed. The precipitate was collected by filtration and identified as N-[5-(2-methyl-1,3-dithian-2-yl)-1,3,4-thiadiazol-2-yl]-2,6-dimethoxybenzamide.

M.P. 259° C. (dec). Yield 2%.

EXAMPLE 177

N-[5-(1,3-dithian-2-yl)-1,3,4-thiadiazol-2-yl]-2,6-dimethoxybenzamide

A solution of 1.0 g. of 2,6-dimethoxybenzoyl chloride and 1.1 g of 2-amino-5-(1,3-dithian-2-yl)-1,3,4-thiadiazole in 20 ml of toluene was heated at reflux for eighteen hours under a nitrogen atmosphere. The reaction mixture was cooled to room temperature and the solvent was removed by evaporation under reduced pressure to provide a white solid. The solid was chromatographed over silica gel to provide 1.2 g (60% yield) of N-[5-(1,3-dithian-2-yl)-1,3,4-thiadiazol-2yl]-2,6-dimethoxybenzamide.

M.P. 200°–202° C.

The benzamides provided by this invention have been found to display useful herbicidal activity against a variety of weed species commonly occuring in areas utilized for growing desired crops such as the cereal grains and the like. The selective herbicidal activity of the compounds has been analyzed in a number of standard greenhouse and open field tests. One such test was a broad spectrum greenhouse test carried out by filling square plastic pots with a sterilized sandy loam soil and planting seeds of tomato, large crabgrass and pigweed. Each pot was fertilized with 158 mg of a 23-21-17 fertilizer four days before treatment with test compound.

The test compounds were formulated for application by dissolving each compound in a solution comprising 100 ml of acetone and 100 ml of ethanol plus 1.174 g of Toximul R and 0.783 g of Toximul S. (Toximul R and Toximul S are proprietary blends of anionic and nonionic surfactants manufactured by Stepan Chemical Company, Northfield, Ill.). Each test compound was dissolved in the diluent at the rate of 20 mg per 2 ml of solvent, and then the solution was diluted to 8 ml with deionized water. The formulated compounds were applied to the planted pots at an effective rate of 15 pounds per acre.

Test compounds were applied postemergence to some planted pots and preemergence to others. The postemergence applications were made by spraying the solution containing the test compound over the emerged plants about twelve days after the seeds were planted. Preemergence applications were sprayed on the soil one day after the seeds were planted.

Following application of the test compounds, the pots were placed in a greenhouse and watered as necessary. Observations were conducted about 10–13 days following application of the test compounds, and untreated control plants were used as standards in each observation. The degree of herbicidal activity of the test compounds was determined by rating the treated plants on a scale of 1-5. On this scale, "1" indicates no plant injury; "2" is slight injury; "3" is moderate plant injury; "4" is severe injury and "5" is death of the plant or no seedling emergence. The type of plant injury sustained by the plants was tabulated using the following code letters:

A=abscission of leaves
B=burned
C=chlorosis
D=death
E=epinasty
F=formative effects
G=dark green
I=increased plant growth
L=local necrosis
N=no germination
P=purple pigmentation
R=reduced germination
S=stunting
U=unclassified injury Compounds causing plant injuries rated 4 or 5 are considered very active, while compounds rated 2 or 3 are considered moderately active.

Table I below presents the herbicidal activity of typical benzamides of the invention when evaluated in a broad spectrum screen as described above.

TABLE I

| Compound of Example No. | Preemergence | | | Postemergence | | |
|---|---|---|---|---|---|---|
| | Tomato | Large Crabgrass | Pigweed | Tomato | Large Crabgrass | Pigweed |
| 1 | 5N | 5N | 5N | 4BS | 4BS | 4BS |
| 2 | 1 | 1 | 5N | 1 | 1 | 1 |
| 3 | 4RS | 3S | 4RS | 1 | 1 | 1 |
| 4 | 1 | 1 | 5N | 5D | 1 | 4CBS |
| 5 | 1 | 1 | 3RS | 4CBS | 4BS | 5D |
| 9 | 5N | 2CBS | 5N | 2CBS | 1 | 1 |
| 10 | 3RS | 3RS | 4RS | 3GS | 1 | 1 |
| 14 | 5N | 5N | 5N | 4BS | 2BS | 4BS |
| 16 | 5N | 4RS | 5N | 4BS | 3CBS | 4CBS |
| 17 | 5N | 4S | 5N | 3SB | 2SB | 3SB |
| 18 | 2S | 2S | 3S | 5D | 2S | 4SB |
| 21 | 1 | 1 | 5N | 1 | 1 | 1 |
| 23 | 5N | 5N | 1 | 2S | 1 | 1 |
| 24 | 5N | 5N | 5N | 4CFS | 2BS | 3FS |
| 25 | 5N | 5N | 5N | 5D | 1 | 5D |
| 29 | 5N | 5N | 5N | 3FS | 1 | 2FS |
| 33 | 1 | 1 | 5N | 1 | 1 | 1 |
| 37 | 1 | 5D | 1 | 1 | 2CBS | 1 |
| 54 | 5N | 5N | 5N | 4CBS | 1 | 4CBS |
| 55 | 1 | 5N | 5N | 4FS | 2S | 3FS |
| 57 | 1 | 4RS | 4RS | 1 | 1 | 1 |
| 58 | 5N | 5N | 5N | 2FS | 1 | 1 |
| 61 | 5N | 4RS | 5N | 4BS | 1 | 4BS |
| 64 | 4RS | 1 | 5N | 2FS | 1 | 1 |
| 67 | 1 | 2S | 5N | 1 | 1 | 1 |
| 69 | 1 | 1 | 1 | 1 | 2BS | 2BS |
| 71 | 5N | 1 | 5N | 4CBS | 2PBS | 4BS |
| 73 | 4RS | 2RS | 4RS | 4BS | 2PBS | 4BS |
| 74 | 5N | 5N | 5N | 3BS | 2BS | 3BS |
| 75 | 4RS | 1 | 5N | 2CBS | 1 | 1 |
| 76 | 5N | 5N | 5N | 4BS | 2BS | 5D |
| 79 | 3S | 4S | 3S | 1 | 1 | 1 |
| 80 | 5N | 3RS | 5N | 1 | 1 | 1 |
| 82 | 5N | 1 | 5N | 2CS | 1 | 1 |
| 86 | 1 | 1 | 1 | 2CBS | 2BS | 3BS |
| 90 | 5N | 5N | 5N | 4CFS | 2BS | 3FS |
| 95 | 5N | 5N | 5N | 4BS | 3BS | 4FS |
| 98 | 1 | 1 | 5N | 1 | 1 | 1 |
| 99 | 1 | 1 | 5N | 1 | 1 | 1 |
| 105 | 4RS | 1 | 4RS | 1 | 1 | 3RS |
| 107 | 4RS | 3RS | 4RS | 2S | 2BS | 2FS |
| 108 | 3RS | 2S | 5N | 1 | 1 | 2BS |
| 109 | 5N | 3RS | 5N | 4FS | 2PBS | 4FS |
| 116 | 5N | 4RS | 4RS | 3GFS | 2BS | 1 |
| 117 | 3RS | 2RS | 4RS | 4BS | 2BS | 3BS |
| 119 | 2CBS | 2CBS | 2S | 4CBS | 4CBS | 4CBS |
| 122 | 5N | 5N | 5N | 4CBS | 2BS | 5D |
| 132 | 1 | 1 | 1 | 1 | 1 | 1 |
| 134 | 1 | 1 | 1 | 1 | 1 | 1 |
| 147 | 2RS | 1 | 3RS | 1 | 1 | 1 |
| 148 | 1 | 1 | 1 | 1 | 1 | 1 |
| 149 | 4RS | 4RS | 5N | 2FS | 1 | 2FS |
| 151 | 2RS | 3RS | 3RS | 2FS | 1 | 3CS |
| 153 | 1 | 2RS | 2RS | 3CS | 1 | 3CS |
| 155 | 5N | 5N | 5N | 2FS | 1 | 2FS |
| 157 | 5N | 5N | 5N | 5D | 4BS | 5D |
| 161 | 5N | 5N | 5N | 1 | 1 | 1 |
| 169 | 5N | 5N | 5N | 3CBS | 1 | 2CS |
| 170 | 4RS | 4RS | 5N | 1 | 1 | 1 |

A similar greenhouse study utilizing seven seed species was carried out to further evaluate preemergence and postemergence herbicidal activity of the benzamides of this invention. The compounds to be evaluated were formulated according to the procedure outlined above, except that about 4 g/100 ml of the compound were dissolved in the surfactant-containing solvent, and about 1 part of the organic solution was diluted with 12 parts of water before application to seeded containers. The compounds were applied at the effective rate of 8 lbs/acre. Typical results of such evaluation are presented in Table II below.

TABLE II

| Compound of Example Number | Preemergence | | | | | | | Postemergence | | | | | | |
|---|---|---|---|---|---|---|---|---|---|---|---|---|---|---|
| | Corn | Large Crab-grass | Pig-weed | Fox-tail | Velvet Leaf | Morn-ing-glory | Zinnia | Corn | Large Crab-grass | Pig-weed | Fox-tail | Velvet Leaf | Morn-ing-glory | Zinnia |
| 1 | 5 | 5 | 5 | 5 | 5 | 4 | 5 | 1 | 3 | 3 | 2 | 1 | 2 | 3 |
| 2 | 1 | 1 | 4 | 1 | 1 | 2 | 3 | 1 | 1 | 1 | 1 | 1 | 1 | 2 |
| 4 | 1 | 2 | 5 | 2 | 2 | 3 | 5 | 1 | 1 | 1 | 1 | 1 | 1 | 1 |
| 6 | 1 | 1 | 5 | 1 | 1 | 1 | 2 | 2 | 1 | 1 | 1 | 1 | 1 | 2 |
| 8 | 1 | 1 | 3 | 1 | 1 | 2 | 1 | 1 | 1 | 1 | 1 | 1 | 1 | 1 |
| 9 | 3 | 4 | 5 | 4 | 1 | 1 | 4 | 1 | 1 | 1 | 1 | 1 | 1 | 1 |
| 10 | 2 | 5 | 5 | 3 | 3 | 2 | 4 | 1 | 1 | 3 | 1 | 1 | 2 | 3 |
| 11 | 1 | 3 | 5 | 2 | 1 | 2 | 1 | 1 | 1 | 2 | 1 | 1 | 1 | 3 |
| 12 | 2 | 4 | 5 | 3 | 3 | 3 | 2 | 2 | 1 | 3 | 1 | 2 | 2 | 3 |
| 13 | 3 | 4 | 5 | 4 | 1 | 1 | 1 | 1 | 1 | 3 | 1 | 1 | 2 | 2 |
| 14 | 4 | 5 | 5 | 5 | 4 | 5 | 5 | 2 | 1 | 4 | 1 | 2 | 3 | 3 |
| 16 | 3 | 4 | 5 | 4 | 3 | 3 | 3 | 2 | 1 | 1 | 1 | 1 | 2 | 3 |
| 17 | 2 | 4 | 5 | 4 | 3 | 2 | 2 | 2 | 1 | 3 | 2 | 2 | 2 | 3 |
| 19 | 5 | 5 | 5 | 5 | 5 | 5 | 5 | 3 | 3 | 4 | 2 | 3 | 3 | 3 |
| 22 | 3 | 4 | 5 | 2 | 2 | 4 | 4 | 1 | 1 | 3 | 1 | 1 | 2 | 3 |
| 23 | 2 | 5 | 5 | 4 | 3 | 3 | 3 | 1 | 1 | 3 | 1 | 1 | 1 | 2 |
| 24 | 3 | 4 | 5 | 3 | 3 | 3 | 5 | 1 | 1 | 2 | 1 | 2 | 1 | 2 |
| 26 | 1 | 3 | 5 | 2 | 2 | 1 | 3 | 1 | 1 | 2 | 1 | 1 | 1 | 2 |
| 30 | 2 | 1 | 1 | 2 | 1 | 1 | 2 | 1 | 1 | 1 | 1 | 1 | 1 | 1 |
| 33 | 1 | 1 | 2 | 1 | 3 | 1 | 5 | 1 | 1 | 1 | 1 | 1 | 1 | 1 |
| 37 | 2 | 3 | 2 | 2 | 1 | 1 | 1 | 2 | 1 | 1 | 1 | 2 | 2 | 2 |
| 41 | 1 | 1 | 4 | 1 | 1 | 1 | 1 | 1 | 1 | 3 | 1 | 1 | 1 | 3 |
| 47 | 2 | 1 | 1 | 3 | 2 | 1 | 3 | 1 | 1 | 1 | 1 | 1 | 1 | 1 |
| 48 | 1 | 2 | 2 | 2 | 1 | 1 | 1 | 1 | 1 | 1 | 1 | 1 | 1 | 1 |
| 49 | 1 | 3 | 2 | 2 | 1 | 1 | 1 | — | — | — | — | — | — | — |
| 50 | 1 | 1 | 2 | 1 | 1 | 1 | 1 | 1 | 1 | 1 | 1 | 1 | 1 | 1 |
| 51 | 1 | 1 | 1 | 1 | 1 | 1 | 1 | 1 | 1 | 1 | 1 | 1 | 2 | 2 |
| 52 | 1 | 1 | 1 | 1 | 1 | 2 | 1 | 2 | 1 | 1 | 1 | 1 | 1 | 1 |
| 53 | 2 | 1 | 1 | 1 | 1 | 1 | 1 | 2 | 1 | 1 | 1 | 1 | 1 | 1 |
| 54 | 2 | 1 | 1 | 1 | 1 | 1 | 1 | 2 | 1 | 1 | 1 | 2 | 2 | 2 |
| 55 | 2 | 5 | 5 | 5 | 5 | 3 | 3 | 1 | 2 | 4 | 1 | 3 | 2 | 3 |
| 56 | 2 | 5 | 5 | 5 | 4 | 5 | 5 | 1 | 3 | 3 | 2 | 1 | 2 | 1 |
| 57 | 1 | 1 | 2 | 2 | 1 | 1 | 1 | 1 | 1 | 1 | 1 | 1 | 1 | 1 |
| 58 | 1 | 1 | 3 | 1 | 1 | 1 | 3 | 1 | 1 | 1 | 1 | 1 | 1 | 1 |
| 59 | 1 | 1 | 3 | 1 | 1 | 1 | 1 | 1 | 1 | 1 | 1 | 1 | 1 | 1 |
| 61 | 4 | 5 | 5 | 5 | 5 | 5 | 5 | 2 | 2 | 4 | 1 | 1 | 2 | 3 |
| 62 | 1 | 3 | 5 | 2 | 2 | 1 | 2 | 2 | 3 | 4 | 1 | 2 | 1 | 1 |
| 63 | 1 | 2 | 4 | 1 | 1 | 2 | 3 | 1 | 1 | 2 | 1 | 1 | 2 | 2 |
| 64 | 1 | 2 | 5 | 1 | 1 | 2 | 2 | 1 | 1 | 2 | 1 | 1 | 1 | 2 |
| 66 | 3 | 4 | 5 | 4 | 3 | 2 | 3 | 2 | 1 | 3 | 1 | 1 | 2 | 2 |
| 67 | 1 | 3 | 5 | 2 | 1 | 2 | 2 | 1 | 1 | 1 | 1 | 1 | 1 | 1 |
| 68 | 1 | 2 | 5 | 2 | 2 | 2 | 5 | 1 | 1 | 3 | 1 | 1 | 1 | 2 |
| 69 | 1 | 1 | 2 | 1 | 1 | 2 | 2 | 1 | 1 | 3 | 1 | 1 | 2 | 2 |
| 70 | 1 | 1 | 1 | 1 | 1 | 1 | 1 | 1 | 2 | 2 | 1 | 1 | 1 | 1 |
| 75 | 1 | 1 | 4 | 1 | 1 | 1 | 3 | 1 | 1 | 1 | 1 | 1 | 2 | 1 |
| 77 | 1 | 1 | 2 | 1 | 1 | 1 | 1 | 1 | 1 | 1 | 1 | 1 | 1 | 1 |
| 78 | 1 | 1 | 3 | 1 | 1 | 1 | 1 | 1 | 1 | 1 | 1 | 1 | 1 | 1 |
| 79 | 1 | 1 | 1 | 1 | 1 | 2 | 1 | 1 | 1 | 1 | 1 | 2 | 2 | 2 |
| 80 | 1 | 4 | 5 | 3 | 1 | 2 | 5 | 2 | 1 | 1 | 1 | 1 | 2 | 2 |
| 81 | 1 | 1 | 3 | 1 | 1 | 1 | 1 | 1 | 1 | 1 | 1 | 1 | 1 | 1 |
| 82 | 1 | 4 | 5 | 2 | 2 | 3 | 4 | 1 | 1 | 3 | 1 | 1 | 1 | 1 |
| 83 | 2 | 4 | 5 | 3 | 2 | 3 | 4 | 1 | 1 | 1 | 1 | 1 | 1 | 1 |
| 84 | 1 | 1 | 4 | 1 | 1 | 1 | 1 | 1 | 1 | 1 | 1 | 1 | 1 | 1 |
| 85 | 1 | 1 | 1 | 1 | 1 | 1 | 1 | 1 | 1 | 1 | 1 | 1 | 1 | 1 |
| 86 | 1 | 1 | 4 | 1 | 1 | 1 | 1 | 1 | 1 | 1 | 1 | 1 | 1 | 1 |
| 87 | 1 | 3 | 3 | 2 | 3 | 2 | 3 | 1 | 1 | 1 | 1 | 1 | 1 | 1 |
| 88 | 3 | 5 | 5 | 4 | 3 | 3 | 3 | 1 | 1 | 3 | 1 | 1 | 1 | 2 |
| 92 | 1 | 1 | 3 | 1 | 1 | 1 | 1 | 1 | 1 | 1 | 1 | 1 | 2 | 1 |
| 94 | 1 | 1 | 1 | 1 | 1 | 1 | 1 | 1 | 1 | 1 | 1 | 1 | 1 | 1 |
| 95 | 3 | 4 | 5 | 4 | 3 | 3 | 2 | 1 | 2 | 4 | 2 | 3 | 3 | 3 |
| 97 | 1 | 3 | 5 | 2 | 1 | 1 | 3 | 1 | 1 | 1 | 1 | 1 | 1 | 1 |
| 99 | 1 | 4 | 5 | 1 | 1 | 1 | 1 | 1 | 1 | 3 | 1 | 1 | 1 | 2 |
| 100 | 1 | 1 | 1 | 1 | 1 | 1 | 1 | 1 | 1 | 1 | 1 | 2 | 2 | 1 |
| 101 | 1 | 4 | 4 | 1 | 1 | 3 | 2 | 2 | 1 | 2 | 1 | 1 | 1 | 2 |
| 102 | 1 | 2 | 3 | 1 | 1 | 1 | 2 | 1 | 1 | 1 | 1 | 1 | 1 | 1 |
| 103 | 1 | 4 | 1 | 1 | 1 | 1 | 1 | 2 | 1 | 3 | 1 | 1 | 3 | 5 |
| 104 | 1 | 4 | 3 | 3 | 2 | 2 | 1 | 1 | 1 | 1 | 1 | 1 | 2 | 1 |
| 106 | 1 | 1 | 1 | 1 | 1 | 1 | 1 | 1 | 1 | 1 | 1 | 1 | 1 | 2 |
| 110 | 1 | 1 | 1 | 1 | 1 | 1 | 1 | 1 | 1 | 1 | 1 | 1 | 1 | 1 |
| 113 | 2 | 1 | 2 | 1 | 1 | 1 | 1 | 2 | 1 | 1 | 1 | 1 | 1 | 1 |
| 114 | 1 | 4 | 5 | 3 | 2 | 3 | 5 | 1 | 1 | 1 | 1 | 1 | 1 | 1 |

TABLE II-continued

| Compound of Example Number | Preemergence | | | | | | | Postemergence | | | | | |
|---|---|---|---|---|---|---|---|---|---|---|---|---|---|
| | Corn | Large Crab-grass | Pig-weed | Fox-tail | Velvet Leaf | Morn-ing-glory | Zinnia | Corn | Large Crab-grass | Pig-weed | Fox-tail | Velvet Leaf | Morn-ing-glory | Zinnia |
| 115 | 2 | 4 | 4 | 3 | 2 | 4 | 3 | 1 | 1 | 1 | 2 | 1 | 1 | 2 |
| 116 | 1 | 4 | 4 | 2 | 2 | 2 | 1 | 1 | 1 | 1 | 1 | 1 | 1 | 2 |
| 118 | 1 | 2 | 5 | 1 | 2 | 2 | 2 | 1 | 1 | 1 | 1 | 1 | 1 | 1 |
| 119 | 1 | 2 | 2 | 4 | 3 | 1 | 3 | 1 | 2 | 3 | 3 | 2 | 1 | 1 |
| 126 | 1 | 2 | 2 | 1 | 1 | 1 | 1 | 1 | 1 | 1 | 1 | 1 | 1 | 1 |
| 128 | 1 | 5 | 4 | 1 | 3 | 2 | 2 | 1 | 1 | 3 | 1 | 1 | 1 | 2 |
| 129 | 1 | 1 | 2 | 1 | 1 | 1 | 1 | 1 | 1 | 1 | 1 | 1 | 1 | 1 |
| 131 | 1 | 1 | 1 | 1 | 1 | 1 | 1 | 1 | 1 | 1 | 1 | 1 | 1 | 1 |
| 137 | 1 | 1 | 1 | 1 | 1 | 1 | 1 | 1 | 3 | 1 | 1 | 1 | 1 | 2 |
| 138 | 1 | 2 | 2 | 1 | 1 | 1 | 1 | 1 | 1 | 1 | 1 | 1 | 1 | 1 |
| 139 | 1 | 1 | 2 | 1 | 1 | 1 | 1 | 1 | 1 | 1 | 1 | 1 | 1 | 1 |
| 140 | 1 | 1 | 4 | 2 | 1 | 1 | 2 | 1 | 1 | 1 | 1 | 1 | 1 | 1 |
| 141 | 3 | 5 | 5 | 5 | 5 | 5 | 5 | 2 | 2 | 2 | 2 | 2 | 3 | 2 |
| 142 | 2 | 3 | 3 | 4 | 5 | 5 | 4 | 1 | 1 | 1 | 1 | 1 | 1 | 1 |
| 143 | 1 | 1 | 1 | 1 | 1 | 1 | 1 | 1 | 1 | 1 | 1 | 1 | 1 | 1 |
| 144 | 2 | 1 | 4 | 1 | 1 | 1 | 1 | 1 | 1 | 1 | 1 | 1 | 2 | 1 |
| 145 | 1 | 4 | 5 | 3 | 1 | 1 | 1 | 1 | 1 | 1 | 1 | 1 | 1 | 1 |
| 146 | 1 | 1 | 2 | 1 | 1 | 1 | 2 | 1 | 1 | 1 | 1 | 1 | 1 | 1 |
| 150 | 1 | 1 | 1 | 1 | 1 | 1 | 1 | 1 | 2 | 1 | 1 | 1 | 2 | 2 |
| 152 | 2 | 4 | 5 | 4 | 2 | 4 | 2 | 1 | 2 | 4 | 2 | 3 | 2 | 3 |
| 154 | 1 | 2 | 2 | 1 | 1 | 2 | 2 | 1 | 1 | 2 | 1 | 1 | 2 | 2 |
| 156 | 1 | 4 | 5 | 1 | 1 | 3 | 2 | 1 | 1 | 3 | 1 | 1 | 1 | 1 |
| 158 | 3 | 5 | 5 | 3 | 3 | 4 | 3 | 2 | 2 | 3 | 2 | 2 | 3 | 4 |
| 162 | 1 | 2 | 2 | 1 | 1 | 1 | 1 | 1 | 1 | 1 | 1 | 1 | 1 | 1 |
| 163 | 1 | 1 | 1 | 1 | 1 | 1 | 1 | 1 | 1 | 2 | 1 | 1 | 1 | 1 |
| 166 | 4 | 3 | 4 | 5 | 5 | 3 | 1 | 2 | 1 | 1 | 1 | 1 | 1 | 1 |
| 167 | 1 | 3 | 5 | 3 | 1 | 2 | 2 | 1 | 1 | 1 | 1 | 1 | 1 | 1 |
| 168 | 5 | 5 | 4 | 5 | 3 | 4 | 2 | 4 | 3 | 2 | 1 | 1 | 2 | 1 |
| 170 | 3 | 4 | 5 | 3 | 2 | 2 | 2 | 1 | 1 | 1 | 1 | 1 | 1 | 1 |
| 173 | 1 | 2 | 4 | 1 | 2 | 1 | 1 | 1 | 1 | 1 | 1 | 1 | 1 | 1 |
| 176 | 1 | 4 | 5 | 2 | 2 | 1 | 1 | 1 | 1 | 1 | 1 | 1 | 1 | 1 |

The herbicidal activity of a number of the more active benzamides of the invention was evaluated at various application rates in a multiple-species greenhouse test. Several additional weed and crop species were utilized to determine the herbicidal selectivity of the compounds. The compounds were formulated as described above, and applied preemergence to seeded flats. The results for several compounds of the invention are presented below in Table III.

TABLE III

Preemergence

| Compound of Example No. | Rate of Application Lbs/Acre | Corn | Cotton | Soybean | Wheat | Alfalfa | Sugar Beet | Rice | Cucumber | Tomato | Barnyard Grass | Lambsquarter | Large Crabgrass | Mustard | Pigweed | Foxtail | Wildoat | Velvetleaf | Jimson Weed | Morning-glory | Zinnia |
|---|---|---|---|---|---|---|---|---|---|---|---|---|---|---|---|---|---|---|---|---|---|
| 1 | 1 | 4 | 1 | 4 | 1 | 2 | 5 | 3 | 5 | 5 | 5 | 5 | 5 | 5 | 5 | 5 | 3 | 4 | 5 | 3 | 5 |
|  | 0.5 | 2 | 1 | 3 | 1 | 5 | 5 | 3 | 2 | 5 | 4 | 5 | 5 | 5 | 5 | 5 | 2 | 3 | 5 | 2 | 5 |
|  | 0.25 | 1 | 1 | 2 | 1 | 5 | 5 | 2 | 4 | 4 | 4 | 5 | 5 | 3 | 5 | 4 | 1 | 3 | 5 | 2 | 3 |
| 3 | 1 | 1 | 1 | 2 | 1 | 1 | 5 | 1 | 3 | 4 | 4 | 5 | 4 | 3 | 4 | 1 | 1 | 3 | 3 | 1 | 3 |
|  | 0.5 | 1 | 1 | 2 | 1 | 1 | 5 | 1 | 2 | 3 | 3 | 5 | 3 | 2 | 4 | 1 | 1 | 2 | 1 | 1 | 2 |
|  | 0.25 | 1 | 1 | 1 | 1 | 1 | 4 | 1 | 1 | 1 | 1 | 4 | 1 | 2 | 4 | 1 | 1 | 1 | 1 | 1 | 2 |
| 4 | 1 | 1 | 1 | 1 | 1 | 4 | 5 | 1 | 1 | 2 | 1 | 5 | 1 | 3 | 5 | 1 | 1 | 1 | 4 | 1 | 2 |
|  | 0.5 | 1 | 1 | 1 | 1 | 4 | 5 | 1 | 1 | 3 | 2 | 5 | 1 | 2 | 4 | 1 | 1 | 1 | 3 | 1 | 5 |
|  | 0.25 | 1 | 1 | 1 | 1 | 1 | 3 | 1 | 1 | 1 | 1 | 3 | 1 | 1 | 3 | 1 | 1 | 1 | 2 | 1 | 4 |
| 5 | 4 | 1 | 2 | 1 | 1 | 4 | 5 | 1 | 2 | 1 | 2 | 5 | 2 | 5 | 3 | 1 | 1 | 2 | 2 | 2 | 1 |
| 6 | 4 | 2 | 2 | 4 | 3 | 4 | 5 | 1 | 4 | 4 | 1 | 5 | 1 | 3 | 5 | 4 | 1 | 1 | 5 | 4 | 5 |
|  | 2 | 2 | 2 | 2 | 1 | 2 | 5 | 1 | 2 | 1 | 1 | 5 | 1 | 3 | 5 | 1 | 1 | 2 | 4 | 2 | 4 |
|  | 1 | 1 | 1 | 2 | 1 | 1 | 3 | 1 | 2 | 1 | 1 | 4 | 1 | 3 | 4 | 1 | 1 | 2 | 2 | 1 | 3 |
|  | 0.5 | 1 | 1 | 2 | 1 | 3 | 4 | 1 | 2 | 1 | 1 | 5 | 1 | 3 | 3 | 1 | 1 | 2 | 5 | 1 | 2 |
|  | 0.25 | 1 | 1 | 1 | 1 | 1 | 3 | 1 | 1 | 1 | 1 | 3 | 1 | 2 | 2 | 1 | 1 | 2 | 4 | 1 | 1 |
| 9 | 4 | 2 | 2 | 3 | 1 | 2 | 5 | 2 | 2 | 2 | 2 | 5 | 3 | 5 | 5 | 2 | 1 | 2 | 5 | 2 | 5 |
|  | 1 | 1 | 1 | 2 | 1 | 1 | 3 | 2 | 2 | 1 | 1 | 5 | 2 | 3 | 3 | 1 | 1 | 2 | 3 | 1 | 3 |
|  | 0.5 | 1 | 1 | 1 | 1 | 1 | 2 | 1 | 1 | 1 | 1 | 3 | 1 | 2 | 2 | 1 | 1 | 1 | 2 | 1 | 4 |
|  | 0.125 | 1 | 1 | 1 | 1 | 1 | 1 | 1 | 1 | 1 | 1 | 2 | 1 | 1 | 1 | 1 | 1 | 1 | 1 | 1 | 2 |
| 11 | 4 | 2 | 2 | 1 | 1 | 4 | 4 | 1 | 3 | 2 | 2 | 4 | 3 | 4 | 5 | 2 | 1 | 3 | 2 | 1 | 2 |
|  | 2 | 1 | 1 | 1 | 1 | 3 | 3 | 1 | 1 | 1 | 1 | 5 | 2 | 3 | 3 | 1 | 1 | 2 | 2 | 1 | 1 |
|  | 1 | 1 | 1 | 1 | 1 | 1 | 2 | 1 | 1 | 1 | 1 | 3 | 1 | 2 | 2 | 1 | 1 | 1 | 1 | 1 | 1 |
| 13 | 4 | 2 | 2 | 2 | 1 | 1 | 5 | 2 | 3 | 2 | 3 | 5 | 3 | 5 | 5 | 2 | 1 | 3 | 5 | 3 | 4 |
|  | 2 | 1 | 1 | 2 | 1 | 1 | 5 | 1 | 2 | 2 | 2 | 5 | 3 | 3 | 5 | 2 | 1 | 2 | 3 | 2 | 4 |
|  | 1 | 1 | 1 | 1 | 1 | 1 | 3 | 1 | 2 | 2 | 2 | 5 | 2 | 2 | 4 | 1 | 1 | 2 | 2 | 1 | 5 |
| 14 | 4 | 2 | 2 | 2 | 2 | 5 | 5 | 1 | 5 | 5 | 5 | 5 | 5 | 5 | 5 | 5 | 2 | 2 | 5 | 3 | 4 |
|  | 1 | 1 | 1 | 1 | 1 | 4 | 3 | 1 | 2 | 2 | 3 | 5 | 3 | 5 | 5 | 4 | 1 | 2 | 4 | 2 | 4 |
| 15 | 0.5 | 1 | 1 | 1 | 1 | 3 | 3 | 2 | 2 | 1 | 1 | 5 | 2 | 3 | 4 | 2 | 1 | 2 | 3 | 1 | 2 |
|  | 0.25 | 1 | 1 | — | 1 | 3 | 2 | 1 | 1 | 1 | 1 | 4 | 1 | 2 | 2 | 1 | 1 | 2 | 2 | 1 | 2 |
| 16 | 0.5 | 2 | 2 | 2 | 2 | 1 | 5 | 1 | 2 | 4 | 4 | 5 | 4 | 5 | 4 | 4 | 1 | 2 | 4 | 1 | 4 |
|  | 0.25 | 2 | 1 | 1 | 1 | 1 | 3 | 1 | 2 | 2 | 2 | 5 | 2 | 3 | 5 | 2 | 1 | 2 | 2 | 1 | 4 |
| 17 | 0.5 | 1 | 1 | 1 | 1 | 1 | 5 | 1 | 3 | 2 | 1 | 5 | 4 | 5 | 5 | 4 | 1 | 2 | 5 | 1 | 5 |
|  | 0.25 | 1 | 1 | 1 | 1 | 1 | 1 | 1 | 2 | 1 | 1 | 4 | 2 | 3 | 5 | 2 | 1 | 3 | 2 | 1 | 2 |
| 21 | 1 | 1 | 2 | 2 | 1 | 2 | 5 | 1 | 2 | 2 | 3 | 4 | 3 | 3 | 4 | 2 | 2 | 2 | 2 | 1 | 4 |
|  | 0.5 | 1 | 1 | 1 | 1 | 1 | 2 | 1 | 1 | 1 | 1 | 3 | 2 | 2 | 2 | 1 | 1 | 2 | 2 | 1 | 1 |
| 23 | 1 | 2 | 2 | 3 | 1 | 1 | 5 | 3 | 3 | 5 | 5 | 5 | 5 | 4 | 4 | 4 | 2 | 2 | 2 | 3 | 3 |
|  | 0.5 | 1 | 1 | 3 | 1 | 1 | 5 | 2 | 2 | 3 | 4 | 5 | 3 | 3 | 3 | 3 | 2 | 3 | — | — | 2 |
|  | 0.25 | 1 | 1 | 1 | 1 | 1 | 3 | 1 | 1 | 2 | 3 | 4 | 2 | 2 | 2 | 3 | 1 | 2 | — | 1 | 2 |
|  | 0.125 | 1 | 1 | — | 1 | 1 | 1 | 1 | 1 | 1 | 1 | 4 | 2 | 2 | — | 1 | 1 | — | — | 1 | 4 |
| 24 | 1 | 1 | 1 | — | 1 | 1 | 4 | 1 | 3 | 2 | 1 | 5 | 2 | 4 | 4 | — | 1 | — | 2 | 3 | 4 |
|  | 0.5 | 1 | 1 | 1 | 1 | 1 | 3 | 1 | 2 | 2 | 1 | 5 | 2 | 4 | 5 | — | 1 | — | — | 1 | 4 |
|  | 0.25 | 1 | 2 | 1 | 1 | 1 | 5 | 1 | 1 | 1 | 1 | 5 | 2 | 3 | 5 | 1 | 1 | 2 | 2 | 1 | 4 |
| 26 | 4 | 1 | 2 | 2 | 1 | 1 | 5 | 1 | 1 | 1 | 1 | 5 | 2 | 4 | 3 | 2 | 1 | 1 | — | 1 | 2 |

TABLE III-continued

Preemergence

| Compound of Example No. | Rate of Application Lbs/Acre | Corn | Cotton | Soybean | Wheat | Alfalfa | Sugar Beat | Rice | Cucumber | Tomato | Barnyard Grass | Lambsquarter | Large Crabgrass | Mustard | Pigweed | Foxtail | Wildoat | Velvetleaf | Jimson Weed | Morningglory | Zinnia |
|---|---|---|---|---|---|---|---|---|---|---|---|---|---|---|---|---|---|---|---|---|---|
| 27 | 2 | 1 | 1 | 1 | 1 | 1 | 4 | 1 | 1 | 1 | 1 | 2 | 2 | 3 | 2 | 1 | 1 | 1 | 2 | 1 | 2 |
|  | 1 | 1 | 2 | 3 | 1 | 3 | 2 | 2 | 4 | 4 | 1 | 5 | 2 | 5 | 5 | 2 | 1 | 2 | 1 | 1 | 2 |
|  | 4 | 1 | 1 | 4 | 1 | 3 | 5 | 1 | 2 | 4 | 2 | 5 | 1 | 5 | 5 | 1 | 1 | 2 | 4 | 2 | 5 |
|  | 2 | 1 | 1 | 1 | 1 | 5 | 5 | 1 | 2 | 3 | 1 | 5 | 4 | 3 | 5 | 1 | 1 | 2 | 5 | 3 | 3 |
|  | 1 | 1 | 1 | 2 | 1 | 1 | 4 | 2 | 2 | 1 | 4 | 5 | 3 | 3 | 4 | 3 | 2 | 2 | 2 | 2 | 4 |
| 29 | 0.5 | 2 | 1 | 1 | 1 | 1 | 5 | 1 | 3 | 2 | 3 | 4 | 2 | 2 | 3 | 2 | 2 | 3 | 3 | 1 | 2 |
|  | 1 | 2 | 1 | 1 | 1 | 1 | 2 | 1 | 2 | 1 | 3 | 4 | 3 | 2 | 3 | 2 | 1 | 3 | 2 | 1 | 2 |
|  | 0.5 | 2 | 1 | 2 | 1 | 1 | 2 | 1 | 2 | 1 | 2 | 3 | 2 | 2 | 3 | 1 | 1 | 1 | 3 | 1 | 1 |
|  | 0.25 | 1 | 1 | 1 | 1 | 1 | 1 | 1 | 1 | 1 | 1 | 2 | 1 | 1 | 2 | 1 | 1 | 1 | 1 | 1 | 1 |
| 31 | 0.5 | 1 | 1 | 1 | 1 | 1 | 4 | 1 | 1 | 1 | 1 | 4 | 1 | 2 | 3 | 1 | 1 | 1 | 1 | 1 | 1 |
|  | 0.25 | 1 | 1 | 1 | 1 | 1 | 3 | 1 | 1 | 1 | 1 | 4 | 1 | 1 | 2 | 1 | 1 | 1 | 1 | 1 | 1 |
| 33 | 1 | 2 | 1 | 3 | 1 | 2 | 5 | 1 | 2 | 1 | 2 | 5 | 4 | 2 | 4 | 4 | 1 | 3 | 3 | 2 | 2 |
|  | 0.5 | 1 | 1 | 1 | 1 | 1 | 3 | 1 | 1 | 1 | 2 | 5 | 4 | 2 | 3 | 1 | 1 | 2 | 1 | 3 | 3 |
| 34 | 1 | 1 | 1 | 1 | 1 | 1 | 3 | 1 | 1 | 1 | 1 | 2 | 1 | 1 | 4 | 1 | 1 | 1 | 1 | 1 | 1 |
|  | 0.5 | 1 | 1 | 1 | 1 | 1 | 2 | 1 | 1 | 1 | 1 | 1 | 1 | 1 | 2 | 1 | 1 | 1 | 1 | 1 | 1 |
| 35 | 0.5 | 1 | 1 | 1 | 1 | 1 | 1 | 1 | 1 | 1 | 1 | 1 | 1 | 4 | 3 | 1 | 1 | 1 | 1 | 1 | 2 |
| 36 | 1 | 1 | 1 | 1 | 1 | 1 | 3 | 2 | 2 | 2 | 1 | 5 | 2 | 2 | 3 | 2 | 1 | 1 | 1 | 1 | 3 |
|  | 0.5 | 1 | 1 | 1 | 1 | 1 | 4 | 1 | 2 | 2 | 1 | 5 | 3 | 5 | 4 | 3 | 1 | 1 | 5 | 3 | 5 |
| 42 | 0.5 | 1 | 1 | 1 | 1 | 1 | 3 | 1 | 2 | 2 | 1 | 5 | 3 | 4 | 5 | 2 | 1 | 2 | 4 | 2 | 3 |
| 43 | 2 | 1 | 1 | 4 | 1 | 5 | 5 | 4 | 5 | 5 | 5 | 5 | 5 | 5 | 5 | 5 | 4 | 5 | 5 | 3 | 5 |
|  | 4 | 4 | 2 | 4 | 3 | 4 | 5 | 3 | 2 | 2 | 3 | 5 | 4 | 4 | 5 | 4 | 1 | 2 | 4 | 2 | 3 |
| 61 | 0.5 | 2 | 1 | 4 | 2 | 4 | 2 | 1 | 2 | 1 | 1 | 5 | 3 | 4 | 3 | 1 | 1 | 2 | 3 | 1 | 2 |
|  | 0.125 | 2 | 1 | 2 | 1 | 1 | 1 | 1 | 1 | 1 | 1 | 4 | 2 | 1 | 2 | 1 | 1 | 1 | 2 | 1 | 1 |
| 62 | 4 | 1 | 1 | 1 | 1 | 1 | 1 | 1 | 1 | 1 | 1 | 2 | 1 | 1 | 2 | 1 | 1 | 1 | 1 | 1 | 1 |
|  | 2 | 1 | 1 | 1 | 1 | 1 | 1 | 1 | 1 | 1 | 1 | 1 | 1 | 1 | 1 | 1 | 1 | 1 | 1 | 1 | 1 |
| 63 | 1 | 1 | 1 | 1 | 1 | 1 | 3 | 1 | 1 | 1 | 2 | 4 | 2 | 3 | 4 | 2 | 1 | 2 | 2 | 1 | 4 |
|  | 0.5 | 1 | 1 | 1 | 1 | 1 | 1 | 1 | 1 | 1 | 1 | 3 | 1 | 2 | 4 | 1 | 1 | 1 | 1 | 1 | 2 |
|  | 0.25 | 1 | 1 | 1 | 1 | 1 | 1 | 1 | 1 | 1 | 1 | 1 | 1 | 1 | 1 | 1 | 1 | 1 | 1 | 1 | 1 |
| 64 | 4 | 1 | 2 | 1 | 1 | 1 | 4 | 1 | 2 | 2 | 2 | 5 | 3 | 3 | 4 | 2 | 2 | 2 | 3 | 3 | 4 |
|  | 2 | 1 | 2 | 4 | 2 | 5 | 3 | 4 | 3 | 2 | 1 | 3 | 2 | 2 | 3 | 1 | 2 | 4 | 3 | 1 | 2 |
|  | 1 | 1 | 1 | 2 | 2 | 3 | 5 | 3 | 2 | 2 | 1 | 5 | 5 | 5 | 5 | 5 | 1 | 2 | 5 | 3 | 3 |
| 66 | 4 | 4 | 1 | 4 | 1 | 1 | 5 | 4 | 2 | 5 | 5 | 5 | 4 | 3 | 4 | 4 | 1 | 4 | 5 | 1 | 1 |
|  | 1 | 2 | 1 | 1 | 1 | 1 | 5 | 3 | 2 | 2 | 4 | 5 | 4 | 4 | 4 | 4 | 2 | 3 | 5 | 2 | 3 |
|  | 0.5 | 2 | 1 | 1 | 1 | 3 | 2 | 4 | 2 | 2 | 4 | 4 | 5 | 3 | 5 | 1 | 2 | 2 | 3 | 1 | 2 |
|  | 0.125 | 1 | 1 | 1 | 1 | 1 | 1 | 2 | 1 | 1 | 2 | 2 | 2 | 2 | 4 | 1 | 1 | 1 | 2 | 1 | 1 |
| 68 | 4 | 1 | 1 | 1 | 1 | 1 | 4 | 1 | 1 | 1 | 2 | 5 | 1 | 3 | 4 | 1 | 1 | 1 | 2 | 1 | 3 |
|  | 2 | 1 | 1 | 1 | 1 | 1 | 1 | 1 | 1 | 3 | 1 | 5 | 2 | 3 | 4 | 1 | 1 | 1 | 3 | 1 | 2 |
|  | 1 | 1 | 1 | 1 | 1 | 1 | 3 | 1 | 1 | 2 | 3 | 5 | 2 | 4 | 4 | 2 | 1 | 2 | 2 | 1 | 2 |
|  | 0.5 | 1 | 1 | 1 | 1 | 1 | 3 | 1 | 1 | 2 | 2 | 5 | 1 | 2 | 4 | 1 | 1 | 1 | 2 | 1 | 4 |
| 73 | 4 | 1 | 2 | 2 | 1 | 3 | 5 | 2 | 3 | 2 | 3 | 5 | 4 | 3 | 5 | 2 | 2 | 3 | 5 | 2 | 1 |
|  | 1 | 1 | 1 | 1 | 1 | 1 | 3 | 1 | 1 | 2 | 2 | 5 | 1 | 3 | 5 | 1 | 1 | 1 | 3 | 1 | 1 |
| 74 | 0.5 | 1 | 1 | 2 | 1 | 3 | 5 | 3 | 2 | 3 | 3 | 5 | 3 | 3 | 5 | 2 | 3 | 3 | 4 | 2 | 1 |
|  | 1 | 1 | 1 | 2 | 1 | 2 | 5 | 4 | 1 | 3 | 3 | 5 | 4 | 3 | 5 | 2 | 1 | 1 | 5 | 1 | 2 |

TABLE III-continued

| Compound of Example No. | Rate of Application Lbs/Acre | Preemergence | | | | | | | | | | | | | | | | | |
|---|---|---|---|---|---|---|---|---|---|---|---|---|---|---|---|---|---|---|---|
| | | Corn | Cotton | Soybean | Wheat | Alfalfa | Sugar Beet | Rice | Cucumber | Tomato | Barnyard Grass | Lambs-quarter | Large Crabgrass | Mustard | Pigweed | Foxtail | Wildoat | Velvetleaf | Jimson Weed | Morning-glory | Zinnia |
| 76 | 0.25 | 2 | 1 | — | — | — | 5 | — | — | 5 | 2 | 5 | 5 | 2 | 5 | — | — | — | 4 | — | 1 |
| | 1 | 1 | 1 | 2 | 2 | 4 | 4 | 1 | 1 | 5 | 5 | 5 | 5 | 5 | 5 | 4 | 2 | 2 | 4 | 2 | 3 |
| 83 | 0.5 | 1 | 1 | 2 | 1 | 1 | 2 | 2 | 2 | 2 | 1 | 4 | 3 | 3 | 4 | 1 | 1 | 2 | 4 | 1 | 1 |
| | 0.25 | 1 | 1 | 1 | 1 | 1 | 2 | 1 | 3 | 3 | 1 | 2 | 1 | 3 | 2 | 1 | 1 | 2 | 3 | 1 | 3 |
| 89 | 0.5 | 1 | — | 1 | 1 | 4 | 4 | 1 | 1 | 2 | 1 | 5 | 2 | 2 | 4 | 1 | 1 | 1 | 5 | 1 | 3 |
| | 0.25 | 1 | 1 | 1 | 1 | 1 | 2 | 1 | 1 | 1 | 1 | 4 | 1 | 2 | 3 | 1 | 1 | 1 | 4 | 1 | 2 |
| | 4 | — | — | — | — | — | — | 1 | — | — | — | — | — | — | — | — | — | — | — | — | — |
| | 2 | — | — | 1 | — | 1 | 1 | 2 | 1 | 1 | 1 | 1 | 1 | 1 | 1 | 1 | 1 | 1 | 1 | — | 1 |
| | 1 | 1 | — | 1 | 1 | 1 | 1 | 1 | 1 | 1 | 1 | 1 | 1 | 1 | 1 | 1 | 1 | 1 | 3 | 3 | 3 |
| 96 | 4 | — | — | 3 | — | 3 | 5 | 2 | 2 | 2 | 4 | 4 | 4 | 3 | 4 | 2 | 2 | 5 | 3 | 1 | 2 |
| | 2 | 2 | 1 | 1 | 1 | 3 | 5 | 1 | 2 | 1 | 4 | 3 | 4 | 3 | 5 | 2 | 2 | 2 | 2 | 3 | 2 |
| | 1 | 1 | 1 | 1 | 1 | 2 | 5 | 1 | 2 | 2 | 5 | 5 | 3 | 4 | 4 | 2 | 2 | 2 | 3 | 2 | 2 |
| 97 | 0.5 | 1 | 1 | 1 | 1 | 1 | 4 | 1 | 2 | 2 | 3 | 3 | 3 | 3 | 4 | 2 | 2 | 2 | 3 | 2 | 2 |
| | 0.25 | 1 | 1 | 1 | 1 | 1 | 2 | 1 | 2 | 1 | 2 | 2 | 1 | 1 | 3 | 1 | 1 | 1 | 1 | 1 | 2 |
| | 4 | — | — | 1 | — | 1 | 5 | 1 | 2 | 2 | 1 | 5 | 2 | 2 | 5 | 2 | 1 | 1 | 3 | 2 | 2 |
| | 2 | 1 | 1 | 2 | 1 | 1 | 4 | 1 | 2 | 2 | 4 | 5 | 2 | 2 | 4 | 2 | 2 | 2 | 3 | 2 | 2 |
| | 1 | 1 | 1 | 1 | 1 | 1 | 1 | 1 | 3 | 3 | 2 | 3 | 1 | 2 | 5 | 1 | 2 | 1 | 1 | 1 | 1 |
| 98 | 0.5 | 1 | 1 | 1 | 1 | 1 | 5 | 1 | 1 | 1 | 1 | 5 | 1 | 1 | 4 | 1 | 1 | 1 | 1 | 1 | 1 |
| | 0.25 | 1 | 1 | 1 | 1 | 1 | 1 | 1 | 1 | 1 | 1 | 2 | 1 | 1 | 5 | 1 | 1 | 1 | 1 | 1 | 2 |
| 104 | 0.5 | 1 | 1 | 1 | 1 | 1 | 1 | 1 | 1 | 1 | 1 | 1 | 1 | 1 | 1 | 1 | 1 | 1 | 1 | 1 | 1 |
| | 0.25 | 1 | 1 | 1 | 1 | 1 | 1 | 1 | 1 | 1 | 1 | 1 | 1 | 1 | 1 | 1 | 1 | 1 | 1 | 1 | 1 |
| 111 | 4 | 1 | 1 | 2 | 1 | 4 | 5 | 1 | 2 | 5 | 4 | 5 | 5 | 5 | 5 | 2 | 3 | 2 | 5 | 2 | 5 |
| | 2 | 1 | 1 | 1 | 1 | 4 | 5 | 1 | 1 | 3 | 2 | 5 | 3 | 5 | 5 | 1 | 2 | 1 | 5 | 1 | 2 |
| | 1 | 1 | 1 | 1 | 1 | 2 | 2 | 3 | 1 | 4 | 2 | 5 | 1 | 2 | 5 | 1 | 1 | 1 | 4 | 1 | 1 |
| 112 | 0.5 | 1 | 1 | 2 | 1 | 3 | 2 | 1 | 2 | 3 | 1 | 5 | 2 | 5 | 5 | 2 | 1 | 2 | 5 | 2 | 2 |
| | 0.25 | 1 | 1 | 2 | 1 | 1 | 1 | 1 | 2 | 2 | 1 | 5 | 3 | 2 | 3 | 2 | 2 | 1 | 3 | 1 | 2 |
| 114 | 2 | 1 | — | 1 | — | — | 3 | 3 | 3 | 2 | 1 | 4 | 1 | 3 | 3 | 3 | 2 | 1 | — | 1 | 1 |
| | 1 | 1 | 1 | 1 | 1 | 1 | 2 | 1 | 1 | 3 | 1 | 5 | 2 | 2 | 2 | 1 | 1 | 1 | 3 | 2 | 2 |
| 115 | 0.5 | 1 | 1 | 1 | 1 | 5 | 4 | 1 | 2 | 2 | 2 | 5 | 2 | 2 | 3 | 3 | 1 | 1 | 2 | 1 | 2 |
| | 0.25 | 1 | 1 | 1 | 1 | 2 | 2 | 1 | 1 | 1 | 1 | 3 | 1 | 2 | 2 | 1 | 1 | 1 | 1 | 1 | 2 |
| 116 | 4 | 1 | — | 1 | 1 | 4 | 5 | 1 | 2 | 4 | 2 | 5 | 3 | 4 | 4 | 3 | 2 | 2 | 5 | 3 | 4 |
| | 2 | 1 | 1 | 2 | 1 | 4 | 2 | 1 | 2 | 3 | 1 | 3 | 2 | 2 | 3 | 1 | 1 | 1 | 3 | 1 | 1 |
| | 1 | 1 | 1 | 1 | 1 | 1 | 1 | 1 | 2 | 1 | 1 | 2 | 1 | 2 | 2 | 1 | 1 | 1 | 1 | 1 | 2 |
| 118 | 0.5 | 1 | 1 | 1 | 1 | 1 | 5 | 2 | 2 | 3 | 2 | 3 | 2 | 2 | 5 | 3 | 1 | 2 | — | 2 | 2 |
| | 0.25 | 1 | 1 | 1 | 1 | 1 | 4 | 2 | 2 | 2 | 1 | 5 | 1 | 2 | 2 | 1 | 1 | 1 | — | 1 | 1 |
| | 1 | 1 | 1 | 1 | 1 | 1 | 4 | 1 | 1 | 1 | 1 | 5 | 1 | 2 | 2 | 3 | 1 | 1 | 5 | 1 | 5 |
| 120 | 8 | — | — | — | — | — | — | — | — | — | — | — | 4 | — | — | — | — | — | — | — | 2 |
| | 4 | — | — | — | — | — | — | — | — | — | — | — | — | — | — | — | — | — | — | — | — |
| | 2 | — | 1 | — | — | 1 | — | — | — | — | — | — | — | — | — | — | — | — | — | — | — |
| | 1 | 1 | 1 | 1 | 1 | 3 | 2 | 1 | 1 | 1 | 1 | 5 | — | 4 | 5 | 3 | — | — | — | 1 | 4 |
| 123 | 0.5 | 1 | 1 | 1 | 1 | 1 | 2 | 1 | 1 | 1 | 1 | 5 | — | 3 | 2 | 1 | — | — | — | 1 | 2 |

TABLE III-continued

| Compound of Example No. | Rate of Application Lbs/Acre | Corn | Cotton | Soybean | Wheat | Alfalfa | Sugar Beat | Rice | Cucumber | Tomato | Preemergence Barnyard Grass | Lambsquarter | Large Crabgrass | Mustard | Pigweed | Foxtail | Wildoat | Velvetleaf | Jimson Weed | Morningglory | Zinnia |
|---|---|---|---|---|---|---|---|---|---|---|---|---|---|---|---|---|---|---|---|---|---|
| 124 | 0.25 | 1 | 1 | 1 | 1 | — | 4 | 1 | — | — | 1 | 3 | 1 | 3 | 2 | — | — | 1 | — | — | — |
|  | 1 | 1 | 1 | 1 | 1 | — | 1 | 1 | — | — | 3 | 5 | 1 | 3 | 5 | 1 | — | 1 | 1 | 1 | 1 |
| 125 | 0.5 | 1 | 2 | 3 | 1 | 2 | 4 | 1 | 3 | 4 | 2 | 5 | 5 | 4 | 4 | 4 | — | 3 | 4 | 1 | 1 |
|  | 1 | 1 | 2 | 2 | 1 | — | 3 | 1 | 3 | 2 | 1 | 4 | 3 | 3 | 3 | 4 | — | 1 | 1 | — | 1 |
| 127 | 0.5 | 1 | 2 | 4 | 1 | 1 | 2 | — | — | 3 | 3 | 4 | 4 | 4 | 4 | 2 | 1 | 2 | 3 | 1 | 3 |
|  | 2 | 1 | 1 | 2 | 1 | — | 1 | 2 | 3 | 3 | 3 | 5 | 4 | 5 | 5 | 3 | — | 1 | 2 | — | 1 |
| 145 | 2 | 2 | 2 | 2 | 1 | 5 | 5 | 2 | 1 | 4 | 1 | 5 | 1 | 3 | 5 | 1 | 1 | 2 | 4 | — | 1 |
|  | 1 | 2 | 1 | 1 | 1 | 5 | 5 | 2 | 3 | 4 | 4 | 5 | 5 | 5 | 5 | 4 | — | 1 | 5 | — | 1 |
| 149 | 2 | 2 | 2 | 2 | 1 | 1 | 5 | 1 | 1 | 4 | 4 | 5 | 5 | 3 | 5 | 4 | 2 | 2 | 4 | 2 | 2 |
|  | 1 | 2 | 1 | 2 | 1 | 1 | 5 | 1 | — | 5 | 5 | 5 | 5 | 4 | 5 | 4 | 2 | 1 | 3 | 3 | 2 |
| 151 | 2 | 2 | 1 | 1 | 1 | 4 | 4 | 2 | 2 | 5 | 3 | 4 | 4 | 2 | 5 | 2 | 1 | 3 | 5 | 2 | 3 |
|  | 1 | 1 | 1 | 3 | 2 | 4 | 2 | — | — | 1 | 2 | 4 | 4 | 3 | 5 | 1 | — | 3 | 3 | 2 | 3 |
| 153 | 2 | 2 | 2 | 2 | 1 | 3 | 5 | 4 | 5 | 5 | 2 | 5 | 5 | 5 | 5 | 5 | 1 | 1 | 5 | 2 | 2 |
|  | 1 | 2 | 2 | 3 | 1 | 4 | 5 | 4 | 5 | 3 | 5 | 5 | 5 | 5 | 5 | 5 | 5 | 3 | 5 | 5 | 4 |
| 155 | 2 | 5 | 3 | 5 | 5 | 5 | 5 | 4 | 5 | 5 | 5 | 5 | 5 | 5 | 5 | 5 | 5 | 5 | 5 | 5 | 3 |
|  | 4 | 4 | 2 | 4 | 4 | 5 | 4 | 3 | 5 | 5 | 5 | 5 | 5 | 5 | 4 | 5 | 4 | 5 | 4 | 2 | 4 |
| 157 | 1 | 3 | 1 | 3 | 2 | 5 | 5 | 4 | 5 | 5 | 5 | 5 | 5 | 4 | 5 | 4 | 3 | 4 | 5 | 4 | 3 |
|  | 0.25 | 3 | 2 | 4 | 3 | 4 | 5 | 3 | 5 | 5 | 3 | 5 | 5 | 5 | 5 | 3 | 2 | 3 | 4 | 2 | 2 |
|  | 0.125 | 2 | 2 | 5 | 2 | 4 | 5 | 2 | 5 | 5 | 2 | 5 | 4 | 5 | 5 | 5 | — | 4 | 4 | 4 | 4 |
| 164 | 4 | 2 | 2 | 5 | 2 | 5 | 4 | 2 | — | 4 | 4 | 5 | 3 | 3 | 5 | 4 | — | 5 | 5 | 5 | 3 |
|  | 2 | 1 | 1 | 4 | 1 | 5 | 4 | 1 | 1 | 3 | 2 | 2 | 4 | 3 | 4 | 3 | — | 5 | 4 | 2 | 2 |
|  | 1 | 1 | 1 | 1 | 1 | — | 2 | — | 1 | 2 | 4 | 5 | 3 | 2 | 4 | 1 | — | 2 | 3 | 3 | 1 |
| 170 | 4 | 1 | 1 | 1 | 1 | 1 | 2 | — | — | — | 4 | 5 | 3 | 2 | 5 | 4 | — | 2 | 5 | 2 | 2 |
|  | 2 | 1 | 1 | 1 | 1 | — | 2 | — | — | 2 | 4 | 5 | 3 | 3 | 4 | — | — | 2 | 3 | 2 | 3 |
|  | 1 | 1 | 1 | 1 | — | — | 4 | — | — | 1 | 2 | 4 | 2 | 4 | 5 | 4 | — | 1 | 4 | 2 | 3 |
| 176 | 0.5 | 1 | 1 | 1 | 1 | — | 1 | — | — | — | 1 | 5 | 1 | 1 | 4 | — | — | 1 | 4 | — | — |
|  | 0.25 | 1 | 1 | 1 | 1 | — | 1 | — | — | — | 1 | 4 | 1 | 2 | 2 | — | — | — | — | — | — |

As pointed out earlier, most of the compounds provided by this invention are potent herbicidal agents when applied at low rates to soil or plant surfaces pre- or post-emergence. Many of the compounds are even more potent when applied to soil and incorporated therein prior to planting of crop seeds. Pre-plant incorporation is particularly preferred when employing a benzamide which displays less than desirable potency or selectivity when surface applied. For example, the compound of Example 52, namely N-[3-(1-methylethyl)-5-isoxazolyl]-2,6-dimethoxybenzamide, failed to retard the vigor of tomato, large crabgrass or pigweed when applied both pre- and post-emergence at 15 pounds per acre. When the compound was applied at 15 pounds per acre and incorporated into the soil prior to seeding, it totally retarded the growth of tomato, wild mustard and lambsquarter, and demonstrated significant herbicidal activity against pigweed, sugarbeets and Jimson-weed.

The herbicidal activity of several compounds provided herein has been determined following pre-plant incorporation of the benzamide. The evaluations were carried out by first formulating an appropriate amount of test compound in 2.5 ml. of a fifty percent mixture of acetone and ethanol. The solution was diluted to 12.5 ml. by the addition of deionized water. The formulated test compound was sprayed onto five quarts of screened, autoclaved greenhouse potting soil. The test compound was incorporated into the soil mixture by tumbling the mixture in a modified cement mixer. The treated soil was transferred to greenhouse flats, and the flats were seeded to various weed and crop species. The seeded flats were maintained in a greenhouse, with sub-irrigation as needed. Plant injury ratings attributable to the test compound were made sixteen days post treatment and planting, utilizing a scale of 0 to 10, wherein 0 is no injury and 10 represents death of the plant species. The results of typical pre-plant soil incorporation studies are presented below in Table IV.

TABLE IV

Pre-plant soil incorporation

| Compound of Example No. | Rate of application lbs/Acre | Alfalfa | Pigweed | Wild Mustard | Lambs-quarter | Sugarbeets | Tomatoes | Jimsonweed |
|---|---|---|---|---|---|---|---|---|
| 46 | 15 | 0 | 5 | 8 | 8 | 6 | 6 | 5 |
| 48 | 15 | 0 | 5 | 10 | 10 | 6 | 5 | 0 |
| 52 | 15 | 0 | 6 | 10 | 10 | 7 | 10 | 5 |
| 65 | 15 | 6 | 10 | 10 | 10 | 6 | 6 | 5 |
| 78 | 15 | 6 | 10 | 10 | 10 | 10 | 5 | 3 |
| 85 | 8 | 0 | 4 | 10 | 9 | 4 | 5 | 2 |
| 100 | 15 | 2 | 8 | 10 | 10 | 9 | 8 | 6 |
| 106 | 15 | 7 | 10 | 10 | 10 | 8 | 6 | 6 |
| 110 | 15 | 0 | 9 | 10 | 8 | 8 | 10 | 9 |
| 121 | 4 | 0 | 3 | 10 | 6 | 3 | 3 | 0 |
| 133 | 8 | 0 | 7 | 10 | 10 | 4 | 3 | 1 |
| 135 | 15 | 0 | 9 | 10 | 10 | 9 | 8 | 5 |
| 136 | 15 | 0 | 2 | 10 | 6 | 4 | 6 | 0 |

Several of the preferred benzamides of the invention have been evaluated in a number of open field studies to determine efficacy, selectivity and crop tolerances. In a typical field trial, the benzamides were applied pre-emergence as an aqueous spray in soil seeded to cereal grains and having weed species present that are common with such crops. The studies routinely involved randomized blocks with four replicates. Observations were made for grain crop vigor, weed control, crop injury, crop emergence, and root injury.

One such field study was carried out in Great Britain to determine the efficacy and selectivity of preferred benzamides when surface applied pre-emergence to soil seeded to common wheat. Observations were made twenty-five days post-application to determine the vigor of the treated wheat plants compared to untreated controls, and to determine the amount of control of various weed species effected by the benzamides. The results of the field test are presented below in Table V. The data presented for crop vigor is the comparison of treated wheat to untreated wheat, the untreated controls being assigned a vigor rating of 100 percent. Weed control ratings are given in percentage of control compared to untreated control plots based upon visual inspection.

TABLE V

| Compound Applied | Rate Kg/ha | Crop Vigor Rating | Blackgrass Control | Catchweed Bedstraw Control | Wild Chomomile Control | Ladys-thumb Control | Chickweed Control |
|---|---|---|---|---|---|---|---|
| N—[3-(1-ethyl-1-methyl-butyl)-5-isoxazolyl]-2,6-dimethoxybenzamide (Compound of Ex. 14) | 0.25 | 96 | 40 | 20 | 100 | 91 | 100 |
| | 0.50 | 93 | 68 | 8 | 100 | 100 | 100 |
| | 0.75 | 96 | 53 | 5 | 100 | 100 | 100 |
| | 1.0 | 93 | 73 | 27 | 100 | 100 | 100 |
| N—[3-(1-methylcyclohexyl)-5-isoxazolyl]-2,6-dimethoxybenzamide (Compound of Ex. 17) | 0.25 | 97 | 56 | 0 | 100 | 100 | 100 |
| | 0.50 | 98 | 59 | 3 | 100 | 100 | 100 |
| | 0.75 | 94 | 61 | 3 | 100 | 100 | 100 |
| | 1.0 | 93 | 54 | 5 | 100 | 100 | 100 |
| N—[3-(1-ethylcyclohexyl)-5-isoxazolyl]-2,6-dimethoxybenzamide (Compound of Ex. 19) | 0.25 | 96 | 83 | 18 | 100 | 94 | 100 |
| | 0.50 | 97 | 55 | 28 | 100 | 98 | 100 |
| | 0.75 | 96 | 83 | 25 | 100 | 100 | 100 |
| | 1.0 | 93 | 84 | 63 | 100 | 100 | 100 |
| N—[3-(1,1-dimethylethyl)-5-isoxazolyl]-2,6-dimethoxybenzamide (Compound of Ex. 6) | 1.0 | 96 | 60 | 10 | 100 | 83 | 100 |
| N—[3-(1-ethyl-1-methyl- | 1.0 | 92 | 66 | 93 | 100 | 100 | 100 |

TABLE V-continued

| Compound Applied | Rate Kg/ha | Crop Vigor Rating | Blackgrass Control | Catchweed Bedstraw Control | Wild Chomomile Control | Ladysthumb Control | Chickweed Control |
|---|---|---|---|---|---|---|---|
| propyl)-5-isoxazolyl]-2,6-dimethoxybenzamide (Compound of Ex. 1) | | | | | | | |
| Untreated control | | 100 | 0 | 0 | 0 | 0 | 0 |

A field study was carried out in Brazil to evaluate the herbicidal activity and crop tolerances of certain preferred benzamides compared to untreated controls and to commercial herbicides trifluralin and metribuzin. The herbicides were applied as an aqueous spray and were pre-plant incorporated with a disc and harrow. Treated and untreated plots were individually seeded to peanuts, soybeans, cotton and corn. Observations were then made sixteen and thirty-six days post-treatment.

Treated plots were visually compared with untreated controls to determine percent of crop emergence, percent of crop injury, percent of crop stand, and percent of root injury. Table VI which follows presents the effects of various herbicides on crops. Table VII presents the degree to which the various herbicides controlled weed species commonly encountered in the indicated crops.

TABLE VI

| Compound of Example No. | Rate kg/ha | % Crop Emergence at 16 Days | % Crop Injury at 16 Days | % Crop Injury at 36 Days | % Crop Stand at 16 Days | % Root Injury at 36 Days |
|---|---|---|---|---|---|---|
| Peanuts | | | | | | |
| 1 | 0.13 | 93 | 7 | 17 | 101 | 0 |
| | 0.25 | 83 | 20 | 27 | 87 | 0 |
| | 0.50 | 70 | 37 | 37 | 82 | 40 |
| | 1.0 | 70 | 40 | 53 | 83 | 23 |
| 6 | 1.0 | 73 | 20 | 3 | 83 | 0 |
| | 2.0 | 83 | 13 | 13 | 90 | 10 |
| 28 | 0.13 | 83 | 20 | 13 | 92 | 0 |
| | 0.25 | 93 | 13 | 17 | 102 | 0 |
| | 0.50 | 83 | 17 | 20 | 92 | 0 |
| | 1.0 | 80 | 30 | 30 | 105 | 10 |
| 61 | 0.13 | 93 | 7 | 0 | 92 | 0 |
| | 0.25 | 87 | 13 | 13 | 98 | 0 |
| | 0.50 | 77 | 17 | 20 | 84 | 0 |
| | 1.0 | 67 | 37 | 40 | 80 | 28 |
| Trifluralin | 0.96 | 80 | 27 | 20 | 80 | 0 |
| Metribuzin | 0.49 | 77 | 50 | 47 | 92 | 0 |
| Untreated Control | | 100 | 0 | 0 | 100 | 0 |
| Soybeans | | | | | | |
| 1 | 0.13 | 53 | 37 | 30 | 51 | 0 |
| | 0.25 | 43 | 47 | 33 | 42 | 0 |
| | 0.50 | 37 | 57 | 53 | 26 | 0 |
| | 1.0 | 13 | 87 | 77 | 7 | 0 |
| 6 | 1.0 | 93 | 7 | 3 | 88 | 0 |
| | 2.0 | 97 | 0 | 0 | 103 | 0 |
| 28 | 0.13 | 87 | 10 | 10 | 81 | 0 |
| | 0.25 | 80 | 13 | 27 | 89 | 0 |
| | 0.50 | 60 | 40 | 27 | 46 | 0 |
| | 1.0 | 43 | 53 | 40 | 30 | 0 |
| 61 | 0.13 | 97 | 0 | 0 | 99 | 0 |
| | 0.25 | 87 | 17 | 13 | 77 | 0 |
| | 0.50 | 63 | 30 | 27 | 54 | 0 |
| | 1.0 | 37 | 60 | 47 | 31 | 0 |
| Trifluralin | 0.96 | 73 | 30 | 17 | 60 | 0 |
| Metribuzin | 0.49 | 90 | 13 | 7 | 87 | 0 |
| Untreated Control | | 100 | 0 | 0 | 100 | 0 |
| Cotton | | | | | | |
| 1 | 0.13 | 83 | 17 | 17 | 96 | 0 |
| | 0.25 | 80 | 23 | 30 | 85 | 0 |
| | 0.50 | 70 | 33 | 30 | 80 | 0 |
| | 1.0 | 43 | 53 | 43 | 38 | 0 |
| 6 | 1.0 | 90 | 10 | 0 | 97 | 0 |
| | 2.0 | 87 | 13 | 3 | 104 | 0 |
| 28 | 0.13 | 97 | 3 | 0 | 112 | 0 |
| | 0.25 | 90 | 10 | 23 | 92 | 0 |
| | 0.50 | 80 | 27 | 13 | 97 | 0 |
| | 1.0 | 90 | 13 | 20 | 84 | 0 |
| 61 | 0.13 | 93 | 7 | 0 | 117 | 0 |
| | 0.25 | 73 | 17 | 7 | 97 | 0 |
| | 0.50 | 90 | 17 | 7 | 94 | 0 |
| | 1.0 | 80 | 17 | 23 | 94 | 0 |
| Trifluralin | 0.96 | 93 | 20 | 23 | 108 | 0 |
| Metribuzin | 0.49 | 37 | 73 | 67 | 24 | 0 |

TABLE VI-continued

| Compound of Example No. | Rate kg/ha | % Crop Emergence at 16 Days | % Crop Injury at 16 Days | % Crop Injury at 36 Days | % Crop Stand at 16 Days | % Root Injury at 36 Days |
|---|---|---|---|---|---|---|
| Control | | 100 | 0 | 0 | 100 | 0 |
| | | | Corn | | | |
| 1 | 0.13 | 93 | 30 | 27 | 86 | 0 |
| | 0.25 | 90 | 33 | 30 | 88 | 0 |
| | 0.50 | 87 | 43 | 37 | 89 | 0 |
| | 1.0 | 77 | 57 | 60 | 85 | 37 |
| 6 | 1.0 | 97 | 3 | 3 | 94 | 0 |
| | 2.0 | 93 | 13 | 3 | 90 | 3 |
| 28 | 0.13 | 97 | 7 | 10 | 94 | 0 |
| | 0.25 | 83 | 33 | 17 | 84 | 0 |
| | 0.50 | 90 | 13 | 20 | 79 | 0 |
| | 1.0 | 90 | 27 | 27 | 91 | 0 |
| 61 | 0.13 | 97 | 17 | 3 | 95 | 0 |
| | 0.25 | 93 | 13 | 7 | 95 | 0 |
| | 0.50 | 87 | 30 | 13 | 86 | 0 |
| | 1.0 | 90 | 40 | 30 | 83 | 0 |
| Trifluralin | 0.96 | 77 | 47 | 37 | 74 | 3 |
| Metribuzin | 0.49 | 77 | 60 | 57 | 84 | 0 |
| Control | | 100 | 0 | 0 | 100 | 0 |

TABLE VII

| Compound of Example No. | Rate kg/ha | % Weed Control Annual Broadleaves | % Weed Control Other Broadleaves | % Weed Control Southern Sanbur | % Weed Control Goosegrass | % Weed Control Rhynchelytrum Roseum | % Weed Control Sida Spp. |
|---|---|---|---|---|---|---|---|
| 1 | 0.13 | 7 | 0 | 7 | 17 | 0 | 10 |
| | 0.25 | 83 | 10 | 27 | 37 | 20 | 10 |
| | 0.50 | 90 | 17 | 57 | 60 | 27 | 0 |
| | 1.0 | 93 | 60 | 73 | 80 | 70 | 13 |
| 6 | 1.0 | 0 | 0 | 20 | 63 | 0 | 0 |
| | 2.0 | 7 | 0 | 30 | 37 | 0 | 0 |
| 28 | 0.13 | 0 | 0 | 20 | 7 | 7 | 3 |
| | 0.25 | 13 | 0 | 43 | 60 | 7 | 0 |
| | 0.50 | 53 | 3 | 27 | 33 | 0 | 0 |
| | 1.0 | 40 | 10 | 40 | 33 | 23 | 10 |
| 61 | 0.13 | 0 | 0 | 0 | 0 | 0 | 0 |
| | 0.25 | 0 | 0 | 0 | 0 | 0 | 0 |
| | 0.50 | 73 | 10 | 13 | 17 | 37 | 0 |
| | 1.0 | 73 | 30 | 30 | 85 | 37 | 0 |
| Trifluralin | 0.96 | 53 | 7 | 97 | 97 | 87 | 0 |
| Metribuzin | 0.49 | 30 | 27 | 70 | 87 | 83 | 70 |
| Control | | 0 | 0 | 0 | 0 | 0 | 0 |

A field study was carried out in Canada to determine the herbicidal efficacy and crop tolerance of various preferred benzamides alone and in combination with the commercial herbicide trifluralin. The herbicides were applied as an aqueous spray, and the field plots were seeded to the cereal grain barley and various weed species, after which the herbicides were soil incorporated utilizing a diamond harrow. Crop injury ratings were made visually on a scale of 0–10, with 0 being no injury and 10 being plant death. All observations reported were made twenty-six days post seeding and application, except crop yield data were determined eighty-four days following treatment. The percent of weed control of various weed species occurring in cereal crops such as barley were determined by visual comparison with untreated control plots. The results of the field test are present below in Table VIII.

TABLE VIII

| Compound of Example No. | Rate kg/ha | Crop Injury | % Crop Yield | % Weed Control White Mustard | % Weed Control Redroot Pigweed | % Weed Control Lambsquarter | % Weed Control Green Smartweed |
|---|---|---|---|---|---|---|---|
| | | | Barley | | | | |
| Trifluralin | 0.7 | 0 | 119 | 0 | 95 | 40 | 0 |
| Control | | 0 | 100 | 0 | 0 | 0 | 0 |
| 6 | 1.1 | 0 | 143 | 95 | 85 | 40 | 20 |
| | 2.2 | 0 | 111 | 95 | 95 | 75 | 0 |
| 6 + Trifluralin | 1.1 + 0.7 | 0 | 119 | 90 | 95 | 40 | 0 |
| | 1.68 + 0.7 | 0 | 107 | 90 | 95 | 40 | 0 |
| | 2.2 + 0.7 | 0 | 99 | 100 | 95 | 70 | 20 |
| 27 | 1.1 | 0 | 147 | 100 | 90 | 50 | 20 |
| | 2.2 | 0 | 87 | 100 | 95 | 75 | 0 |
| 27 + Trifluralin | 0.56 + 0.7 | 0 | 123 | 95 | 90 | 20 | 0 |
| | 1.1 + 0.7 | 0 | 107 | 95 | 90 | 50 | 0 |
| | 1.68 + 0.7 | 0 | 135 | 100 | 95 | 40 | 0 |
| | 2.2 + 0.7 | 0 | 107 | 95 | 95 | 40 | 10 |
| 28 | 1.1 | 0 | 107 | 100 | 70 | 45 | 10 |
| | 2.2 | 0 | 103 | 100 | 95 | 75 | 0 |

TABLE VIII-continued

| Compound of Example No. | Rate kg/ha | Crop Injury | % Crop Yield | Barley % Weed Control White Mustard | % Weed Control Redroot Pigweed | % Weed Control Lambsquarter | % Weed Control Green Smartweed |
|---|---|---|---|---|---|---|---|
| 28 + Trifluralin | 0.56 + 0.7 | 0 | 119 | 95 | 95 | 40 | 0 |
| | 1.1 + 0.7 | 0 | 111 | 95 | 75 | 50 | 0 |
| | 1.68 + 0.7 | 0 | 139 | 95 | 95 | 50 | 0 |
| | 2.2 + 0.7 | 0 | 119 | 100 | 95 | 40 | 10 |
| 101 | 1.1 | 0 | 111 | 95 | 80 | 30 | 0 |
| | 2.2 | 0 | 111 | 95 | 95 | 70 | 0 |
| 101 + Trifluralin | 0.56 + 0.7 | 0 | 119 | 95 | 90 | 40 | 0 |
| | 1.1 + 0.7 | 0 | 119 | 85 | 95 | 75 | 0 |
| | 168 + 0.7 | 0 | 131 | 95 | 95 | 50 | 0 |
| | 2.2 + 0.7 | 0 | 123 | 95 | 95 | 40 | 10 |

As can be seen from the data presented above, the benzamides of this invention exhibit a broad-spectrum of herbicidal activity. Some of the compounds also have demonstrated a certain amount of insecticidal activity. A further important embodiment of this invention is a herbicidal method for killing and controlling the growth of unwanted vegetation which comprises applying to the locus where vegetative control is desired a herbicidally effective amount of a benzamide of this invention. Since the compounds are capable of killing and retarding the growth of a number of weeds and undesirable plants which commonly grow in areas used for growing desired crops such as cereal grains and the like, the method of the invention is particularly applicable to practice in such crops. For example, the benzamides are very effective in killing and retarding the growth of weeds such as barnyardgrass, lambsquarter, yellow foxtail, fall panicum, wild buckwheat, crabgrass, mustard, pigweed, cocklebur, velvet-leaf, jimsonweed, morningglory, ragweed, zinnia and a number of other vegetative species which are known to comprise unwanted weed and grass vegetation. The compounds are also effective in controlling the growth of perennial weeds. For example, the compounds of Example 1 and of Example 6 have demonstrated effectiveness against noxious plants such as silverleaf nightshade. While the compounds are toxic to such undesired weeds and grasses, they do not adversely affect the growth of desirable crops such as the cereal grains, for example wheat, barley, oats and rice. The compounds can also be employed in combating undesired vegetative growth in crops such as corn, soybeans, peanuts, cotton and related crops. The compound of Example 6 appears particularly suited, for instance, in controlling weeds in cotton, soybeans, peanuts, peas and the like. The herbicidal selectivity of the benzamides is an important benefit to be realized in the practice of the invention. The compounds can also be utilized in the control of unwanted vegetation in non-crop land, for instance in a chemical fallow land program, particularly in fallow wheatland and the like.

The benzamides of the invention can also be employed in combination with any of several known and commonly used herbicides. For example, a preferred method of herbicidal control according to this invention employs a benzamide of the invention used in conjunction with one or more other herbicides, ideally one or more grass herbicides, for example a dinitroaniline herbicide such as trifluralin, butralin, dinitramine, nitralin, profluralin, prodiamine, oryzalin, isopropalin, ethalfluralin, benefin, fluchloralin, pendimethalin, and the like. Other herbicides to be employed in combination with the present benzamides include alachlor, ametryn, amitrole, atrazine, bentazon, bifenox, butachlor, butam, buthidazole, chloramben, chlorbromuron, cyanazine, dichloroprop, dinoseb, fenac, linuron, methazole, metolachlor, metribuzin, nitrofen, pebulate, prometon, prometryn, propachlor, simazine, terbutryn, triallate, trichopyr, propanil and the like.

The use of the benzamides of this invention in combination with other herbicides provides for an even broader range of weed control than generally can be realized with either the benzamides alone or the other herbicides such as trifluralin alone. Such combinations are particularly preferred when practicing the method in cereal grains.

The benzamides provided herein can also be applied in conjunction with agricultural chemicals which are utilized to control pests other than unwanted vegetative growth. The benzamides of this invention lend themselves well to combination with other agricultural chemicals such as insecticides, fungicides, nematicides, and other herbicides as may be desirable and convenient.

In carrying out the method of this invention, a benzamide of the invention can be applied post-emergence to soil or to the foilage of plants whose growth is to be controlled, or pre-emergence to the locus where the growth of unwanted vegetation is to be controlled. A preferred herbicidal method comprises application of the benzamide pre-emergence. The compounds can be applied to the surface of soil in which the growth of unwanted weeds and grasses is to be eliminated or retarded, or if desired the compounds can be incorporated into the soil, for example by use of conventional tillage equipment such as the disc, harrow or the like. Soil incorporation or surface application may be employed when the benzamides are utilized in combination with other herbicides such as trifluralin or the like. Also, pre-emergence soil incorporation is preferred for compounds having less than desired activity when surface applied but not incorporated.

The compounds of the invention are effective in selectively killing and controlling the growth of unwanted vegetation when applied at a herbicidally-effective rate. In carrying out the method of the invention, and in the case of using the benzamides as pre-emergence herbicides, the active ingredient will be applied to the locus where weed control is desired at a rate of about 0.05 to about 15 pounds per acre, and more desirably at a rate of about 0.1 to about 5 pounds per acre. The most active compounds will generally be applied at about 0.1 to about 2 pounds per acre. It will of course be understood by those having skill in the herbicidal art that such rates of application may vary, depending upon several factors, including the type of locus being treated, the particular benzamide being utilized, the particular weeds or grasses to be killed or controlled, whether the method is being practiced in cropland or fallow land, whether or not the herbicide is being incorporated into the soil, whether or not the benzamide is being utilized in conjunction with other agricultural chemicals, for instance other herbicides such as pendimethalin or simazine. Moreover, while the above-suggested rates are preferred for pre-emergent weed control, the compounds can be applied post-emergence at rates of about 1 to about 20 pounds per acre, and more preferably at about 2 to about 10 pounds per acre.

The herbicidal method provided by this invention can be carried out employing any of the benzamide herbicides defined herein, but as noted earlier, the method is preferably practiced employing an N-isoxazolyl or thiadiazolyl-2,6-dialkoxybenzamide. An especially preferred method employs a benzamide selected from N-[3-(1,1-dimethylethyl)-5-isoxazolyl]-2,6-dimethoxybenzamide, N-[3-(1-ethyl-1-methylpropyl)-5-isoxazolyl]2,6-dimethoxybenzamide, N-[5-(1-ethyl-1-methylpropyl)-1,3,4-thiadiazol-2-yl]-2,6-dimethoxybenzamide, N-[3-(1-ethylcyclohexyl)-5-isoxazolyl]-2,6-dimethoxybenzamide and N-[5-(1-ethyl-1-methylpropyl)-3-isoxazolyl]-2,6-dimethoxybenzamide. Another preferred herbicidal method employs a pyridazinyl benzamide, for instance N-[6-(1-ethyl-1-methylpropyl)-pyridazin-3-yl]-2,6-dimethoxybenzamide, or the like. Such compounds can be employed alone at rates of about 0.1 to about 2 pounds per acre, or if desired they can be employed in combination with other herbicides such as trifluralin, ametryn, alachlor or the like. When utilized in combination with other herbicides, the exact rate of application for each of the component herbicides will be determined by several factors, including the specific weeds and grasses to be controlled, the particular herbicides used in combination, the weed population, and related factors. Generally, the benzamides will be employed in combination with other herbicides in a ratio of about one to about five parts by weight of benzamide and about five to about one part by weight of another herbicide. A preferred combination will contain the component herbicides in a weight ratio of about one to one. Such combination will be applied at a rate which is effective to control the unwanted vegetation to the desired degree. The respective herbicides can be applied separately or as a single mixture, for example, a tank mix or the like.

The benzamides of this invention ideally are suitably formulated for use as described above. Herbicidal formulations comprising a benzamide herbicide of the invention admixed with an agronomically acceptable diluent, excipient or carrier therefor thus form a further important embodiment of the invention. Such compositions will typically contain from about 1 to about 95 percent by weight of active herbicide, and more generally about 10 to about 60 percent. The formulations may take the form of solid powders, dusts, granules; aqueous or non-aqueous sprays or drenches; concentrates, for example emulsifiable concentrates and the like; wettable powders, and any of the other forms commonly found in the agriculture art for herbicides.

Agronomically acceptable carriers, diluents and excipients commonly utilized to form powders, dusts, granules and the like include talc, diatomaceous earth, silica, pyrophyllite, attapulgite clays and the like. It is often desirable to formulate a compound of the invention as a granule for convenient pre-emergence application to soil. Such formulation generally is prepared by dissolving the benzamide herbicide in a suitable solvent such as kerosene or aromatic naphtha, and applying the solution to a carrier such as montmorillonite clay granules or the like. Another procedure which can be employed comprises simply dispersing an active ingredient in a dough composed of a suitable carrier, for instance damp clay, and then drying and grinding the clay to provide the formulated granules at the desired particle size.

The benzamides of the invention are also conveniently formulated as concentrated compositions which are diluted prior to application, for instance by the addition of water or other suitable diluent to make a dispersion, emulsion or the like. Typical concentrated formulations which are in the form of solids are wettable powders. Wettable powders comprise a finely-divided intimate mixture of an inert carrier or excipient, a benzamide herbicide, and a suitable surfactant. Commonly utilized inert carriers which are agronomically acceptable include the diatomaceous earths, the various clays such as attapulgite clays or kaolin clays, or silica. Surfactants generally are present in about 0.5 to about 10 percent by weight of the wettable powder, with the benzamide herbicide being present in about 10 to about 60 percent by weight. Any of several known surfactants can be employed in the wettable powder formulations, including any of the sulfonated lignins, the condensed naphthalenesulfonates, the alkylbenzenesulfonates, the alkyl sulfates, as well as the nonionic surfactants such as the ethylene oxide adducts of phenols. The wettable powders which are thus comprised generally are diluted with water or the like prior to application, so that the dispersion or final mixture contains from about 0.1 to about 5.0 percent by weight of the active benzamide herbicide. Such formulation is then applied as a spray or the like by conventional sprayers or other agricultural chemical applicators.

Another commonly utilized formulation type to be employed with the benzamide herbicides are the emulsifiable concentrates. Such formulations are comprised of a benzamide herbicide admixed with a carrier such as a water immiscible organic solvent and an emulsifying agent. Water miscible cosolvents may be utilized in conjunction with the immiscible solvent to improve solubility of the benzamide. Commonly used solvents include toluene, xylene, chlorotoluene, benzene, methyl isobutyl ketone, cyclohexanone, naphtha and the like. Aqueous suspensions employing water as a diluent also are contemplated. Emulsifiers which can be employed include the common surfactants and blends of surfactants, for example the alkyl and aryl sulfonates, ethoxylated alkyl phenols, ethoxylated alkyl ethers, the nonoxynols, oxysorbics, allinols, allinates and other nonionic and anionic surfactants. The surfactant may be present in about 0.5 to about 10 percent by weight. Such concentrates, like the wettable powder formulations, are diluted prior to application, for instance by the addition of the appropriate amount of water to provide a mixture having the desired concentration of active ingredient.

As noted above, the benzamides provided herein are especially useful in combination with other herbicides in order to achieve the range and specificity of weed control desired. A typical method for employing a combination of benzamide herbicide and another herbicide such as trifluralin, terbutryn, or the like, comprises mixing and diluting just prior to application the individual formulations of the respective individual herbicides. The mixing can be carried out, for example, in the tank of a conventional spraying apparatus. A typical combination of a benzamide of this invention with a herbicide such as trifluralin can be prepared by tank mixing at the site of application a wettable powder formulation of benzamide with an emulsifiable concentrate of trifluralin. Such tank-mixed combination will be applied to soil and if desired incorporated therein at a rate such that each active ingredient is present at about 0.5 to about 2 pounds per acre. Such combination provides excellent pre-emergence control of a wide variety of unwanted vegetative species.

The following examples further illustrate typical herbicidal compositions and their use as provided by this invention.

EXAMPLE 178

| Wettable Powder | |
|---|---|
| Ingredient | Concentration by Weight (Percent) |
| N—[3-(1-ethyl-1-methylpropyl)-5-isoxazolyl]-2,6-dimethoxybenzamide (the compound of Example 1) | 50 |
| Igepal CA-630, a polyoxyethylene octyl phenol nonionic wetting agent - GAF Corporation | 5 |
| Bardens Clay | 45 |

The benzamide herbicide is blended to uniformity with the adjuvants and milled to form a free flowing powder that will be wetted and suspensible in water at or near the site of application to form a sprayable mixture. The formulation is sprayed on the locus where vegetative control is desired at a volume so that the active ingredient is applied at about 0.1 to about 2 pounds per acre.

EXAMPLE 179

| Wettable Powder | |
|---|---|
| Ingredient | Percent by Weight |
| N—[5-(1-ethyl-1-methylpropyl)-1,3,4-thiadiazol-2-yl]-2,6-dimethoxybenzamide (the compound of Example 61) | 50 |
| Stepanol ME, a technical grade of sodium lauryl sulfate, Stepan Chemical Corp. | 4 |
| Reax 45L, a lignosulfonate dispersant, Westvaco Corporation | 6 |
| Zeolex-7, a precipitated hydrated silicate, J.M. Huber Corporation | 2 |
| Barden Clay, a hydrated aluminum silicate, J.M. Huber Corporation | 38 |

The ingredients are blended and pulverized to provide a free flowing powder that can be suspended in water for convenient spray application. The aqueous spray will be applied at about 5 to about 50 gallons per acre for an application rate of about 1 to about 5 pounds per acre of active benzamide.

EXAMPLE 180

| Aqueous Suspension | |
|---|---|
| Ingredient | Percent by Weight |
| N—[3-(1,1-dimethylethyl)-5-isoxazolyl]-2,6-dimethoxybenzamide (the compound of Example 6) | 43 |
| Polyfon H, an anionic lignosulfonate wetting agent and dispersant, Westvaco Corporation | 4 |
| Min-u-gel 200, a clay-type gelling agent, The Floridin Company | 2 |
| Antifoam C Dow Corning Corp. | 0.05 |
| Water | 50.95 |
| | 100.00% |

The ingredients are mixed and finely ground to uniformity to provide a suspension of active ingredient. The suspension is diluted with additional water and applied as a spray to the locus to be treated.

EXAMPLE 181

| Granular Formulation | |
|---|---|
| Ingredient | Percent by Weight |
| N—[5-[1,1-dimethyl-2-(methylthio)-ethyl]-1,3,4-thiadiazol-2-yl]-2,6-dimethoxybenzamide (the compound of Example 64) | 5 |
| Heavy aromatic naphtha | 5 |
| Florex 30/60, granular clay, Floridin Co. | 90 |

The benzamide is substantially dissolved in the heavy aromatic naphtha and sprayed onto clay granules of substantially uniform size, ideally less than about 1.0 cubic millimeter, preferably of the 30/60 size range. The granular formulation is surface applied to soil so that the active ingredient is present at about 3 to about 10 pounds per acre.

EXAMPLE 182

| Dust Formulation | |
|---|---|
| Ingredient | Percent by Weight |
| N—[3-(1-ethyl-1-methylpropyl)-1H—pyrazol-5-yl]-2,6-dimethoxybenzamide (the compound of Example 115) | 5 |
| Diatomite, a diatomaceous earth, Witco Chemical Corporation, Inorganic Specialties Division | 95 |

The benzamide herbicide is dry mixed with the diatomaceous earth diluent. The mixture is ground to a fine powder of uniform particle size of about 10 to about 40 microns. If a more concentrated mixture is employed (e.g. about 30 to about 50% active), the formulation can be diluted by the addition of additional excipient such as silica or clay at the site of application. The dust thus formed is surface applied by conventional ground equipment, to the soil surface where vegetative control is desired, or if desired the dust can be applied by conventional aircraft units.

EXAMPLE 183

| Tank-Mix Composition | |
|---|---|
| Ingredient | Percent by Weight |
| N—[5-(1-ethyl-1-methylpropyl)-4H—1,2,4-triazol-3-yl]-2,6-dimethoxy benzamide (the compound of Example 118) 50WP | 60 |
| N,N—diethyl-2,6-dinitro-3-amino-4-trifluoromethyl aniline (dinitramine) 2EC | 40 |

A wettable powder formulation containing 50% by weight of the benzamide of Example 118 is dispersed in water and the mixture is agitated while an aqueous suspension of emulsifiable concentrate (2 lbs/gal) formulation of the dinitroaniline herbicide is added. The resulting mixture is agitated and sprayed on the soil surface and incorporated therein at the rate of about 1 pound per acre of benzamide and about 0.67 pound per acre of the dinitroaniline. The soil can then be seeded to soybeans or the like, and the crop is grown substantially free of unwanted vegetation such as crabgrass, fall panicum, purslane and the like. The yield and quality of the desired crop is thereby greatly improved.

EXAMPLE 184

| Tank-mix Composition | |
|---|---|
| Ingredient | Percent by Weight |
| N—[5-(1-ethyl-1-methylpropyl)-1,3,4-thiadiazol-2-yl]-2,6-diethylbenzamide (the compound of Example 63) 50WP | 50 |
| N,N—di-n-propyl-2,6-dinitro-3-amino-4-trifluoromethylaniline (prodiamine) 50WP | 50 |

A 50% wettable powder formulation of the benzamide is mixed with an aqueous suspension of a 50% wettable powder of the prodiamine. The mixture is agitated and sprayed on soil where weed control is desired. The rate of application will be about 30 gallons per acre such that each active ingredient is applied at about 0.75 pounds per acre. The mixture is preferably incorporated into the soil, for instance by discing, and then the soil is planted to cotton, soybeans, sugarcane, or the like.

EXAMPLE 185

| Tank-mix Composition | |
|---|---|
| Ingredient | Percent by Weight |
| N—[5-(1-propylcyclohexyl)-1,3,4-thiadiazol-2-yl]-2,6-dimethoxy benzamide (the compound of Example 105) 30WP | 30 |
| N,N—di-n-propyl-2,6-dinitro-4-trifluoromethylaniline (trifluralin) 4EC | 70 |

A 30% wettable powder formulation of the benzamide of Example 105 is dispersed in water and agitated while an emulsifiable concentrate (4 lbs/gal) formulation of trifluralin is added portion-wise. The tank-mixed aqueous mixture is sprayed onto soil and incorporated for the control of chickweed, kochia, pigweed, Russian thistle, lambsquarters and the like. The treated soil can be seeded to cereal grains such as wheat, rye, oats, barley, and the like. Such crops grow substantially unaffected by undesired vegetative growth.

EXAMPLE 186

| Wettable Powder | |
|---|---|
| Ingredient | Concentration by Weight (Percent) |
| N—[6-(1-ethyl-1-methylpropyl)-pyridazin-3-yl]-2,6-dimethoxybenzamide (the compound of Example 157) | 51.5 |
| Sellogen HR wetting agent (Diamond Shamrock Corp.) | 5.0 |
| Polyfon O, lignosulfonate dispersant (Westvaco Corp.) | 5.0 |
| Zeolex 7, a precipitated hydrated silica bulking agent, (J.M. Huber Corp) | 5.0 |
| Barden Clay | 33.5 |
| | 100.0 |

EXAMPLE 187

| Wettable Powder | |
|---|---|
| Ingredient | Concentration by weight (Percent) |
| N—[6-(1,1-dimethylethyl)-pyridazin-3-yl]-2,6-dimethoxythiobenzamide | 50.0 |
| Sellogen HR | 5.0 |
| Polyfon 0 | 5.0 |
| Barden Clay | 40.0 |
| | 100.0 |

EXAMPLE 188

| Aqueous Suspension | |
|---|---|
| Ingredient | Percent by Weight |
| N—[3-(1,1-dimethylethyl)-5-isoxazolyl]-2,6-diethoxy-thiobenzamide | 45.00 |
| Emulphor, polyoxyethylated vegetable oil wetting agent (GAF Corp.) | 5.00 |
| Atflow, suspending agent (ICI Americas Inc..) | 5.00 |
| Water | 45.00 |
| | 100.00% |

EXAMPLE 189

Combination use

A 4EC formulation of trifluralin is applied to soil prior to seeding. The trifluralin, at about 0.5 pound per acre, is incorporated into the soil by use of a double disc. The soil is seeded to soybeans, and then a 50% wettable powder formulation of N-[3-(1,1-dimethylethyl)-5-isoxazolyl]-2,6-dimethoxybenzamide (the compound of Example 6) is suspended in water and surface sprayed on the planted soil. The active benzamide is present at about 1.5 pounds per acre. The treatment permits the growth of the desired soybeans without undesirable growth of weeds such as lambsquarter, pigweed, and the like.

A particularly preferred herbicidal method according to this invention employs the benzamide of Example 1, namely N-[3-(1-ethyl-1-methylpropyl)-5-isoxazolyl]-2,6-dimethoxybenzamide. Such compound is especially effective when employed in combination with other herbicides such as trifluralin. The use of such benzamide, as well as the combination, is contemplated to be of major importance in the control of unwanted vegetation in cereal grains such as wheat, oats, barley and the like.

The benzamides provided by this invention are also useful in the control of unwanted vegetation such as broadleaf weeds in orchards and arbors. The compounds have demonstrated excellent selective herbicidal activity in citrus crops such as orange and lemon orchards. The compounds are also expected to be useful in the control of weeds in vines such as grapes and the like, as well as in crops such as sugarcane. The compounds additionally have exhibited plant growth regulator activity, for instance in the form of improved yields of grain and the like and in reducing stalk height. The compounds also have demonstrated utility as aquatic herbicides, and can thus be employed in the control of sago pondweed, duckweed, naiad, milfoil, cabomba, hydrilla verticillata, and similar weeds that grow in streams, ponds and other water areas. The compound of Example 1, for instance, when evaluated as an aquatic herbicide at 1.0 ppm, caused from 87 to 90 percent control of hydrilla, milfoil and sago at fourteen days post treatment. Because of their herbicidal activity against aquatic weeds, the compounds are well suited to the control of weeds in crops such as rice.

I claim:

1. An N-aryl benzamide of the formula

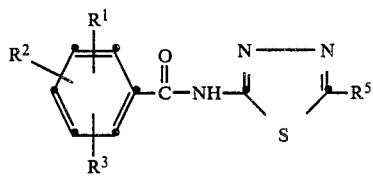

wherein:
$R^1$ is hydrogen or $C_1$-$C_4$ alkoxy;
$R^2$ is $C_1$-$C_4$ alkylthio or $C_1$-$C_4$ alkoxy;
$R^3$ is $C_1$-$C_4$ alkyl, $C_1$-$C_4$ alkylthio, or $C_1$-$C_4$ alkoxy;
$R^5$ is

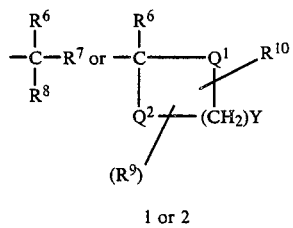

wherein:
$R^6$ is $C_1$-$C_4$ alkyl, $C_2$-$C_4$ alkenyl, $C_2$-$C_4$ alkynyl, $C_1$-$C_6$ alkoxy, or $C_1$-$C_6$ alkylthio;
y is an integer from 0 to 4;
$R^7$ and $R^8$ independently are $C_1$-$C_{13}$ alkyl;
$R^9$ and $R^{10}$ independently are hydrogen, halogen, $C_1$-$C_4$ alkyl, or $C_2$-$C_4$ alkenyl;
$Q^1$ and $Q^2$ are $CH_2$; and
the agronomically acceptable salts thereof.

2. A compound of claim 1 selected from the group consisting of:
N-[5-(1,1-dimethyl-2-(methylthioethyl)-1,3,4-thiadiazol-2-yl]-2,6-dimethoxybenzamide;
N-[5-(2-methoxy-1,1-dimethylethyl)-1,3,4-thiadiazole-2-yl]-2,6-dimethoxybenzamide;
N-[5-(1,1-dimethyl-3-butenyl)-1,3,4-thiadiazol-2-yl]-2,6-dimethoxybenzamide;
N-[5-(2-chloro-1,1-dimethylethyl)-1,3,4-thiadiazol-2-yl]-2,6-dimethoxybenzamide;
N-[5-(2,2-dimethylpropyl)-1,3,4-thiadiazol-2-yl]-2,6-dimethoxybenzamide;
N-[5-(1-methylcyclobutyl)-1,3,4-thiadiazol-2-yl]-2,6-dimethoxybenzamide;
N-[5-(1,1-dimethyl-2-propenyl)-1,3,4-thiadiazol-2-yl]-2,6-dimethoxybenzamide;
N-[5-(1-ethyl-1-methypentyl)-1,3,4-thiadiazol-2-yl]-2,6-dimethoxybenzamide;
N-[5-(1-ethyl-1-propylbutyl)-1,3,4-thiadiazol-2-yl]-2,6-dimethoxybenzamide;
N-[5-(1-ethyl-1,3-dimethylbutyl)-1,3,4-thiadiazol-2-yl]-2,6-dimethoxybenzamide;
N-[5-(1,1-dimethyl-2-methoxypropyl)-1,3,4-thiadiazol-2-yl]-2,6-dimethoxybenzamide;
N-[5-(1-methyl-1-methylthiopropyl)-1,3,4-thiadiazol-2-yl]-2,6-dimethoxybenzamide;
N-[5-(1-ethyl-1-methylthiopropyl)-1,3,4-thiadiazol-2-yl]-2,6-dimethoxybenzamide;
N-[5-(1-methyl-1-methylthiomethylpropyl)-1,3,4-thiadiazol-2-yl]-2,6-dimethoxybenzamide.

3. The compound of claim 1, said compound being N-[5-(1-ethyl-1-methylpropyl)-1,3,4-thiadiazol-2-yl]-2,6-dimethoxybenzamide.

4. The compound of claim 1, said compound being N-[5-(1,1-diethylpropyl)-1,3,4-thiadiazol-2-yl]-2,6-dimethoxybenzamide.

5. The compound of claim 1, said compound being N-[5-(1,1-dimethylhexyl)-1,3,4-thiadiazol-2-yl]-2,6-dimethoxybenzamide.

6. The compound of claim 1, said compound being N-[5-(1-ethylpentyl)-1,3,4-thiadiazol-2-yl]-2,6-dimethoxybenzamide.

7. The compound of claim 1, said compound being N-[5-(1-methylcyclohexyl)-1,3,4-thiadiazol-2-yl]-2,6-dimethoxybenzamide.

8. The compound of claim 1, said compound being N-[5-(1-ethyl-1-methylbutyl)-1,3,4-thiadiazol-2-yl]-2,6-dimethoxybenzamide.

9. The compound of claim 1, said compound being N-[5-(1-methylcyclopentyl)-1,3,4-thiadiazol-2-yl]-2,6-dimethoxybenzamide.

10. The compound of claim 1, said compound being N-[5-(1,2-dimethylpropyl)-1,3,4-thiadiazol-2-yl]-2,6-dimethoxybenzamide.

11. The compound of claim 1, said compound being N-[5-(1-ethylcyclohexyl)-1,3,4-thiadiazol-2-yl]-2,6-dimethoxybenzamide.

12. The compound of claim 1, said compound being N-[5-(1,1-diethylbutyl)-1,3,4-thiadiazol-2-yl]-2,6-dimethoxybenzamide.

13. The compound of claim 1, said compound being N-[5-(1-isopropylcyclohexyl)-1,3,4-thiadiazol-2-yl]-2,6-dimethoxybenzamide.

14. The compound of claim 1, said compound being N-[5-(1,1,2-trimethylpropyl)-1,3,4-thiadiazol-2-yl]-2,6-dimethoxybenzamide.

15. The compound of claim 1, said compound being N-[5-(1-ethylcyclopentyl)-1,3,4-thiadiazol-2-yl]-2,6-dimethoxybenzamide.

16. The compound of claim 1, said compound being N-[5-(1-methyl-1-propylbutyl)-1,3,4-thiadiazol-2-yl]-2,6-dimethoxybenzamide.

17. The compound of claim 1, said compound being N-[5-(1,1,2,2-tetramethylpropyl)-1,3,4-thiadiazol-2-yl]-2,6-dimethoxybenzamide.

18. The compound of claim 1, said compound being N-[5-(1,1-dimethylpropyl)-1,3,4-thiadiazol-2-yl]-2,6-dimethoxybenzamide.

19. The compound of claim 1, said compound being N-[5-(1-propylcyclohexyl)-1,3,4-thiadiazol-2-yl]-2,6-dimethoxybenzamide.

20. The compound of claim 1, said compound being N-[5-(1,1-dimethylpentyl)-1,3,4-thiadiazol-2-yl]-2,6-dimethoxybenzamide.

21. The compound of claim 1, said compound being N-[5-(1-n-propylcyclopentyl)-1,3,4-thiadiazol-2-yl]-2,6-dimethoxybenzamide.

22. The compound of claim 1, said compound being N-[5-(1,1,2-trimethylbutyl)-1,3,4-thiadiazol-2-yl]-2,6-dimethoxybenzamide.

23. The compound of claim 1, said compound being N-[5-(1,1-dimethylethyl)-1,3,4-thiadiazol-2-yl]-2,6-dimethoxybenzamide.

24. A compound of claim 1 wherein:

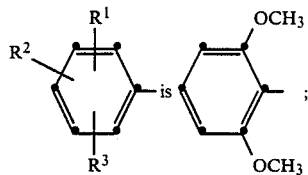

$R^5$ is

$R^6$ is $C_1$–$C_4$ alkyl, $C_2$–$C_4$ alkenyl, or $C_2$–$C_4$ alkynyl;
$R^7$ is $C_1$–$C_4$ alkyl; and
$R^8$ is $C_1$–$C_{13}$ alkyl.